(12) United States Patent
Simpson et al.

(10) Patent No.: US 9,572,909 B2
(45) Date of Patent: Feb. 21, 2017

(54) ELECTROSPUN NERVE GUIDES FOR NERVE REGENERATION DESIGNED TO MODULATE NERVE ARCHITECTURE

(75) Inventors: David Simpson, Mechanicsville, VA (US); Gary Bowlin, Mechanicsville, VA (US); Raymond Colello, Chester, VA (US); Woon Chow, Glen Allen, VA (US); Balendu Shekhar Jha, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 1227 days.

(21) Appl. No.: 13/394,415

(22) PCT Filed: Sep. 14, 2010

(86) PCT No.: PCT/US2010/048744
§ 371 (c)(1),
(2), (4) Date: May 17, 2012

(87) PCT Pub. No.: WO2011/032139
PCT Pub. Date: Mar. 17, 2011

(65) Prior Publication Data
US 2012/0221025 A1  Aug. 30, 2012

(51) Int. Cl.
*A61L 27/18* (2006.01)
*A61F 2/02* (2006.01)
*A61B 17/11* (2006.01)

(52) U.S. Cl.
CPC .......... *A61L 27/18* (2013.01); *A61B 17/1128* (2013.01); *A61F 2/02* (2013.01); *A61L 2430/32* (2013.01)

(58) Field of Classification Search
None
See application file for complete search history.

(56) References Cited

U.S. PATENT DOCUMENTS

| 6,033,685 | A  | * | 3/2000  | Qiu et al. ................. 424/464 |
| 6,235,041 | B1 | * | 5/2001  | Cheng ................ A61B 17/1128 606/152 |
| 2002/0156150 | A1 |   | 10/2002 | Williams et al. |
| 2005/0112349 | A1 |   | 5/2005  | Lauencin et al. |
| 2006/0159718 | A1 |   | 7/2006  | Rathenow et al. |
| 2007/0087025 | A1 |   | 4/2007  | Fitzhugh et al. |
| 2007/0269481 | A1 | * | 11/2007 | Li et al. .................. 424/423 |
| 2011/0125170 | A1 | * | 5/2011  | Hoke ................ A61B 17/1128 606/152 |

OTHER PUBLICATIONS

Dodla et al. Biomaterials 2008 29:33-46.*
Chew et al. Advanced Functional Materials 200717:1288-1296.*

* cited by examiner

*Primary Examiner* — Robert A Wax
*Assistant Examiner* — Caralynne Helm
(74) *Attorney, Agent, or Firm* — Whitham, Curtis & Cook, P.C.

(57) ABSTRACT

Nerve guides which are formed from three dimensional (3D) arrays of highly aligned electrospun fibers are provided. The electrospun fibers are oriented parallel to the long axis of the guide, and gaps and elongated spaces between the stacked fiber arrays provide channels for directed axonal growth. In some embodiments, the nerve guides also comprise high precision gradients of beneficial substances such as growth factors, which aid in nerve regeneration and growth along the guide.

11 Claims, 21 Drawing Sheets

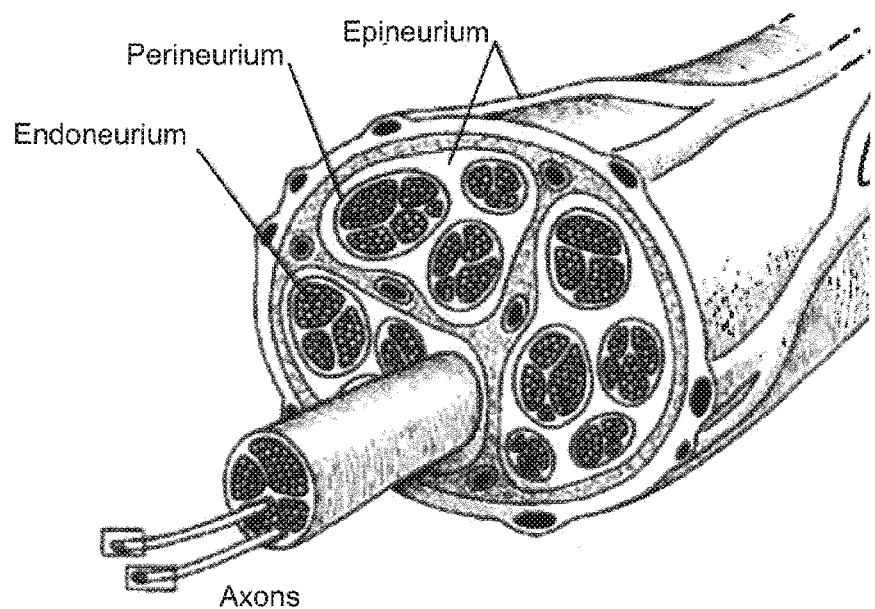
*Figure 1*
 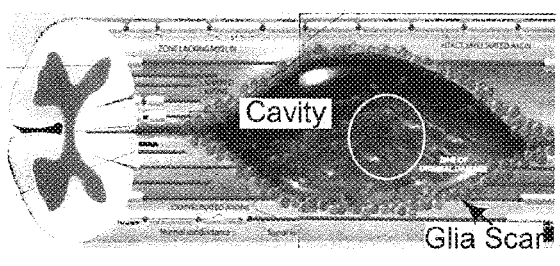 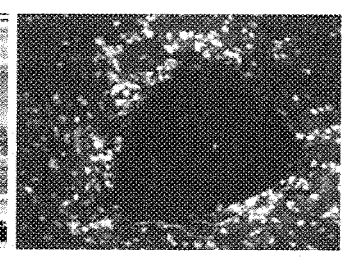
*Figure 2A*  *Figure 2B*  *Figure 2C*

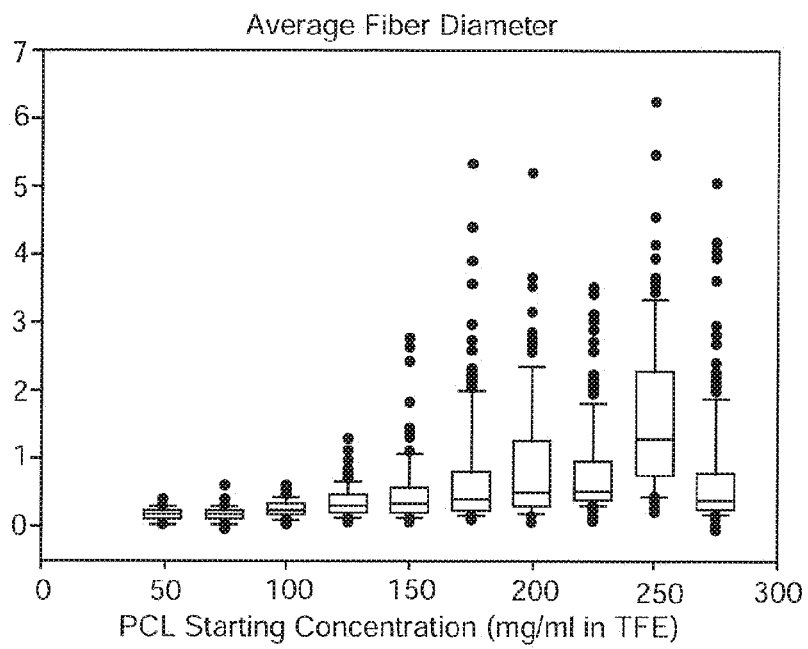
*Figure 8A*
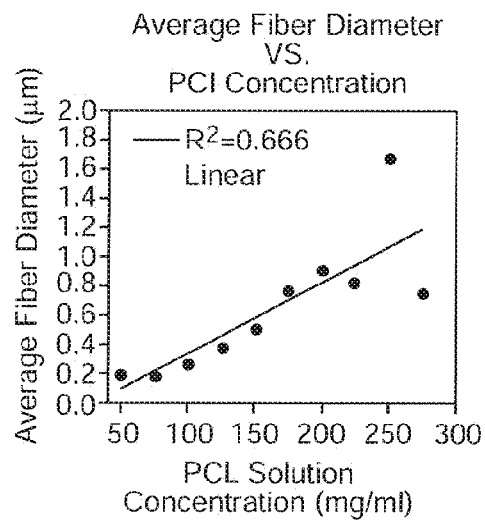
*Figure 8B*
|     | 50  | 75  | 100   | 125   | 150   | 175   | 200   | 225   | 250   | 275   |
|-----|-----|-----|-------|-------|-------|-------|-------|-------|-------|-------|
| 50  | NA  | XXX | 0.001 | 0.001 | 0.001 | 0.001 | 0.001 | 0.001 | 0.001 | 0.001 |
| 75  |     | NA  | 0.001 | 0.001 | 0.001 | 0.001 | 0.001 | 0.001 | 0.001 | 0.001 |
| 100 |     |     | NA    | 0.001 | 0.001 | 0.001 | 0.001 | 0.001 | 0.001 | 0.001 |
| 125 |     |     |       | NA    | XXX   | 0.001 | 0.001 | 0.001 | 0.001 | XXX   |
| 150 |     |     |       |       | NA    | XXX   | 0.001 | 0.001 | 0.001 | XXX   |
| 175 |     |     |       |       |       | NA    | XXX   | XXX   | 0.001 | XXX   |
| 200 |     |     |       |       |       |       | NA    | XXX   | 0.001 | XXX   |
| 225 |     |     |       |       |       |       |       | NA    | 0.001 | XXX   |
| 250 |     |     |       |       |       |       |       |       | NA    | XXX   |
| 275 |     |     |       |       |       |       |       |       |       | NA    |
*Figure 8C*

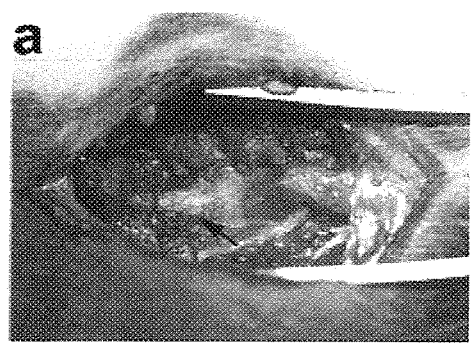
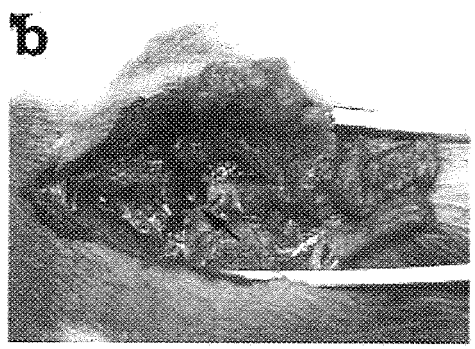
Figure 19A              Figure 19B
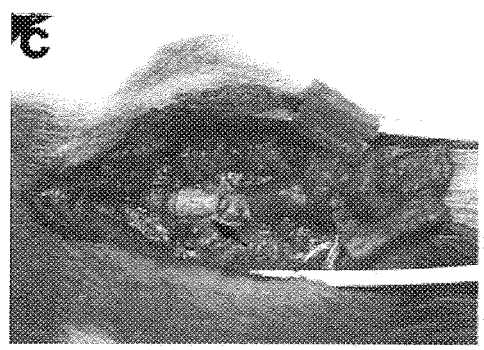
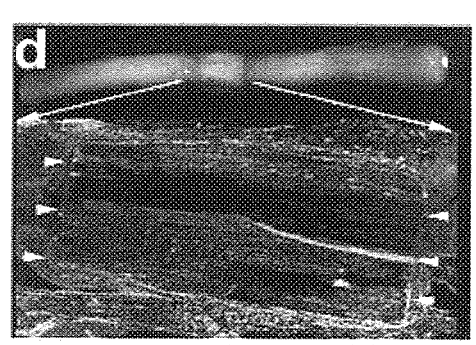
Figure 19C              Figure 19D
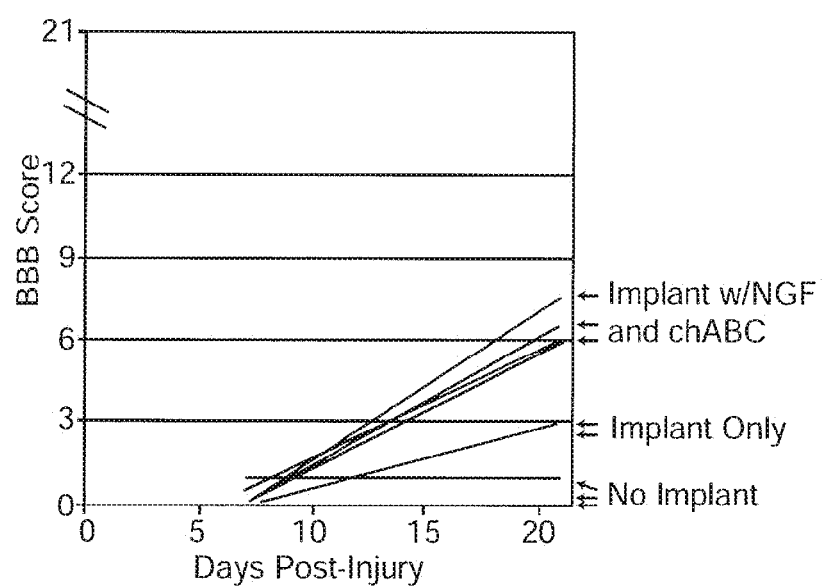
Figure 19E

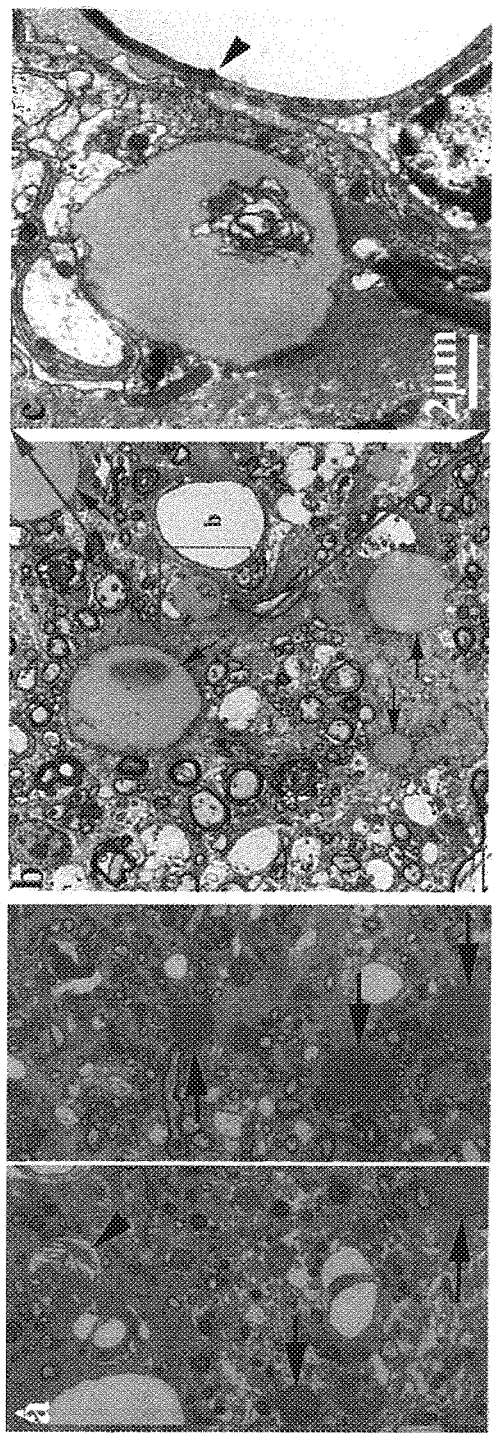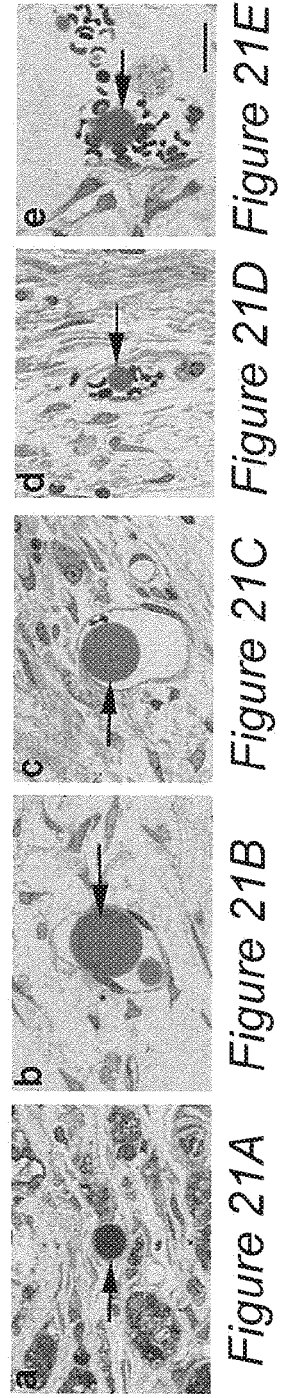

ELECTROSPUN NERVE GUIDES FOR NERVE REGENERATION DESIGNED TO MODULATE NERVE ARCHITECTURE

CROSS-REFERENCE TO RELATED APPLICATIONS

This application is a 371 of international application No. PCT/US2010/048744, filed Sep. 14, 2010, which claims benefit of U.S. provisional application No. 61/242,150, filed Sep. 14, 2009, and U.S. provisional application No. 61/323,387, filed Apr. 13, 2010, each of which is incorporated herein by reference.

BACKGROUND OF THE INVENTION

Field of the Invention

The invention generally relates to nerve guides for use in nerve regeneration. In particular, the invention provides nerve guides which are formed from three dimensional (3D) arrays of highly aligned electrospun fibers that are oriented in parallel with the long axis of the seamless and cylindrically shaped constructs. Gaps and elongated spaces between the stacked fiber arrays provide channels for directed axonal growth.

Background of the Invention

A peripheral nerve is an enclosed, cable-like bundle of peripheral axons (long, slender projections of neurons, see FIG. 1). A nerve provides a common pathway for the electrochemical nerve impulses that are transmitted along each of the axons. Each nerve is a cordlike structure that contains many axons. These axons are often referred to as "(nerve) fibers". Within a nerve, each axon is surrounded by a layer of connective tissue called the endoneurium. The axons are bundled together into groups called fascicles, and each fascicle is wrapped in a layer of connective tissue called the perineurium. Finally, the entire nerve is wrapped in a layer of connective tissue called the epineurium. Herein, "nerve" and "axon" may be used interchangeably.

After an injury, peripheral nerves can undergo an astounding degree of regeneration. When a nerve is severed, all signals distal to the injury site are immediately lost. Over time, downstream axons undergo Wallerian degeneration [1]. The surviving nerves of the proximal segment subsequently begin to undergo regeneration in response to soluble factors, many of which are produced by Schwann cells [2,3]. If the precipitating injury cleanly severs the nerve, treatment may be confined to a surgery that is designed to re-establish the continuity between the truncated stumps of the damaged nerve. In this surgery the proximal and the distal aspects of the perineural sheath are sutured together to form an end-to-end anastomosis. In more extreme injuries where a long segment of the nerve is crushed or completely lost, treatment is greatly complicated. Under these conditions a conduit, or nerve guide, is used to bridge the gap and direct the regenerating axons to grow towards the distal stump.

Nerve guides in the peripheral nervous system have a relatively long clinical history; these tubular constructs are designed to direct the natural processes that lead to regeneration [4,5]. A variety of natural and bioengineered materials have been used in this type of application, with mixed success [6]. Early synthetic guides consisted of a simple, hollow tube that provided little more than a protected environment [7]. With the hollow core design regenerating axons literally spill out of the proximal nerve stump and grow down the conduit. This not-so subtle "spilling effect" jumbles normal nerve topography (this term refers to the relative position of the individual axons to each other within the nerve) and greatly reduces the efficiency, and fidelity, of axon targeting.

Next generation peripheral nerve guides have been fabricated to contain signal molecules [8] and/or structural features [9] that are intended to provide guidance cues to the regenerating axons. Functional recovery with these constructs can be quite extensive, as long as the nerve guide is used to bridge a gap of less than about 10 mm in length. Once the injury gap exceeds this threshold, the regeneration process will be compromised to varying degrees. Typically, in these injuries only a limited number of axons will actually traverse the wound bed and the efficiency of targeting to the distal tissues is poor, resulting in limited functional recovery. Further exacerbating these complications, a series of irreversible degenerative changes begin to evolve in the distal tissues. As these degenerative changes become entrenched, the prospects of meaningful functional recovery are greatly diminished, even if a large number of axons are efficiently targeted to these sites.

Despite extensive and continued development, the autologous nerve segment represents the state of the art treatment for long defect nerve injuries. This tissue is highly anisotropic and its native architecture provides many potential channels to guide regenerating axons across the wound bed. However, use of this autologous tissue comes at the expense of donor site morbidity and results in the transplantation of a "nerve guide" that is packed with axonal fragments. These fragments must first degenerate before the regenerating axons can penetrate into the remaining endoneurium of the tissue. This degeneration process slows regeneration by initially impairing the penetration of the nascent axons into the autograft, a complication that clearly exacerbates the effects of long term muscle de-innervation and tissue atrophy.

In many ways there are similarities between peripheral nerve and the spinal cord. Both have a highly organized anisotropic structure and axons organized into specific topographical relationships. One clear difference that distinguishes spinal cord tissue from the peripheral nervous system is the observation that the spinal cord has axons that travel from the brain downward to the base of the spinal cord and out into the peripheral tissues as well as axons that travel from the peripheral tissues upwards towards the brain. For complete regeneration to occur after spinal cord injury both aspects of this "two way trafficking" of axons must be restored. Spinal cord injury (SCI), in both human insults and animal models, results in the liquefactive necrosis of the tissue in and around the lesion site. A fluid-filled cyst commonly emerges as the final consequence of this process (FIG. 2). Due to the lack of a solid substrate, this late-stage pathological endpoint represents a physical gap that impedes axonal regeneration and functional recovery. Additionally, astrocytes within the injury site proliferate, hypertrophy and begin to express chondroitin sulfate proteoglycans (CSPGs), which represent potent inhibitors to axon regeneration. At the neuronal level, axotomy of motor and sensory neurons results in the loss of trophic support by target tissue, which exasperates neuronal cell death. Additionally, the presence of myelin debris, as a result of oligodendrocyte death, acts as a potent inhibitor to axon regeneration in the spinal cord. Collectively, these cellular responses to spinal cord injury represent major impediments to axon regeneration and functional recovery.

Mono-therapies that address each of these obstacles to regeneration individually have resulted in only limited axonal regrowth and functional recovery. To date, no single intervention has been devised to collectively address all of the known obstacles to axon regeneration in the spinal cord.

Several studies have demonstrated that aligned arrays of electrospun fibers can provide the guidance cues necessary to induce axons and glial cells to express a highly polarized phenotype [10-13]. Despite these preliminary and encouraging results, it is difficult to fabricate a clinically relevant nerve guide using the conventional electrospinning process which uses a rapidly rotating target mandrel to produce aligned fibers. Conventional electrospinning systems are very effective at producing flat, 2D sheets with highly anisotropic fibers [14-16]. These constructs are easily amenable to experimentation in vitro, however, a 2D sheet is less acceptable, or adaptable, for use in vivo. A flat 2D sheet can be spun into a very thick structure and then cut into strips that resemble "square cylinders." These structures are technically seamless, however, fiber alignment tends to degrade the thicker a sheet becomes when fibers are processed under conventional 2D electrospinning conditions. Cutting such a sheet also distorts the existing alignment along the cutting plane. Also, in conventional electrospinning systems fiber alignment as induced by a rotating target mandrel is far more dependent upon fiber diameter than in the air gap system. In part this is because air currents and complex electric fields induced by the rotation of the mandrel disturb the trajectory of the charged jet, fiber flight and fiber deposition onto the target, thereby limiting the extent of alignment that can be achieved. Air gap electrospinning does not require any mandrel movement to induce fiber alignment, making it possible to produce aligned fiber arrays even when the biopolymer concentration is at the minimal threshold necessary to produce fibers. This allows highly aligned constructs to be fabricated from individual fibers of less than 200 microns in average cross sectional diameter, a size scale far smaller than can be achieved in conventional systems. Despite these limitations, the efficacy of using the conventional electrospinning process to fabricate hollow, cylindrical nerve guides has been explored to some extent. In these experiments the electrospun fibers have been deposited onto a round, rotating mandrel. While the fibers of this type of construct can be induced to exhibit a considerable degree of alignment when produced under these conditions, the fibers, unfortunately, are deposited onto the target mandrel in a circumferential orientation (i.e. the axis of alignment is ~90° off with respect to the resulting long axis of the hollow tube). While the nano-to-micron diameter fibers that form the wall of this type of construct do represent a barrier that reduces the risk of inflammatory cells penetrating into the hollow lumen of the guide (critical to the regeneration process [17,18]), this architectural pattern (i.e. the arrangement of electrospun fibers in a circumferential pattern) does not lend itself well to providing directional guidance cues to regenerating axons.

Other attempts at making nerve guides from electrospun (and other) types of fibers generally involve rolling sheets of material to form tubes. Unfortunately, the resulting tubes are hollow and thus fail to mimic the architecture of natural nerve growth. Further, a flat sheet that is rolled into a tube must, of necessity, have "seams" where the edges of the rolled sheets are surface exposed, e.g. on the wall of the hollow center of the tube and/or on the surface of the tube, resulting in discontinuities and possible weak connective points in the structure. In attempts to produce a more autologous graft-like structure aligned sheets of electrospun materials and films have been prepared and rolled tightly into more compact structures (32,33). (The final construct resembles a cinnamon breakfast roll where the electrospun sheets are represented by the dough, and the gaps or seams between the rolled sheets are represented by the sugar and cinnamon). While these structures are composed of "aligned fiber arrays" even these structures contain large seams (with respect to the size of the axons), no matter how tightly they may be rolled during fabrication. These seams represent a potential nexus for mechanical failure and the infiltration by unwanted interstitial fibroblasts and or inflammatory cells. Rolling a sheet can not truly integrate the fibers on the nano-scale that is necessary to make a uniform set of "pores". The gaps represent large "circumferentially aligned longitudinal pores (seams)" for axons to grow along on the underlying aligned fibers. In a sense this type of design provides a larger "2D" surface area to guide the growth of axons that are growing along the seams of the rolled sheets.

U.S. Pat. No. 6,031,148 (Hayes) discloses nerve guides made from rolled sheets of material which have hollow centers.

U.S. Pat. No. 6,821,946 (Goldspink et al.) discloses administering growth factors to damaged nerves via a conduit of unidirectionally oriented fibers containing an alginate matrix. However, the conduits are rolled sheets which form a tube with a hollow center that contains seams.

U.S. Pat. No. 7,374,774 (Bowlin) teaches electrospun materials with various uses, e.g. as nerve guides. However, the nerve guides are formed by rolling sheets of fibers, and thus have a hollow center and once again contains seams as a consequence.

US patent application 2010/0047310 (Chen et al.) discloses nerve guides comprised of biodegradable, biocompatible electrospun material. However, the guides are made from sheets of several layers of conduits which are rolled into cylinders and are thus hollow.

U.S. Pat. No. 7,727,441 (Yost et al.) describes a tubular tissue scaffold which comprises a tube having a wall, wherein the wall includes biopolymer (collagen) fibrils that are aligned in a helical pattern around the longitudinal axis of the tube, and where the pitch of the helical pattern changes with the radial position in the tube wall. The scaffold is capable of directing the morphological pattern of attached and growing cells to form a helical pattern around the tube walls, but would not be suitable for use as a nerve guide, where the axons must grow straight down the guide and not wrap or change topology during growth.

SUMMARY OF THE INVENTION

The invention provides nerve guides formed from electrospun fibers for use in the directed regeneration of damaged or severed peripheral nerves. The technique of static air-gap electrospinning is used to generate cylindrical, seamless three dimensional (3D) arrays of highly aligned electrospun fibers oriented in parallel with the long axis of the construct. The air-gap technique allows the fabrication of cylinders of aligned fibers without "rolling" a sheet of fibers, and thus no potentially weakening or irregular seams or inordinately large "pores" are present in the guide, and the guide does not contain a "hollow" central channel. Instead, the guide comprises multiple open channels formed by elongated gaps between the fibers, and the channels are lined with aligned fibers that are oriented along the long axis of the guide and bounded by elongated, oriented fibers. The fibers of these structures are integrated on a true nano-scale. And, unlike other nerve guides that may contain hundreds to thousands of channels that are designed to support axon regeneration. A similar sized electrospun 3D nerve guide (depending on its size and fiber characteristics) produced by air gap electrospinning may contain hundreds of thousands to tens of millions of individual channels, each of which is "lined" with nano-to-micron scale diameter fibers that are designed to provide guidance cues. When the proximal end of a truncated nerve is introduced into one end of the nerve guide, the nerve tissue grows into the guide and along the channels in a directed manner. Thus, an axon which grows through the guide emerges from the other end of the guide at a desired, predictable location, e.g. in close proximity to the other, distal end of the severed nerve. This insures that the severed nerve ends will grow with a minimum of excess or random nerve tissue growth, permitting reconnection of the severed nerve to its distal target tissues, and restoration of functionality. The nerve guides of the invention thus closely mimic and have the structural advantages of natural nerve grafts but without the undesirable side effects of nerve disintegration. Experimental results presented herein show that animals treated with the nerve grafts of the invention showed levels of functional recovery after 7 weeks that are normally observed in animals treated with autologous grafts after 10-14 weeks. In some embodiments, the nerve guides also comprise gradients of therapeutic substances.

It is an object of this invention to provide an architectural arrangement that mimics the structure of the native autologous graft by depositing nano-to-micron scale electrospun fibers into a seamless, cylindrical structure. The axons are guided to grow in between the aligned fiber arrays in the channels provided between the individual fibers. This design provides physical guidance cues to direct the axons to grow along a specific direction and along a specific plane in order to reconstitute the topography of the nerve that existed before an injury. Maintaining normal topographical relationships is intended to increase the fidelity of axon targeting and increase the likelihood that an axon will emerge from the distal end of the graft in a position that approximates its position prior to injury. In turn, this type of regenerative patterns is designed to increase the probability that the regenerating axon returns to the distal target tissue (sensory and motor) that it innervated prior to injury. In addition, the seamless nature of the guide provides a far more uniform profile of pore spaces (i.e. the channels between the individual fibers) than a rolled sheet of material, reducing the tendency, of axons to cluster and grow as a jumbled disorganized mass along the seams, a pattern of growth in a regenerating nerve which is associated with reduced axon targeting. Because the air gap electrospinning process is very rapid it is possible to place substances of interest, e.g. cells, therapeutic agents, gradient threads (as described herein), etc. within the scaffold as the fibers are depositing into the fiber arrays. The supplementation of the guides with growth factors and/or cells, etc. can be used to further regulate the regenerative environment afforded by the scaffolds.

The invention thus provides a nerve guide comprising a plurality of electrospun fibers which are seamlessly aligned parallel to a long axis of said nerve guide; and a plurality of open channels aligned parallel to the long axis of the nerve guide. In some embodiments, the nerve guide further comprises a carrier thread comprising one or more therapeutic substances in a gradient, which may include at least one growth factor. In some embodiments, an outer sheath is present on the nerve guide.

The invention also provides a method of facilitating (supporting, inducing, etc.) regeneration of a severed nerve. The method comprises the steps of i) attaching a proximal stump of the severed nerve to a first end surface of a nerve guide and a distal end of the severed nerve to a second end surface of the nerve guide; and ii) allowing (growing) axons of the proximal stump to grow within one or more of said plurality of open channels. The nerve guide comprises: a plurality of electrospun fibers which are seamlessly aligned parallel to a long axis of the nerve guide, and a plurality of open channels aligned parallel to the long axis of the nerve guide. The nerve guide further may include a carrier thread comprising one or more therapeutic substances in a gradient, such as at least one growth factor. In one embodiment, the severed nerve is a peripheral nerve and the nerve guide further comprises an outer sheath. In another embodiment, the severed nerve is a spinal cord nerve.

The invention also provides a multi-segmented carrier thread comprising a plurality of segments, wherein each segment comprises at least one component with a concentration that differs from concentrations of the component in adjacent segments. The total length of the multi-segmented carrier thread is from about 5 mm to about 125 mm. A length of any one of the plurality of individual segments is from about 1 to about 10 mm. In one embodiment, the at least one component is alginate. In another embodiment, the at least one component is a therapeutic agent. In another embodiment, the multi-segmented carrier thread further comprises microbeads present in at least one of the plurality of segments, the microbeads containing an agent of interest.

The invention also provides a method of forming a polymerized step gradient, comprising the steps of i) adding, to a mold, a first polymerizeable solution comprising at least one substance of interest to a mold; ii) freezing the mold with the first polymerizeable solution therein; iii) adding a second polymerizeable solution comprising the at least one substance of interest into the mold, wherein a concentration of the at least one substance of interest in the second polymerizeable solution differs from a concentration of the at least one substance of interest in the first polymerizeable solution, and wherein the second polymerizeable solution comes into direct contact with the first polymerizeable solution upon introduction into the mold; iv) freezing said mold with said first and second polymerizeable solutions therein; v) repeating steps i)-iv) to form a series of polymerizeable solutions, wherein each successive polymerizeable solution that is added to the mold in the adding step comprises a different concentration of the at least one substance of interest than a polymerizeable solution that was added in an immediately previous adding step; vi) removing the series of polymerizeable solutions from the mold; and vii) exposing the series of polymerizeable solutions to conditions which cause polymerization of the series of polymerizeable solutions, thereby forming a polymerized step gradient. In some embodiments, the polymerizeable solutions comprise alginate, and the conditions which cause polymerization include exposure to calcium. In other embodiments, the method further includes a step of curing said polymerized step gradient, e.g. exposing the polymerized step gradient to hexafluorisopropanol.

The invention also provides a method of forming functional blood vessels along a regenerating severed spinal cord nerve, comprising the steps of i) attaching a proximal stump of the severed spinal cord nerve to a first end surface of a nerve guide and a distal end of the severed spinal cord nerve to a second end surface of said nerve guide; and ii) growing endothelial cells in the vicinity of the nerve guide the endothelial cells attaching to the nerve guide and forming functional blood vessels while axons of the proximal stump grow within one or more of the plurality of open channels. The nerve guide comprises a plurality of electrospun fibers which are seamlessly aligned parallel to a long axis of the nerve guide, and a plurality of open channels aligned parallel to the long axis of said nerve guide. In one embodiment, the electrospun fibers of the nerve guide are formed from polydioxanone.

BRIEF DESCRIPTION OF THE DRAWINGS

FIG. 1. Peripheral nerve schematic. The epineurium invests individual axons, forming a collar of Type IV collagen and laminin around each axon. The perineurium surrounds a small number of axons, forming bundles. The tough outer epineurium surrounds the entire nerve. (Stroncek and Reichert in Frontiers in Neuroscience: Indwelling Neural Implants, website located at ncbi.nlm.nih.gov).

FIG. 2 A-C. Magnetic resonance imaging (MRI) showing the presence of a cyst (denoted by arrow) in the cord of a human SCI patient; B, Schematic illustration of the cyst and axon damage that occurs in SCI (spinal cord injury); C, Cyst present within a rat spinal cord 2 weeks after injury. The cyst is surrounded by astrocytes, cell bodies, and neurite growth inhibitors.

FIG. 8A-C. Average Fiber Diameter. A, Average PCL cross-sectional fiber diameter varied as a function of starting conditions. Of note in the graphical representation the range of fiber diameters also increased with increasing polymer concentration. B, Average fiber diameter as a function of starting PCL concentration. From 50 to 200 mg/ml PCL average fiber diameter increased in a nearly linear fashion (linear regression analysis over this specific range of concentrations: $R2=0.918$), however, at concentrations above 200 mg/ml this relationship markedly deteriorated. Overall the entire range of starting concentrations that we investigated a quadratic equation best described the relationship between starting concentration and average fiber diameter, although even in that analysis the data represented a poor fit, at best ($R2=0.666$). C, Summary of pairwise comparisons across all treatment groups. The broad range of fiber diameters present in the scaffolds produced from 275 mg/ml solutions exhibited substantial overlap with a variety of other scaffolds. Scaffolds produced from this starting concentration had fibers that were not statistically different than scaffolds produced from the 125, 150, 175, 200, 225 and 250 mg/ml.

FIG. 19A-E. This panel illustrates surgical procedures used to place 3D electrospun scaffolds produced from polydioxanone (PDS) into a spinal cord defect. A, The rat spinal cord is exposed after laminectomy. B, A 3 mm section is removed by complete spinal cord transaction, leaving a 3 mm gap in the tissue. C, This gap is then filled with a segment of the electrospun scaffold either with or without various growth factors and or enzymes designed to promote regeneration. The growth factors are designed to support axon growth and survival, the chroidinase ABC enzyme is present to degrade the scar tissue that inhibits regeneration. D, a 10 mm section of spinal cord that has been repaired with an electrospun matrix is illustrated. The DAPI label revels a massive infiltration of cells into the implant (border marked by arrows). E, Graph depicting the improvement in hindlimb mobility of SCI rats with varying implants. A BBB Score of 21 represents complete mobility, a score of 0 represents complete paralysis. Animals treated with enhanced matrices exhibit significant improvement in functional recovery as compared to untreated controls rats. Electron micrographic surveys revealed dense accumulations of axons within the implants.

FIG. 20 A-C. Structure of rat spinal cord approximately 6 weeks after complete spinal cord transection. These images were captured from within the body of a 3D Polydioxanone (PDS) nerve guide/graft. A, illustrates the typical structure of the regenerating tissue. Samples were embedded in plastic and cut in cross section (perpendicular to axis of fiber alignment) and stained with trypan blue. Images were captured with a bright field microscope. The grafts are packed with dense arrays of axons. As evidenced by the circular profiles of the axons the vast majority of the regenerating axons present in this nascent tissue are cut in circular profiles, demonstrating the potent directional cues provided by the fibers. Arrows denote PDS fibers in both panels. B illustrates a similar region of the regenerating spinal cord, images captured by transmission electron microscopy. The circular structures surrounded by dense material can be definitively identified as axons. Intermingling these myelinated axons are un-myleinated axons. The box in B outlines a PDS fiber, shown at higher magnification in panel C. Note the PDS fibers do not become myelinated. Panel C illustrates the nature of PDS fibers, and the defect within the fiber is believed to represent a degenerative process that is associated with PDS resorption. This pattern is most likely similar to that structure observed in the light micrographic images in the first panel and marked by the arrowhead in the upper middle aspects of the image. The arrowhead in C denotes an endothelial cell.

FIG. 21A-E. This series of panels (A-E) documents the use of PDS fibers by endothelial cells as a scaffolding in the formation of functional blood vessels. In A, the arrow indicates a PDS fiber in cross section within a spinal cord implant. In panels B and C arrows point to PDS fibers surrounded by endothelial cells, early in the process the endothelial cells appear to be closely applied to the surface of the fibers. With time they appear less closely applied, this may be associated with the degeneration of the PDS fibers and or some process intrinsic to the endothelial cell biology. Panels (C, D and E) illustrate unprecedented results. As can be seen in these panels, the PDS fibers are surrounded by endothelial cells that have formed a functional blood vessel. Under all known circumstances, that we are aware of the presence, the contact of blood cells with a PDS fiber should induce a coagulation cascade and the formation of a clot. However, this is clearly not the case with the spinal cord grafts of the invention. In the spinal cord the PDS fibers co-exist within the lumens of functional blood vessels as indicated by the RBC observed in sections adjacent and encompassed by endothelial cells that surround the PDS fiber. This result may be unique to the spinal cord environment and points to a unique interaction between the endothelial cells and electrospun PDS fibers.

DETAILED DESCRIPTION

Figure 3A:
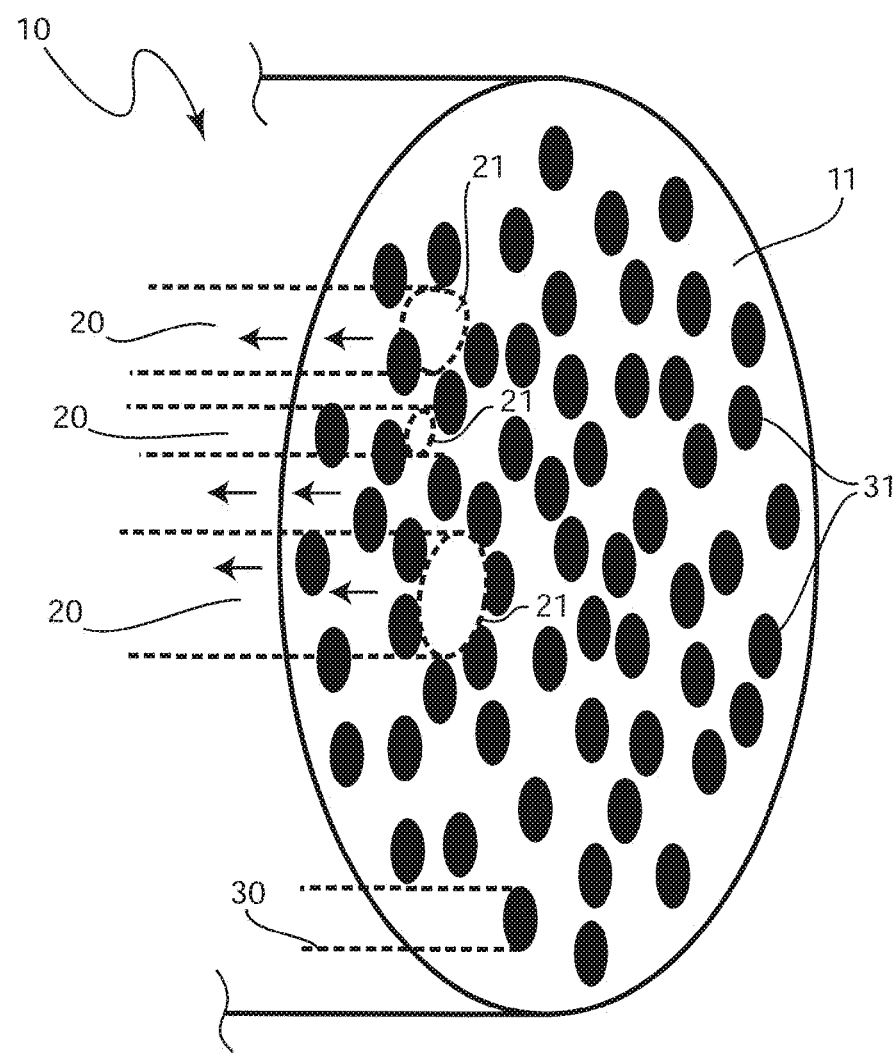
FIG. 3A-D. Schematic representations of features of the nerve guide of the invention. A, cross-sectional view of the nerve guide is depicted, showing, on the cross-sectional face, openings into the plurality of channels. The alignment of three of the channels parallel to the long axis of the guide is shown (dashed lines), with arrows indicating the direction of axon growth along (within) the channels; B, cross-sectional view of a single channel within a nerve guide showing a wall of the channel; C, nerve guide with sheath; D, nerve guide showing end surfaces.

The invention provides nerve guides formed from air-gap electrospun fibers for use in the directed regeneration of damaged or severed peripheral nerves and/or spinal cord injuries. In particular, the technique of air-gap electrospinning is used to generate three dimensional (3D) arrays or bundles of highly aligned electrospun fibers that are oriented in parallel with the long axis of the construct. When the end of a truncated nerve or spinal cord is introduced into, approximated or otherwise encounters one end of the nerve guide, the nerve tissue grows into the guide and along channels formed by elongated gaps between the individual fibers, the channels being oriented parallel to and along the length of the fibers, i.e. along the long axis of the guide. The construct thus guides unidirectional growth of the proximal end of a nerve toward a desired location, e.g. toward and directly up to the distal end of the severed nerve or damaged spinal cord. Herein, "proximal" refers to the end of a severed nerve that is closest to the center of the body or the brain and "distal" refers to the end that is further from the center of the body or further from the brain. These terms may also be applied to the nerve guides described herein, with respect to a view of the guide in a figure (the end closest to the viewer is the proximal end) and with respect to the connection to a severed nerve (the end of the guide that is connected to the proximal nerve stump is considered to be the proximal end of the guide), even though when out of this context, the two ends of the guide are substantially identical. Also, nerve refers to axons present in peripheral nerve and or spinal cord.

The invention thus provides a 3D, "semi-solid" nerve guide produced by air gap electrospinning. Air gap spinning makes it possible to produce microscopic (e.g. <5-10 mm in diameter) to macroscopic (e.g. >5-10 mm in diameter), cylindrical constructs comprised of dense anisotropic arrays (bundles) of nano-to-micron scale diameter fibers. These fibers are aligned in parallel with the long axis of the constructs, an architectural feature that provides thousands of individual channels (in turn, each is channel is lined with "aligned" arrays of fibers) that can be used to support, and direct, axon growth. With the use of the nerve guides of the invention, functional recovery in nerve injury is greatly improved because regenerating axons are confined to a specific tissue plane that mimics their original position within an intact nerve. The nerve guides of the invention thus cause regenerating axons to emerge from the distal aspect of the nerve guide in the near vicinity of where they existed prior to injury, increasing the probability of proper rejoining to the residual distal nerve stump.

Air-gap electrospinning is described in detail in the Examples section below. Briefly, this technique involves the use of two grounded targets which are static (not rotated) during the electrospinning procedure (although it should be noted that a device can be produced in which the targets are designed to rotate in synchrony to allow fibers to be deposited on all sides of the forming fiber array). An "air" gap (e.g. adjustable from 2-6 inches) separates the terminal ends of the two grounded targets. The electrospinning stream of charged polymers is directed into the air gap. As the charged polymer jet reaches the gap, it is laid out in a series of loops that pass back and forth between the grounded targets and collects as a parallel array of fibers, forming a seamless cylindrical construct. This process can induce fiber alignment over a wide range of spinning conditions (individual fibers of <200 nm to at least 3-4 μm in average cross sectional diameter) and depositing them in a static air gap system into macroscopic (up to at least 10 mm in diameter) 3D cylindrical arrays. Larger diameter structures can be produced in dynamic air gap systems. The packed fiber arrays of these constructs, in many ways, resemble the structure of an autologous nerve graft (e.g. compare FIGS. 1 and 2A). A complete discussion of this process is provided in Jha et al., 2010 In press Acta Biomaterials (reference 34).

While electrospun PCL may be used for the reconstruction of peripheral nervous system and electrospun PDS for use in the reconstruction of the central nervous system, it is recognized that other polymers (for example, PGA, PLA co-polymers of PGA PLA, polyesters, and native proteins such as collagens fibronectin, fibrinogens and other natural and synthetic proteins) may also be used in these applications. It is further recognized that, through the use of multiple electrospinning sources, different polymers and/or different polymer concentrations can be used to produce the guides. This may be particularly effective for use in spinal cord injuries. For example, synthetic fibers coated with specific materials (ECM including but not limited to collagen, laminin, fibronectin, Type IV collagen, other proteins such as fibrinogen, and/or cell surface proteins and intracellular proteins, pharmaceutical, growth factors etc) may be spun into the system for a defined interval of time, then a second source of material (different polymer, different concentration of same polymer, or polymer supplemented with different material) can be used to deposit additional arrays of fibers in a specific pattern onto the target. A similar pattern of fabrication can be used to produce arrays of different native proteins and or combinations of native electrospun proteins and synthetic fibers. For example, fibers in the core of the device may be composed of PDS (with or without additional materials added to the electrospinning solvent (as disclosed above), then the next outer fibers may be of a different polymer (with or without additional materials) and so on. Any number of different layers can be produced in this way. By simultaneously electrospinning from multiple-sources fibers of specific characteristics can be intermingled with one another in a seamless fashion on an individual fiber scale. In most electrospinning systems average pore dimension correlates roughly with average fiber size. Small fibers results in small pores, large fibers tend to produce larger pores (14). By intermingling different fiber sizes it is possible to regulate the number and size of pores present in a construct. It is desirable to match the diameter of the nerve guide and the number of pores with the number of axons present in a nerve that is being reconstructed as a strategy to suppress axon sprouting. Excessive axon sprouting can lead decreased axon targeting. By limiting the number of pores available for growth it may be possible to physically constrain this process and thereby increase the fidelity of regeneration. It is also recognized that materials can be dripped and or sprayed onto the forming device before during or after the fabrication process.

In addition, the data provided herein shows that an electrospun matrix produced by air gap electrospinning can be supplemented with proteins and enzymes that can promote neuronal survival and neutralize the growth inhibitory proteins associated with gliotic scar (or mesenchymal scar). Specifically, in vitro assays have demonstrated that nerve growth factor (NGF) delivered via alginate beads can be incorporated in an electrospun matrix and remain bioactive, as demonstrated by enhancing dorsal root ganglion (DRG) neuritic outgrowth. These data also suggest that delivery of this growth factor (and others) potentiates the biological activity of the growth factor, possible because it releases and/or delivers the growth factor in a more suitable tertiary structure for receptor binding. In addition, the data demonstrates how Chondroitinase ABC (ChABC) can be incorporated into the matrix and released in a bioactive form that neutralizes the axon growth inhibitory properties of CSPG. Collectively, these experiments point toward a novel approach by which a biocompatible matrix is used to bridge the fluid-filled cavity and provide regenerating axons with a directional matrix containing trophic and inhibitor neutralizing support. This multi-factorial approach is designed to address each of the specific defects known to inhibit axon regeneration in the central nervous system. Of note, the scaffolds can be prepared with specific growth factors placed in specific positions within the graft in order to selectively promote the growth of specific axon populations. For example some axons grow in response to nerve growth factor, other axon tracks grow in response to neurotrophin 3 (NT-3). By positioning the growth factors in specific locations and in gradients fabricated as described herein, the outgrowth of specific axon populations can be far more subtlely controlled than if the factors were present throughout the implanted scaffolds.

A cross-sectional view of an exemplary nerve guide is depicted schematically in FIG. 3A. This figures shows nerve guide 10 with cross sectional surface 11. Nerve guide 10 may be substantially cylindrical and comprises a plurality of electrospun fibers, proximal cross-sectional ends 31 of which are shown. For the sake of clarity, only one fiber 30 is depicted in phantom (dotted lines, near the bottom of the figure) as extending within and parallel to the long axis of the guide. However, one of skill in the art will understand that the guide contains hundreds of thousands to millions of such aligned fibers which extend from one end of the guide to the other, parallel to the long axis of nerve guide 10. Interspersed amongst the elongated fibers are hundreds of thousands to millions of channels 20 (i.e. elongated gaps or spaces, only three of which are shown in phantom by pairs of parallel dashed lines in FIG. 3A). Channels 20 extend continuously along and through the interior of the nerve guide substantially parallel to the long axis of the guide, and emerge at the other end of the guide. Channel openings 21 are shown on cross sectional surface 11. The channels do not contain seams (i.e. the edges of a rolled sheet of electrospun material is not present) and are not formed by rolling a 2D sheet of electrospun material. The channels in effect form a void space within the guide and the outer bounds of each channel (i.e. the wall of the channel) is formed by the outside surfaces of elongated fibers which traverse the length of the guide.

Figure 3B:
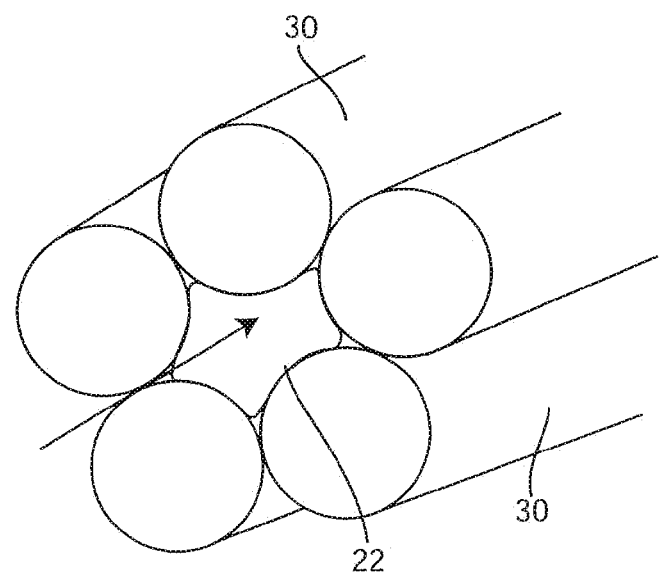

A single channel with channel wall 22 is depicted schematically in cross section in FIG. 3B. As can be seen, channel wall 22 is formed by the sides of fibers 30 which are arranged in a parallel array or bundle. As an axon grows along channel 22, it comes into direct contact with and in effect grows directly on and/or adjacent to the aligned fibers which define the channel. The pores or channels are depicted in FIG. 3A are approximately circular in cross section. In reality, they may have a more complex profile e.g. as in FIG. 3B, or may be even more complex. The "walls" that form the channel (which are represented as continuous or solid in FIG. 3B) are defined by a series of individual fibers that may or may not be fully longitudinally connected to one another in the fashion depicted in this schematic, and thus the channels may also be interconnected.

The aligned fibers provide a directional cue to the regenerating axons, which will tend to grow down the channel in the direction of fiber alignment, i.e. along the long axis of the guide. Conversely, one can consider the channels as a series of aligned open spaces established and bordered by the fibers. As can be seen, this structure closely resembles the architecture of a nerve (see FIG. 1), with the open channels providing a path for axon growth (e.g. in the direction of the arrows in FIG. 3A), the fibers providing a solid or semi-solid support by filling the space which, in a natural nerve, is occupied by the epinerium and/or perineurium. Significantly, the nerve guides of the invention are not formed by rolling flat, 2-dimensional sheets of fibers into a tube and thus do not have a single hollow center, nor do they have seams at any surface. In other words, the guide has a true 3-dimensional architecture as originally synthesized.

Figure 3C:
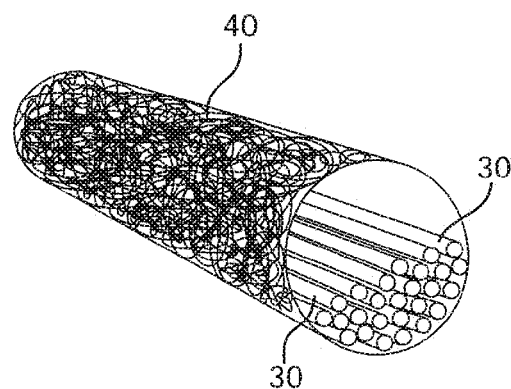

In some embodiments, the nerve guide also includes a sheath 40 (see FIG. 3C). Sheath 40 (which may also be referred to a coating or covering) may be formed by electrospinning (fibers) or electrospraying (droplets) a polymer or co-polymer directly onto the surface of the guide after it is constructed. The electrospun fibers of the sheath may be aligned with the long axis of the guide, or at an angle (e.g. 90°) with respect to the long axis of the guide, or may be non-aligned, randomly configured (disordered) in nature. FIG. 3C shows a schematic view of nerve guide 10 of the invention having an internal array of fibers longitudinally aligned with the long axis of the guide, and with outer sheath 40 formed from a mass of non-aligned electrospun fibers. Generally, the coating or sheath covers the entire outer surface of the guide except for the proximal and distal ends of the guide where the regenerating axons enter and leave the guide, respectively although this need not always be the case. In some embodiments, the sheath covers only a portion of the guide or may be absent all together. In other embodiments, it may be designed to overhang the ends of the guide and form a "sock-like" structure designed to slip over the ends of a cut or otherwise damaged nerve to facilitate placement of the guide. Experiments described herein showed very unexpected results with the outer sheath. When used in the peripheral nervous system, this sheath was very effective at reducing interstitial and inflammatory cell infiltration into the guides. However, the use of a similar sheath (or collar) in spinal cord reconstruction experiments produced the opposite result, the use of the sheath inhibited regeneration. When used, the sheath or covering is generally present at a depth of from about 50 microns to about 200 microns. The coating provides mechanical support to suppress compression or deformation of the guide (e.g. during manipulation and when in place in a subject), and is able to support sutures which connect the guide to a severed nerve end. In addition, the sheath may induce the formation of a fibrotic capsule which suppresses infiltration of inflammatory cells into the core of the guide (Telemeco et al, 2005). Exemplary materials for forming an electrospun coating include but are not limited to polygalactic acid (PGA)/PCL co-polymers, PGA, PDS, PLA, PDS and denatured collagens, e.g. gelatin which can be used to induce the formation of the fibrotic capsule necessary to protect the internal environment of the nerve guides. In some embodiments, the coating is not electrospun but instead is formed by coating the guide in some other manner e.g. adhering a suitable substance onto the external surface of the guide. In this embodiment, the substance that is chosen is generally of low or no toxicity, ("biocompatible"), and is usually designed to induce a mild inflammatory response to generate the subsequent formation of the fibrotic capsule For example, a PCL based nerve guide can be prepared and dipped into a solution of gelatin prepared in water (this solution can be prepared with or without additional therapeutic reagents and may be applied uniformly or in a gradient fashion over the outside surface of the guide, e.g. by dipping the device repeatedly and preferentially on one end into the solution). The PCL will largely be stable in the water for the short interval needed to coat the outer surface. Or alternatively the exterior may be coated with various materials simply by spraying or aerosoling the material onto the exterior of the device. The fibrotic capsule can also be induced to form through the application of specific reagents such as TGF-1 or other pro-inflammatory substances; this growth factor is a potent inflammatory agent. The use of this type of strategy will produce a capsule in the absence of any additional outside sheath through just the use of this growth factor. One skilled in the arts will also be cognizant that it is also possible to use anti-flammatory reagents where the formation of a fibrotic capsule is undesirable. In other embodiments, an electrospun sheath may be first attached to the guide, and then the electrospun or electrosprayed coating may be further "coated" with one or more layers of a suitable material or materials, such as PCL, PDS, PGA, PLA and selected proteins such as gelatin collagens and or fibrinogen) . The sheaths or coatings on the guide may further comprise therapeutic substances as well, e.g. antibiotics, growth factors, anti-inflammatory agents, pro-inflammatory agents, pharmaceuticals designed to promote axon regeneration/survival (cAMP and analogs of this signal reagent which promote axon growth and or regents designed to manipulate the NoGO system—which inhibits axon growth and can be blocked with pharmaceutical reagents and or antibodies—are of particular interest for use in spinal cord injuries). These factors may be added as a more or less uniform distribution on the guides or in specific patterns as required by specific circumstances.

The nerve guides of the invention are typically substantially (roughly, largely) cylindrical in shape and have a diameter in the range of from about 1 mm to about 20 mm (e.g. about 1, 2, 3, 4, 5, 6, 7, 8, 9, 10, 11, 12, 13, 14, 15, 16, 17, 18, 19, 20 mm, or in some cases even longer, e.g. up about 25 or 30 mm). Average fiber diameters for PCL based constructs may range from about 100 nm (e.g. about 50, 100, or 150 nm, or even about 200-250 nm) up to about 5 microns (e.g. about 1, 2, 3, 4, or 5, or more, microns). These values encompass the fiber diameters most suitable for electrospinning in the air gap system and for use in providing guidance cues to axons. However, typically these values will range from about 500 nm to about 2000 nm (e.g. about 500, 600, 700, 800, 900, 1000, 1200, 1300, 1400, 1500, 1600, 1700, 1800, or 1900 nm), depending upon specific applications. The nerve guides that we have used in reconstruction experiments in the rodent sciatic nerve and rodent spinal cord have a mean fiber diameter of about 1 micron but those skilled in the arts will realize that electrospun constructs are usually composed of range of fiber diameters. At 200 mg/ml PCL produced fibers ranging from about 50 nm all the way to 5 microns but the mean and median values are approximately 1 micron. The channels within the nerve guide generally occupy a total void volume of from about 50% to about 95% (e.g. about 50, 55, 60, 65, 70, 75, 80, 85, 90, or 95%), and most frequently from about 80% to about 95% (e.g. about 80, 85, 90 or 95%). A 10 mm diameter guide composed of individual fibers that are nominally 1 micron in diameter and void volume of approximately 90% will contain 10 million fibers (calculated from: where $(3.14)(5\ mm)(5\ mm)=78.5\ mm^2$. For a circular structure with 90% open space the total volume occupied by the fibers is $(0.1)(78.5\ mm^2)=7.85\ mm^2$. A 1 micron diameter fiber (assuming a circular profile) occupies $(3.14)(0.5)(0.5)=0.785\ \mu m^2$ of area. Total area occupied by the fibers is = $7,850,000\ \mu m^2$. Total area occupied by 1 fiber=$0.785\ \mu m^2$. Dividing total area occupied by fibers by the total area occupied by 1 fiber yields approximately 10,000,000 fibers). Assuming that pore spaces between the individual fiber approximate the diameter of the fibers, a similar calculation will provide an estimate of the total number of individual channels present in this type of construct. (Total area occupied by open spaces 90% or: $77,715,000\ \mu m^2$ for a 10 mm diameter nerve guide.) If the pores spaces are approximately the diameter of the fibers the total number of pores in this construct will be: $77,715,000\ \mu m^2/0.785\ \mu m^2=99,000,000$ potential channels; assuming 2 micron diameter channels yields=$77,715,000\ \mu m^2/3.14\ \mu m^2=24,750,000$ potential channels, assuming 5 micron diameter channels yields=$77,715,000\ \mu m^2/19.625\ \mu m^2=3,960,000$ channels). One skilled in the art will recognize that it may be desirable to match the total number of fibers or the total number of pore spaces to the estimated number of nerves present in an injury site. In addition, the length of the guides are generally in the range of from about 10 mm to about 125 mm for peripheral nerve injuries and from 2 mm to 50 mm for spinal cord. Those of skill in the art will recognize that the guides may be of any suitable length and circumference, and in fact may be fabricated or tailored for particular purposes, e.g. for use in different nerves, in particular individuals, for particular locations in the body, according to the type of lesion being treated, etc.

Those of skill in the art will recognize that a wide range of sizes of guides and numbers of channels might be suitable, depending for example on the type of nerve that is to grow through the guide, the distance the regenerating nerve should grow, the limits of the air-gap electrospinning method. In air gap electrospinning the total length of a construct that can be produced is depended upon the specific polymer to be spun and the starting concentration of that polymer. For example, for PCL prepared at 50 mg/ml in TFE the ideal distance between the target poles may be on the order of about 30-60 mm. At 200 mg/ml the distance between the target poles may be on order of 50-100 mm. We note that for PCL, and other polymers that very defined electrospinning conditions may be necessary to produce and collect fibers in the air gap system. For examples of specific conditions used to process PCL see table below, ambient conditions such temperature and humidity can alter these documented spinning conditions. The values provided in Table 1 are suitable for PCL in TFE at temperatures of about 680 F and a relative humidity of about 30-50%.

TABLE 1

Electrospinning conditions

| Starting Concentration | Washer Diameter | Ground Voltage | Polymer Delivery Rate | Spin Gap between polymer and target | Gap Between Target Poles |
|---|---|---|---|---|---|
| 50 mg PCL/ml TFE | 19 mm | −16 kV | 9 ml/hr | 25 cm | 5 cm |
| 75 mg PCL/ml TFE | 19 mm | −16 kV | 10 ml/hr | 25 cm | 6 cm |
| 100 mg PCL/ml TFE | 19 mm | −20 kV | 15 ml/hr | 25 cm | 6 cm |
| 125 mg PCL/ml TFE | 19 mm | −10 kV to −12 kV | 15 ml/hr | 25 cm | 6 cm |
| 150 mg PCL/ml TFE | 19 mm | −7 kV | 12 ml/hr | 21 cm | 6 cm |
| 175 mg PCL/ml TFE | 23 mm | −7 kV | 10 ml/hr | 18 cm | 6 cm |
| 200 mg PCL/ml TFE | 23 mm | −7 kV | 10 ml/hr | 18 cm | 6 cm |
| 225 mg PCL/ml TFE | 32 mm | −7 kV | 12 ml/hr | 16 cm | 5 cm |
| 250 mg PCL/ml TFE | 32 mm | −5 kV | 10 ml/hr | 15 cm | 5 cm |
| 275 mg PCL/ml TFE | 19 mm | −3 kV | 8 ml/hr | 13 cm | 5 cm |

Table I emphasizes that the conditions that must be used to electrospin in the air gap system can be very specific and require(d) empirical analysis to define. For example, the use of a conductive washer facilitates spinning in this system, whereas in conventional systems a needle will often suffice as a source for charging the system. This discussion documents specific conditions used to produce PCL based scaffolds. Washer diameter refers to the diameter of washer placed over the needle used to deliver the polymer solution to the electric field. This washer is necessary to overcome the point charge effects observed in the air gap system, without these round washers the PCL polymer fails to target properly (Other polymers, such as PDS under certain starting conditions spin better without the washer). Ground voltage refers to the common voltage applied to the paired target poles. These values were optimized based on fiber collection. For PCL the source solution was held constant and charged to 20 kV+ for all concentrations (ideal voltages may vary by polymer and solvent or melt conditions). Polymer delivery rate refers to the rate at which the polymer solution was delivered to the electric field. Too low or too fast of a delivery rate can result in the failure to collect fibers across the target array. Spin gap is the distance from the source solution to the target array. This interval is determined largely by the circular path of the charged electrospinning jet and is set so that the diameter of the spiral path coincides with the diameter of the gap between the target array (different distances will work, but often requires simultaneous adjustments in flow rate and electrospinning voltages). The gap between poles is a measure of the distance between the two target poles. These values were optimized based on fiber formation, but values outside these will work, however the accumulation of fibers is less efficient.

Figure 3D:
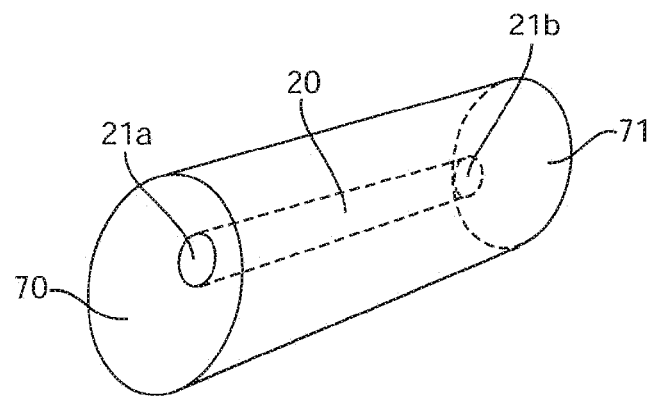

Those of skill in the art will recognize that the nerve guides of the invention will generally contain at least two suitable end surfaces (a first end surface and a second end surface), one at each end of the guide (e.g. at a proximal and a distal end, or at opposite ends) which are substantially flat and substantially circular (being roughly the cross-section of the cylindrical guide) and which contain or include openings into the channels located within the guide, thereby providing means of ingress and egress for the regenerating nerve. In some embodiments it may be necessary to have a guide shaped in the configuration which contains a branch point(s) to accommodate injuries that occur near where nerves may branch (for example near the separation of the tibial and common peroneal nerves from the sciatic nerve). FIG. 3D shows a schematic depiction of first end surface 70 and second end surface 71 (in phantom), with a single open channel 20 (also in phantom) traversing the guide there between. Channel openings 21a and 21b open on first end surface 70 and second end surface 71, respectively. The guides may contain these suitable end surfaces directly after electrospinning, or the guide may be further processed if necessary, e.g. by "trimming" the ends to form such end surfaces. Suitable surfaces may or may not have a diameter that is substantially the same as that of the guide itself, i.e. the diameter of an end surface may be somewhat larger, but usually may be somewhat smaller than that of the guide itself, e.g. if the distal and proximal end sections of the guide are somewhat tapered or sloped. In general, the diameter of each end surface of the nerve guides of the invention will be substantially the same and can be prepared to match the diameter of the specific nerve to be repaired. Typically, in the peripheral nervous system nerves that might be repaired range from about 1-15 mm in cross sectional diameter, although in some cases the diameter may be greater; this value will vary by individual and the exact position of the injury to be repaired. Values for the spinal cord may be similar. Most injuries in the spinal cord cause damage to a portion of the cord and not complete transection, rather by their nature these injuries usually damage a fraction of the total cross sectional diameter of the cord. To repair these injuries the damaged area (i.e. the cyst) may be excised and reconstructed with a nerve guide that fits the surgically induced deficit. However, it may be necessary to repair a large full diameter defect. Under these circumstances the nerve guide will be on the order of about 10-20 mm in diameter.

Typical relationships between average fiber diameter, estimated void space and average number of fibers per $mm^2$ of a cross section is as follows:

| Average Fiber Diameter | Estimated Void space | Average Number of Fibers/$mm^2$ |
|---|---|---|
| 100 nm | 0.55 | 45000000 |
| 200 nm | 0.55 | 11250000 |
| 300 nm | 0.6 | 4444444 |
| 500 nm | 0.85 | 600000 |
| 1000 nm | 0.85 | 150000 |
| 2000 nm | 0.9 | 25000 |
| 3000 nm | 0.92 | 8889 |
| 5000 nm | 0.95 | 2000 |

These numbers are calculated with the following assumptions: A. All fibers are uniform in diameter; B. Calculations based on given void space values which are extrapolated from studies described herein; and C, assumption of circular cross sections for all fibers.

Similarly, the average channel (pore) size and numbers per $mm^2$ in a cross section of the constructs are as follows:

| Average Pore Size | Average Number of Pores per 1 $mm^2$ |
|---|---|
| 100 nm | 55000000 |
| 200 nm | 13750000 |
| 300 nm | 6666667 |
| 500 nm | 3400000 |
| 1000 nm | 850000 |
| 2000 nm | 225000 |
| 3000 nm | 102222.2 |

-continued

| Average Pore Size | Average Number of Pores per 1 mm² |
|---|---|
| 5000 nm | 38000 |
| 10000 nm | 9500 |

These numbers are calculated with the following assumptions: A. All pores are circular in profile and uniform; B. Calculations are based on given void space values which are extrapolated from studies presented herein; C, Total pore area varies directly as a function of void volume assumptions.

While the nerve guides of the invention are generally configured as a single guide with multiple channels for fostering the directional growth of a single nerve stump, usually in a substantially straight line (as the shortest distance to be traversed by the regenerating nerve), this need not always be the case. The invention also encompasses other configurations of nerve guides, e.g. guides which are curved or bent at an angle, multiple guides connected end to end (e.g. to extend across longer distances), two or more guides which are attached side by side and/or on top of one another, etc. All such configurations are encompassed by the present invention.

Those of skill in the art will recognize that the electrospun fibers from which the guide if formed may be made of a suitable non-toxic material which is amendable to air-gap electrospinning, and which is capable of being slowly absorbed or dissolved under physiological conditions. The material should possess sufficient tensile strength and stability to permit manipulation (e.g. surgical suturing to a nerve end or other tissue), and to remain intact for a period of time sufficient to support nerve growth. However, the material should not be overly rigid, but should be somewhat flexible and conformable to the contours of the physiological environment in which it is used, and should ultimately be absorbed (resorbed, dissolved, etc.) within the body. Examples of such materials include but are not limited to polycaprolactone (PCL), Examples of such materials include but are not limited to polycaprolactone (PCL), Polydioxone (PDS), polylactides (PLA), polyglycolic acid (PGA), co-polymers of PGA PLA, polyvinyl alcohol (PVA), Polyethylene glycol (PEG), Poly ethylene oxide (PEO).

Other potential candidates include: poly(urethanes), poly (siloxanes), silicones, poly(ethylene), poly(vinyl pyrrolidone), poly(2-hydroxyethyl methacrylate), poly(N-vinyl pyrrolidone), poly(methyl methacrylate), poly(acrylic acid), polyacrylamide, poly(ethylene-co-vinyl acetate), poly(ethylene glycol), poly(methacrylic acid), polyanhydrides and polyorthoesters. Natural proteins including collagens, fibrinogens, fibronectin may also be used in the air gap electrospinning system to produce 3D nerve guides. It is should be noted that some polymers can be electropun as melts and do not require solvents. Also, while we have disclosed the use of electric fields in the fabrication of our aligned guides it is possible to process some polymers in very strong magnetic fields to produce fibers.

In most biological systems materials that can be degraded or dissolved are believed to be highly desirable for use in tissue engineering applications. With the advent of materials that can reside in an inert state and not induce adverse effects it may be desirable to use those materials in the discussed applications. Materials that are permanently indwelling may be used to support tissues that are top delicate to otherwise be maintained due to mechanical damage. For example nylon and other more or less permanent materials may be needed to support tissues that can not generate sufficient material strength to resist damage from mechanical traumas originating with movement or other insults.

Typically, a nerve guide is likely to be formed from PCL with a MW of 65000 daltons for the peripheral nervous system. Electrospun PCL produced from a starting concentration of about 200 mg/ml in TFE produces fibers that are approximately 1 micron in average cross sectional diameter. This particular formulation has a confluence of characteristics that provide a unique architectural and structural environment that fosters nerve regeneration. This formulation spins very well and targets into the 2 pole system efficiently (the spinning conditions that produce good fibers at lower PCL concentrations are far more restrictive and difficult to achieve, at higher concentrations the inherent limitations of the 2 pole electrospinning process restricts the overall length that can be achieved in the constructs). The 200 mg/ml formulation produces scaffolds that exhibit nearly no fiber defects. These constructs have approximately 90% void space between the fibers yet it suppresses axon aggregation and has excellent material properties that are sufficient to withstand mechanical insults. The exterior sheath used in the fabrication of these devices is typically composed of a PGA/PLA co-polymer coating that induces a mild inflammatory response and the formation of a fibrotic capsule. The guide is placed in contact with the stumps of the damaged nerve and sutured and glued in place. Specific growth factors that have been identified for use in these guides include nerve growth factor and or glial derived neurotrophic factor (GDNF).

In spinal cord injuries the nerve guide is composed of PDS (the parent polymer of this specific formulation is polydioxanone or PDO, PDO is not available commercially but is available for purchase as suture material or PDS suture). Ideally, the PDS suture is soaked in methylene chloride to remove the blue dye that is incorporated into it during the suture fabrication process. This dye reduces the "spinability" of the PDS. PDS is subject to the formation of peaks and ripples in the air gap process as it deposits across the target array when the blue and apparently charged dye is retained in the material. PDS is electrospun at concentrations ranging from about 100 mg/ml HFIP (fibers approximately 1 micron in average cross sectional diameter) to about 175 mg/ml HFIP (fibers that are approximately 1.5-1.7 microns in average cross sectional diameter). Specific factors that have been incorporated into these devices include cAMP analogs to drive axon growth and overcome the inhibitory effects of myelin on axon outgrowth, chondroitinase ABC enzyme (e.g. about 0.25-1.0 units per 3 mm implant) to degrade glial scar associated with spinal cord injury that inhibits axon growth, nerve growth factor as a tropic agent for axons, NT-3 (neurotrophin 3) as a tropic factor for axons, and BDNF (brain derived neurotrophic factor) as a tropic factor for axons. All growth factors were used at an estimated concentration of approximately 0.5-5 micrograms per 3 mm segment implanted into the rat, for human use these values can be scaled accordingly.

Of particular note for constructs designed to reconstruct spinal cord injuries, we have found that endothelial cells migrate along and attempt to surround PDS fibers that are about 0.5 to about 1.0 microns in diameter. With time as the fiber degrades, the endothelial cells remain and a capillary develops, with the lumen existing where the PDS fiber had at first been surrounded by the endothelial cells. This unexpected effect has not been observed in the peripheral nervous system to date in animals reconstructed with PCL based grafts and appears to be unique to the CNS (FIG. 20). This effect in the CNS is of interest for at least two reasons. First, the endothelial cells clearly preferentially appear to use these fibers as a preferred path upon which to penetrate into the scaffolds to provide nutrient and waste exchange support to the regenerating tissues. Second, it has been observed that capillaries formed by endothelial cells in the CNS form a template that directs the growth of CNS axons (35, 36). This growth occurs in parallel with those capillaries, thus the growth of endothelial cells along a defined track established by the PDS fibers will represent yet another cue to direct axons to grow down the guides. We also note that fiber alignment is crucial for axon penetration and growth. An excessive disturbance in fiber alignment at the terminal ends of the grafts can inhibit axon penetration, data that clearly demonstrates the utility and desirability of the fiber alignment possible using the air gap electrospinning system.

Specific additional reagents that may be desirable include extracellular matrix proteins mixed uniformly through out the scaffolds. These proteins, including laminin, collagens of various types including Type IV and Type I, fibronectin, RDG peptides, other binding moieties and fibrinogen (which are a potent promoter of axon growth). These materials may be mixed with the electrospinning reagents or alternatively the nerve guides can be immersed into them, or they may be aerosoled into the constructs during the fabrication process in the presence or absence of an electric field. Other reagents may include antibiotics, anti-inflammatory agents, pro-inflammatory agents, biologically active peptides, inert peptides, various cell types including Schwann cells, Glial cells, astrocytes, oligodentrocytes, endothelial cells and other cells that can naturally provide trophic support or those cells that have been engineered to provide trophic support to regenerating axons. For spinal cord treatments the incorporation of glial cells is of particular interest as these cells provide trophic support to regenerating axons while providing a functional barrier that inhibits the infiltration of unwanted interstitial fibroblasts into a nerve guide. Cells may be added simply by dribbling a highly concentrated solution of cells gradually into the forming fiber arrays or soaking the constructs in cells after the fabrication process. Or alternatively, cells may be introduced into the constructs by aerosol deposition in the prescence or absence of an electric field.

The nerve guides of the invention are gradually absorbed (resorbed, dissolved in, etc.) the bilogical fluid that surrounds them in the body. The rate of dissolution is calibrated (e.g. by the selection of polymer(s), by the thickness or size of the guide, by the presence of a covering or coating, etc.) so that the guide is present for at least about 5 weeks and usually for at least about 52 weeks, (and can be fabricated so as to be present for various times in between, e.g. about 10, 15, 20, 25, 30, 35, 40, 45, or 50 weeks) in order to facilitate nerve regeneration for a period of time that is long enough for the growing axons to reach and join to the distal nerve end. The precise time that is required may vary somewhat from circumstance to circumstance, depending e.g. on the type of lesion that needs to be repaired and the distance between the two severed nerve ends.

In some embodiments, the nerve guides of the invention also comprise gradients of soluble substances or agents that are therapeutically beneficial to regenerating nerves. The gradients are precise and spatially regulated signaling gradients which permit highly regulated delivery of a substance of interest to a particular location of interest over very short distances (e.g. distances ranging from about 5 mm to about 125 mm, for example, about 5, 10, 15, 20, 25, 30, 35, 40, 45, 50, 55, 60, 65, 70, 75, 80, 85, 90, 95, 100, 105, 110, 115, 120, or 125 mm, or even greater). The incorporation of signaling gradients into the nerve guides of the invention addresses two critical issues concerning the processes that drive nerve regeneration. For example, growth factor gradients can be expected to accelerate axon elongation and growth along the axis of the bioactive gradient, an intervention that should greatly improve functional outcomes in nerve injury.

Accordingly, the present invention provides a simple and effective method to fabricate gradients of soluble materials and even cells into various tissue engineering constructs. This method incorporates various therapeutic reagents into dissolvable fibers and makes it possible to build very precise and spatially regulated gradients over very short linear distances. As an added advantage, the method makes it possible to fabricate gradients with virtually no loss of reagent during the fabrication of the device. While this particular description concentrates on a discussion of nerve guides designed for peripheral nerve regeneration, the use of highly precise growth factor gradients has applications in the treatment of injuries and diseases in the CNS and in other tissues and organs and in vascular construction.

There are two main types of gradients that can be generated using the methods of the invention. In one embodiment, the exemplary substance alginate is used as a carrier of therapeutic agents since this carbohydrate is largely inert and has been safely used as a carrier/delivery platform for a variety of materials. In the following discussion, methods using the exemplary carrier alginate are described. However, one of skill in the art will recognize that the description would apply to other types of carriers as well, except when reference is made to particular properties specific to alginate.

In the first technique, a constant concentration of carrier (e.g. alginate) is used to fabricate the entire length of a fiber and the concentration of the therapeutic reagent that is placed at specific intervals along the construct is varied. This design is referred to as a "Concentration Dependent Gradient" (CDG), since the concentration of the reagent varies along the length of the fiber. In the second technique, the concentration of carrier varies along the length of the thread and a constant concentration of therapeutic reagent is present along the entire thread. This type of construct is referred to as a "Dissolution Dependent Gradient" (DDG) because, release is regulated by the differential dissolution of the carrier, not by the concentration of agent, which is constant. In either design, the effective concentration of agent that is released from the thread is varied with precision.

In the fabrication of a CDG gradient, a stock solution of carrier (e.g. alginate) is prepared in nominally calcium free ddH$_2$0. The specific concentration of alginate varies as a function of the specific application under consideration. In some embodiments, a 10 mg/ml solution is used. A reagent of interest is mixed with the alginate stock solution at different concentrations. Specific concentrations will vary as a function of the type of gradient to be prepared and the nature of the reagent to be incorporated into that gradient (e.g. Pharmaceutical vs. growth factor etc.).

Figure 4:
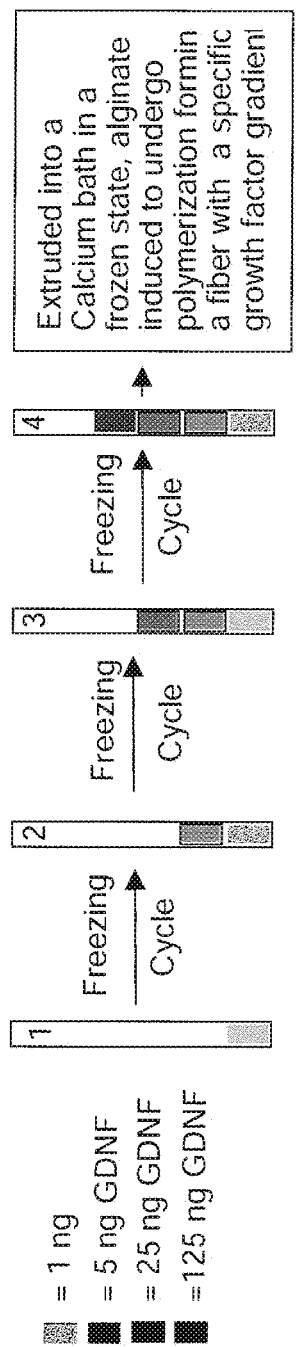
FIG. 4. Fabrication of a gradient thread. A defined quantity of growth factor is prepared in a series of alginate stock solutions. In this example, during step (1) a layer composed of 0.005 mg/ml alginate that contains 1 ng of growth factor has been added to the casting vessel. The aliquot is then frozen. In step (2) an aliquot prepared with 0.010 mg/ml alginate that has been supplemented with 5 ng GDNF has been added to the casting vessel on top of the frozen aliquot. The two are frozen and the cycle is continued until the construct is completed. In the final step, the frozen column of alginate is extruded into a calcium bath; this induces polymerization of the alginate into a continuous thread which is then used directly or dried.

Fabrication of a thread or fiber having varying concentrations of reagent (in this case, GDNF) is illustrated schematically in FIG. 4. To fabricate a CDG gradient an aliquot of alginate containing the reagent of interest at a specific concentration is added to a casting vessel or mold; for example, a small bore diameter tubing or a tuberculin syringe may be used, the diameter of which varies depending upon the fiber size that is needed. Initially, one discrete volume (aliquot) of liquid alginate containing a particular concentration of agent is placed into the vessel and frozen (1 of FIG. 4). After freezing, the next aliquot in the series (i.e.

the second volume of liquid alginate containing a second concentration of agent, which differs from the concentration of agent in the first aliquot) is added to the vessel (2 of FIG. 4) and the vessel and its contents are again frozen. These sequential cycles (i.e. the repetitive addition of liquid with a particular concentration of agent, followed by freezing) is continued until all desired different concentrations of agent have been added and frozen along the length of the mold. FIG. 4 illustrates 4 of such cycles. The addition of the liquid alginate solutions to the frozen aliquots in the casting vessel likely induces a very slight amount of melting in the frozen samples. This slight melting likely helps each section of the gradient to freeze into a solid continuous structure that undergoes polymerization into a thread, as follows: once the gradient is completed, the frozen alginate column is extruded from the casting vessel (e.g. using air or a plunger) and polymerization is induced, for example, by contact with calcium, e.g. via extrusion directly into a 2% calcium bath (typically at room temperature). Care is required so that the frozen alginate gradient does not melt prior to entering the calcium bath. Upon contact with the calcium bath, the frozen alginate begins to thaw and immediately or simultaneously polymerizes into a fiber or thread. This fiber is rinsed (e.g. in a 2% calcium bath supplemented with 5-10% propanol); dried; and then "cured" in a final rinse of, for example, hexafluorisopropanol (HFIP) to form a solid yet flexible fiber of alginate. Fabrication of a DDG gradient is carried out in a similar manner, except that each subsequent solution that is added contain a different concentration of carrier. In some segments, the concentration of the incorporated one or more agents may be zero, i.e. one or more of the agents may be absent from one or more of the segments of the thread.

The carrier threads are substantially cylindrical, and the final dimensions of the carrier thread are in the range of from about 5 mm to 125 mm in length (e.g. about 1, 5, 10, 15, 20, 25, 30, 35, 40, 45, 50, 55, 60, 65, 70, 75, 80, 85, 90, 95, 100, 105, 110, 115, 120, or 125 mm in length) and once completed and ready for implantation may be on the order of about 0.5 to 2.5-3.0 mm in diameter, and usually about 1-2 mm in diameter. Each carrier thread generally comprises at least two segments (e.g. segments A, B, . . . n, where n ranges from about 2 to about 100 (e.g. about 2, 3, 4, 5, 10, 15, 20, 25, 30, 35, 40, 45, 50, 55, 60, 65, 70, 75, 80, 85, 90, 95, or 100, or even more) and where each segment contains a different concentration of at least one substance of interest (e.g. a therapeutic agent, a polymerizeable polymer, etc.). However, single segment threads are also encompassed by the invention. The segments may be of equal or different lengths. For example, a 15 mm thread may include 3 to 5 segments containing distinct concentrations of a therapeutic substance, and each segment may be the same length along the longitudinal axis of the thread, or the lengths of individual segments (which may be determined by specific applications) may vary from one to another. Individual segments of a thread will generally range from about 0.5 mm to about 5 mm in length, i.e. about 0.25, 0.5, 0.75, 1, 1.5, 2, 2.5, 3, 3.5, 4, 4.5 or 5 mm, but may be longer e.g. up to about 10, 15, 20, 25 or 30 mm or more in length. In one embodiment, the carrier or gradient threads of the invention may be used in the nerve guides described herein. However, this need not always be the case. The carrier threads may be used for many other applications where it is desired to place a solid yet flexible, micro-sized biologically compatible gradient carrier, for example, to gradually release therapeutic agents within a relatively small, targeted area, e.g. within the brain, the eye, the heart, at or near the gums, etc. Other applications include the use of carrier materials cast in the form of sheets. Fabrication of gradient sheets of the invention is essentially the same as that of threads, except that the mold is wider in one dimension.

Threads may be prepared to direct the formation of blood vessels along a defined path, as for example in the heart where it may be desirable to "tissue engineer an artery in situ" to repair a blocked coronary artery. This may be accomplished by fabricating a gradient thread containing the appropriate signaling molecules and positioning it adjacent to an existing vessel. In essence the signaling gradient is designed to coax existing endothial cells to migrate along the gradient. The threads may also be combined within or adjacent to a small diameter (2-4 mm) PDS based cylindrical construct produced by electrospinning or other suitable method (e.g. extrusion and or casting). By laying track of PDS containing (or next to) the alginate signaling thread the formation of a blood vessel can be directed to form along a specific axis of orientation (e.g. see Example 6). Other polymers, including specifically, collagen, fibronectin and fibrinogen may be used in this application as well as other natural and synthetic polymers. In applications using PDS, the unique characteristics of PDS fibers are exploited, e.g. that they are generally 0.5-1.0 (but not restricted to) microns in average diameter, and that they promote the formation of capillaries and in some embodiments larger diameter blood vessels. The PDS cylinder can include various therapeutic agents or cells, e.g. it may be pre-seeded with stem cells, endothelial cells and/or other desirable cell types for use in this type of application.

Sheets of gradients can be used in treating larger scale injuries such as burns and other dermal injuries to promote skin regeneration. Gradients can be manufactured into these sheets such that the signals run from a low concentration along the edges of the sheet to a higher concentration in the middle. This type of gradient would be intended to promote and accelerate the migration of cells across the surface. This type of sheet might also be applied to transplanted (including by not restricted to the heart and kidney) or tissue engineered organs (liver, and bladder represent two candidate sites for this type of application) to promote nascent blood vessel formation and or differentiation of stem cells or engineered cells. The purpose of these constructs is deliver gradients over a surface that is too large to be effectively treated with gradient threads. Fabrication of gradient sheets of the invention is essentially the same as that of threads, except that the mold is wider in one dimension.

Gradients may also be used or for the targeted release of toxic substances within tumors; or other areas where an excessive cell proliferation or migration is undesirable. The gradient threads may be used for targeted slow release of substances of interest in any liquid environment in which the polymerized carrier will degrade or dissolve, thereby releasing (delivering) the entrapped substance(s) of interest (e.g. within the body of a bird or animal, within a plant, etc.), when one or more micro-sized carrier threads are placed or implanted at a targeted area of interest.

In the course of developing this technique, it was discovered that rinsing alginate constructs with HFIP greatly increases their stability in aqueous buffers. As a direct result, this increased stability also serves to drastically slow the overall release of agents such as functional growth factors from alginate based materials. For example, release can be detected up to and even beyond about 2 weeks. This is in contrast to conventional alginate systems, in which agent release is substantially complete within 3-4 days. Additional control over release kinetics can be achieved by adding such agents as heparin sulfate to the alginate, this specific factor is highly charged and binds peptides and other charged agents, thus slowing release.

After curing, the filament is ready for incorporation into a tissue engineering scaffold or other construct. As can be seen, this manufacturing method allows fabrication of specific gradients across very precisely defined spatial domains along the length of the fiber. In addition, upon hydration, the cured fiber is very flexible and does not swell appreciably, and thus is well suited to inclusion in the nerve guides of the invention. Typically, the cured alginate fiber is introduced into a nerve guide during the spinning process. A polymer is spun and induced to form a guide with a diameter of approximately 1 mm, the gradient threads are applied to the electrospun construct and the spinning process is resumed. In some embodiments, more than one thread per construct may be incorporated into the nerve guides, and, especially in the central nervous system, it may be desirable to have the gradients precisely positioned to more efficiently provide signals to specific cell populations. Also, the orientation of the gradient may be positioned in any direction (e.g. parallel with the long axis of the guide, at right angles to the long axis, or at an angle to the long axis), multiple threads of the same (or different) gradients may be placed in opposite directions or the same direction, etc. A gradient may be prepared such that the middle of the thread contains a high concentration of material or a low concentration of material. Individual segment lengths that make up the gradient threads that contain the different amounts of therapeutic reagents can be of equal length or of different unequal lengths (some short some long etc.) as determined from the specific conditions encountered in an injury bed. Alternatively, a uniform concentration of material may be desirable in some clinical applications. Any number of possible configurations can be produced with this method.

In some embodiments, the alginate threads may be processed at room temperature and not frozen. For example, this may be done when cells are to be incorporated into the fibers. Under these circumstances, the gradient may be produced by manipulating the viscosity of the carrier solutions. This can often be easily achieved by increasing the concentration of alginate or through the addition of other substances, e.g. sugars. By carefully preparing the gradient through the gentle addition of each subsequent aliquot, a gradient of material that has not been frozen can be prepared. The gradient is then polymerized by extrusion as described. We note that gradients can also be prepared by placing aliquots of material into a trough and adding polymerization agents to the trough. In this way, liquid (or frozen gradients) may be less disturbed during the polymerization step because extrusion is avoided. It is also clear that gradient fibers do not have to be exposed to drying prior to use and in some applications, for example those containing cells, it will be desirable to keep them in a hydrated state. Alginate threads are relatively stiff when dried; it may be desirable in some applications to incorporate plastizing agents (for example, PEG-polyethylene glycol) into these structures to adjust flexibility, e.g. to make them more flexible. In all of these embodiments, therapeutic agents incorporated into the alginate threads are released as the alginate dissolves.

Figure 5:
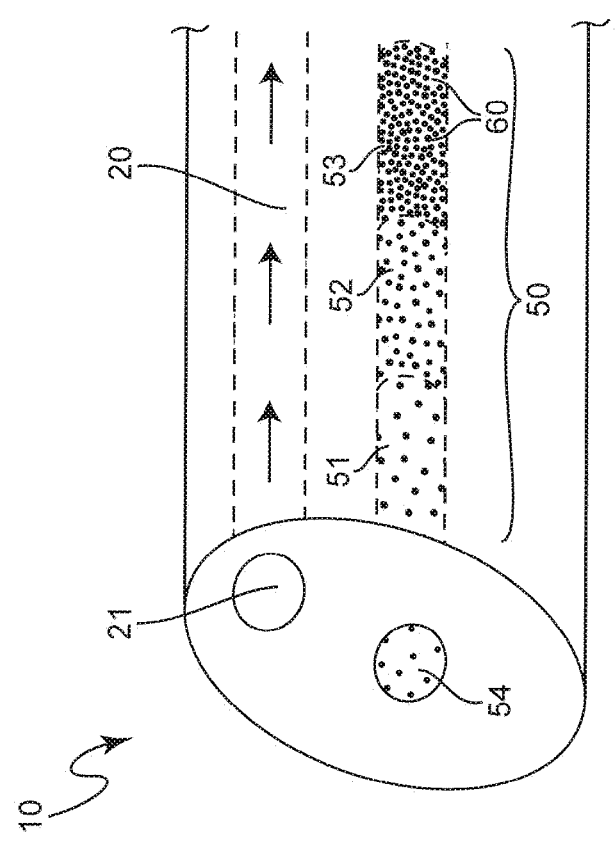
FIG. 5. Schematic representation of a nerve guide of the invention with a carrier thread containing a therapeutic agent disposed therein.

A schematic representation of a cross sectional view of an electrospun nerve guide with a carrier thread is presented in FIG. 5. As can be seen, this schematic contains a nerve guide 10 with one exemplary open channel 20 (not to scale as the channel would ordinarily be on the same size scale as the individual fibers that comprise the graft) with channel opening 21 at the surface of the cross section, and a centrally located carrier thread 50 with end 54 at the surface of the cross section (this fiber is also not drawn to scale). Carrier thread 50 is comprised of a plurality of contiguous yet distinct segments 51, 52 and 53, each of which contains a different concentration of active agent 60 therein (e.g. carrier thread 50 provides a step-gradient of active agent 60). With time, carrier thread 50 dissolves, releasing active agent 60 into the surrounding fibers of the guide (not shown, for the sake of clarity), and into open channel 20. As axons grow along open channel 20, they are exposed to active agent 60. Further, the concentration of active agent 60 will be greater in the vicinity of segment 53, which has a relatively high concentration of active agent 60, than in the vicinity of segment 51, which has a relatively low concentration. Such differences in the concentration of an active agent may be used to modulate axonal growth. For example, in this illustration, if the active agent is a growth factor, the growth rate of the axons would be more rapid (would accelerate) as they progress through the guide and encounter the higher concentrations of active agent near the distal end of the guide.

The advantage of this type of structure is that the threads of alginate can be laid directly into the forming fiber arrays of a nerve guide. For spinal cord reconstruction it is possible to place the fibers in specific sites to direct the reconstitution of normal spinal cord topography. In the spinal cord axons originating above an injury as well as below an injury must grow across the injury site (i.e. two way traffic in effect). The alginate threads make it possible to produce gradients over very short distances (e.g. less than 100 mm) and in a manner that can be optimized for axons growing up or down across the injury site. For example growth factor A (or pharmaceutical reagent) may be required in a gradient that runs from below and injury to above the injury, growth factor B (or pharmaceutical reagent) may need to be in a gradient that runs from above the injury to below the injury. To achieve this the gradient threads are prepared and placed in appropriate orientation. It should be emphasize that these gradients can be produced and customized to specific injuries over the relative short distances (<1-2 mm, 2-5 mm, 5-10 mm, 10-30 mm, and >30-100 mm) that may be encountered in an injury in the spinal cord or in the peripheral nervous system.

Also, while in addition to signaling and pharmaceutical gradients, it is also possible to incorporate various other proteins such as extracellular matrix (ECM) proteins or specific peptide factors like RGD (i.e. the Arg-Gly-Asp peptide, the activity binding moiety for many cell surface receptors) in gradients into these threads. By doing so as the thread begins to break down that incorporated ECM proteins are released in a gradient fashion and become attached to the fibers in the immediate vicinity. In this was a gradient of binding elements on the fibers can be produced to enhance cell migration and or axon elongation down the protein gradient. Cells will grow along a binding gradient in preferential fashion from a low concentration of ECM protein to high concentration (or density) of ECM protein. This provides yet another way to provide guidance cues to cells to direct them to grow down the elongated pore spaces present in the nerve guides.

Variations in the construction of carrier threads may be made so as to tailor the threads to particular purposes and/or to improve the results that are obtained. For example, more than one substance may be prepared in a given gradient thread, and the gradients of these multiple substances may be uniquely tailored and may be uniquely different from one anther or even running in completely opposite directions. In another example, the release kinetics of alginate threads can also be modulated by coating the exterior of the threads with various materials including such biodegradable polymers as PGA, PLA, PDS or other suitable polymers to slow the breakdown of the alginate and or to increase the material strength of the construct. The surface of the carrier fiber can be modified by electro spraying or electrospinning various natural and or synthetic polymers onto the surface of the structure. This provides far more subtle control over the structure of the construct than simply dipping the material into a polymer bath. Multiple reagents can be added to single alginate thread in any number of different configurations and concentrations. Some may be placed into the fiber as a gradient, while others may be present at a continuous concentration, or even just at one specific site in the fiber (e.g. one of the ends or in a middle position). Further, multiple fibers containing identical or different doses or gradients of materials might be used to fabricate a construct. For example, by electrospinning a cylindrical construct and positioning alginate fibers in specific positions within the scaffold, it is possible to deliver specific factors to different sections of the guide in a highly precise manner.

In one embodiment, alginate is used in the fabrication of carrier threads. Reasons for this include that alginate is water soluble and thus easy to work with, is relatively non-toxic, and dissolves or is absorbed slowly by the body in a manner that can be controlled by adjusting the concentration. However, those of skill in the art will recognize that other substances may be used to fabricate the carrier threads, examples of which include but are not limited to various carbohydrates, proteins such as the ECM proteins of the collagen family, fibronectin, fibrinogen, intracellular proteins such as actin, and or synthetic materials such as hydrogels and other biocompatiable polymers (e.g. PDS, PEO, PGA, PLA, PGA/PLA copolymers and others listed herein). As an example, PDS can be dissolved in HFIP and mixed with varying amounts of therapeutic agents and extruded and allowed to dry to produce a fiber, using methods much like those used in the production of sutures and fishing line. Therapeutic agents/substances/reagents that may be incorporated into the carrier threads of the invention include but are not limited to anesthetics, hypnotics, sedatives, sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmondics, appetite suppressants, neuroactive substances, neurotransmitter agonists, antagonists, receptor blockers, reuptake modulators, beta-adrenergic blockers, calcium channel blockers, disulfarim, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists, hormone antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, anti-inflammatories, wound care products, antithrombogenic agents, antitumoral agents, antithrombogenic agents, antiangiogenic agents, antigenic agents, wound healing agents, plant extracts, growth factors, growth hormones, cytokines, immunoglobulins, osteoblasts, myoblasts, neuroblasts, fibroblasts, glioblasts; germ cells, hepatocytes, chondrocytes, keratinocytes, smooth muscle cells, cardiac muscle cells, connective tissue cells, epithelial cells, endothelial cells, hormone-secreting cells, neurons, emollients, humectants, anti-rejection drugs, spermicides, conditioners, antibacterial agents, antifungal agents, antiviral agents, antibiotics, tranquilizers, cholesterol-reducing drugs, antitussives, histamine-blocking drugs and monoamine oxidase inhibitor, nucleic acids such as DNA, RNA (e.g. siRNA), etc.

Release of agent from the carrier thread generally occurs over a period of time ranging from at least about 1 hr to about 35 days, and usually from at least about 1 day to about 21 days. However, the use of coating and our alternative polymers in the fabrication of the threads can be used to modulate these intervals to shorter and longer times.

In one embodiment, the carrier of therapeutic substances is a thread or fiber, it is also possible to use a modified form of this fabrication method to produce beads, disks, sheets, or other shapes of the carrier containing reagents. These disks might be placed in various places to provide local reagent delivery. For example, disks might be prepared and applied on or into the brain. This would make it possible to deliver various reagents over a prolonged period of time from a position behind the blood brain barrier (many therapeutic reagents can not pass this barrier to reach the brain or other components of the CNS). To fabricate a disk a reagent of interest is mixed with a specific carrier (e.g. alginate) concentration. The supplemented alginate is dropped into a calcium bath to induce polymerization as described; the resulting bead is gently compressed and then frozen. This produces a thin disk of alginate supplemented with the reagent of choice. The size and final shape of the bead can be regulated by the volume of alginate used to prepare the bead and/or by using different surfaces with varying hydrophobic properties. In addition, such structures could be layered and or coated as described for the alginate fibers to differentially delivery different or the same reagents.

In yet other embodiments, very long term release kinetics (e.g. for periods of time ranging from about 35 days to about 1 year can be achieved by encapsulating various agents of interest (e.g. therapeutic materials) into microbeads ("microcarriers", e.g. of alginate or some other suitable substance) using electro spray technology; and, optionally, incorporating the microbeads into a carrier thread. This treatment sequesters the reagent of interest within the microbead and away from the harmful effects of organic solvents. The beads are then be mixed with another slowly degrading polymer, for example typically biocompatible polymers could include PCL, PDS, PLA, PGA and or copolymers of PGA, PLA and or other polymers. The mixture is then extruded to produce a carrier thread or fiber containing the alginate microcarriers and the encapsulated materials, which are effectively immobilized within the microbeads. As the polymer fiber breaks down the incorporated alginate microcarriers are exposed and begin to breakdown, releasing the reagent. A similar approach could be used to produce disks and or other shapes that are tailored to specific applications, e.g. for use in the nerve guides of the invention, or for other purposes. See FIG. 18 and the figure legend for one method of producing micro carrier beads by electrospray.

The invention further provides methods for guiding or facilitating the regenerative growth of severed or truncated nerves in a patient in need thereof. The method involves attaching (e.g. suturing) a first end surface of a nerve guide of the invention to the proximal end of a severed nerve and attaching a second end of the nerve guide to the distal end of the severed nerve. In other words, in the peripheral nervous system, the guide is interposed between the two nerve stumps and is used to bridge the gaps between the two. In the process of joining the nerve ends to the guide, the guide and nerve ending may be moved or manipulated in order to achieve a suitable orientation of all three entities, within the limits imposed by the length of the gap between the ends of the nerve. Since the natural tendency is for the proximal nerve end to begin to regenerate, when this end is attached to the guide, the regenerating tissue will encounter the guide and be able to preferentially grow only into the void space of the guide, i.e. into the open channels, since the rest of the space is filled with the fibers which make up the guide. In order to insure proper entry of the regenerating axons into the guide, the nerve stumps are sutured or otherwise attached to the guide a closely as possible, and may even be partially inserted into the guide. In spinal cord injuries axons will grow into the guides from both ends as there are ascending and descending axons in the central nervous system. In these injuries it is unlikely the guides will be sutured in place, rather they may be glued or held in place by the surrounding tissue so as not to disrupt the regeneration process.

The nerves that are regenerated in the peripheral nervous system using the methods of the invention are generally peripheral nerves, examples of which include but are not limited to sciatic nerve at its terminal branches including the sural branches and the tibial, common fibular, superficial and deep fibular, and plantar nerves. The femoral nerve including motor and sensory subdivisions. The roots, divisions and terminal nerves of the brachial plexus, this includes the major divisions such as the musculotaneous, median, ulnar and radial nerves, and the axial nerve. Also included are more distal branches including the anterior interosseus and posterior interosseus, the ulnar recurrent deep and superficial radial, and other named and un-named terminal branches. In the central nervous system potential repair sites include the spinal cord proper and nerves of the cauda equine and nerve rootlets exiting the spinal canal. Generally, for the methods of the invention to be suitable for use, the nerve will have been injured in some manner, e.g. severed, partially severed, crushed, or otherwise damages so that the integrity of the nerve is compromised. The injury is usually accidental, but may also occur as the result of another necessary procedure, e.g. a surgical procedure.

The subjects in whom the nerve guides of the invention are used are generally mammals, although this need not always be the case. The mammals are generally humans, but this also need not always be the case as veterinary used are also contemplated.

EXAMPLES

Example 1

An ideal nerve guide configuration would closely mimic the structure of an autologous nerve graft. This idealized guide would display a cylindrical shape and be composed of dense three dimensional (3D) arrays of highly aligned electrospun fibers that were oriented in parallel with the long axis of the construct. Gaps and elongated spaces between the stacked fiber arrays would provide thousands of channels for directed axonal growth. This type of configuration can be approximated by rolling a 2D sheet of aligned fibers into a cylinder. Unfortunately, rolling a 2D sheet will result in a seam in the construct that could provide an avenue for the infiltration and penetration of inflammatory and interstitial cells into the construct. The seam could also represent a nexus for mechanical failure. Air gap electrospinning makes it possible to circumvent these limitations and produce cylindrical, seamless, and truly, 3D constructs composed of aligned arrays of electrospun fibers that are oriented in parallel with the long axis of the cylindrical construct.

In this study, we characterize the air gap electrospinning process and examine how this fabrication technique can be exploited to produce nerve guides that facilitate the regeneration of peripheral nerve fibers. Poly-ε-caprolactone (PCL) was chosen as the polymer for the manufacture of the nerve guide due to its slow rate of degradation [19], thus it can act as a guide for the new axons throughout the nerve regeneration process. PCL was electrospun at varying concentrations for in vitro testing to determine the most appropriate air gap electrospinning variables for the manufacture of constructs suitable for directing the axons in peripheral nerve injuries.

Methods

Electrospinning.

PCL (Sigma: PCL 65,000 M.W.) was dissolved in trifluoroethanol (TFE) at various concentrations, including 50, 75, 100, 125, 150, 175, 200, 225, 250 and 275 mg/ml. Solutions were loaded into a 10 ml syringe that was capped with an 18 gauge blunt-tipped needle. Conductive, circular washers of varying diameters were placed over the blunt tipped needle; several different electrospinning configurations were tested at each concentration of PCL.

The air gap electrospinning system used in this study consists of two vertical piers grounded to a common voltage, typically set to −4.0 to −16.0 kV (FIG. 6, point A). From each vertical pier an additional set of horizontal piers project inwards at 90° with respect to the upright piers (FIG. 6, point B). A gap (which can be adjusted from about 1-6 inches) separates the terminal ends of these projecting piers.

Figure 6A:
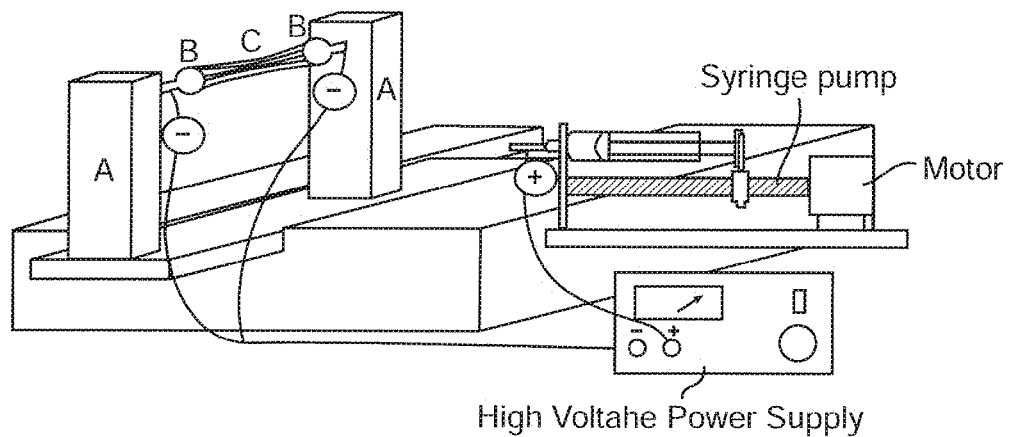
FIG. 6A-B. A, Schematic of the ground targets used in a dynamic two pole air gap electrospinning system. Vertical, hollow piers A transmit ground wires to horizontal piers B that project inward towards one another (in this depiction the ground wires are depicted on the outside of the vertical piers to emphasize that both poles are grounded to a common ground). Fibers C accumulate across the gap that separates the two horizontal piers. By rotating the targets depicted as B in this diagram in unison using a single motor or a plurality of motors that are synchronized the target poles (B) can be slowly rotated to collect fibers in a far more uniform fashion than can be achieved with a static system (see FIG. 6B). The position of the syringe and electrospinning source are relatively arbitrary and largely dependent upon the cabinet used for electroprocessing. For example, the electrospinning source may be positioned parallel to the base of the ground device and at a height that corresponded to the height of the grounded horizontal piers B; B, close-up of the section of the apparatus where the fiber array is formed (as depicted in FIG. 6A). It is also clear that multiple source solutions positioned in different orientations can be used in this type of system. Typically at least two power supplies are used in the air gap process. The polarity of the air gap systems depicted in these figures is arbitrary and may need to be reversed for certain polymers. This configuration describes the conditions specific to PCL. It may also possible to use alternating currents and or to use a DC current that is designed to flash between the two poles back and forth in (e.g. right to left right to left) in a timing pattern that matches fiber deposition as a way to even further increase alignment and provide even finer control over the process. B, Schematic of a static air gap target array. The static system displayed in this figure was used to define the electrospinning conditions necessary to produce the seamless nerve guides and is suitable for the fabrication of guides less than about 10 mm in diameter. For larger structures the dynamic system illustrated in FIG. 6A allows for the collection of fibers in a more uniform pattern on the "back side" of the graft. However, even this type of static system can be modified to increase the diameter of constructs beyond about 10 mm by using a second (or more) electrospinning source to deposit fibers on the different surfaces. Also of note, if the electrospinning ground and or target balls (at the end of the inwardly projecting piers in FIG. 6B) are manipulated it may be possible to produce (1) structures that gradually taper from one end to the other. In addition, the diameter of the balls used to collect the fiber (again depicted in FIG. 6B) represents a critical process variable. To produce a 10 mm (or less) diameter construct, a 5 mm diameter ball is used. Without this terminal ball (or equivalent terminal end, e.g. a ball cut in half, a pyramidal shape a cone shape etc.) the electrospinning stream will pass as a continuous straight jet between the target balls and fail to collect across the gap to produce a nerve guide. With the balls in place, the charged electrospinning stream passes as a series of ever increasing concentric spiraling rings that result in the deposition of fibers across the target array. In a similar fashion if the steel washer is not used on the electrospinning needle, the charged polymer jet leaves the syringe as an unexpectedly long and straight, elongated jet that passes between the target array gap, and once the jet passes beyond the target it becomes unstable and disintegrates and fibers fail to accumulate on the target. The diameter of the balls is also critical to the process as described. If they are increased to 10 mm in diameter or greater, a hollow cylinder that is composed of longitudinally arrayed fibers (arrayed along the long axis) forms rather than the solid cylinders disclosed herein (i.e. which are suitable for use as nerve guides). This type of structure may be useful in the production of some tissue engineering products like blood vessels. One skilled in the art would recognize that alternating air gap spinning with conventional spinning conditions could be used to produce structures that have alternating layers of longitudinally arrayed, radial, random and circumferentially arrayed fibers. This type of structure would impart unique biological and or mechanical properties to the construct.
Figure 6B:
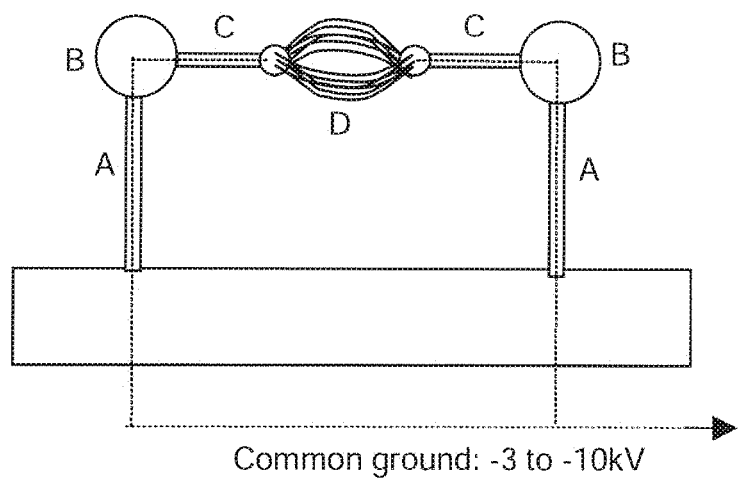

FIG. 6B shows a close-up view of the part of the apparatus wherein the nerve guide is formed. This figure illustrates a simple set-up to produce cylindrical semi-solid nerve guides composed of 3D fibers arrays. More sophisticated systems can be fabricated that use rotating targets, but in this simple example the target arrays is static. This system uses 2 grounded targets. This static (no rotation of targets) system is constructed of 2 parallel vertical piers (A of FIG. 6B) grounded to a common voltage (−3 to −10 kV). Each pier is capped with a (grounded and insulated) metal sphere (B of FIG. 6B), from each grounded sphere additional (grounded and also insulated) metal piers project inward at 90° with respect to the upright piers inwards towards one another (C of FIG. 6B). The inwardly projective piers are capped with small metal (non-insulated but grounded) targets, these intensify the electric field. An "air" gap (adjustable from about 2-6 inches) separates the terminal ends of these projecting target piers. The electrospinning stream is directed into the air gap separating the grounded piers. As the charged polymer stream reaches the target it is laid out in a series of loops that pass back and forth between the terminal portions of the grounded piers and collects as a parallel array of fibers (D of FIG. 6B). The elliptical nature of the fibers illustrated in the schematic are greatly exaggerated, in reality of the fibers are deposited in a nearly linear cylindrical bundle. Air gap electrospinning is very effective at inducing the alignment in small diameter fibers, which can range from <200 nm to several microns in average cross sectional diameter, and depositing them into macroscopic structures (up to at least 10 mm in diameter) 3D cylindrical arrays. The densely packed and highly aligned fibers of the 3D nerve guide of the invention that are produced in this manner resemble the anisotropic structure present within an autologous nerve graft. The fibers are arrayed in parallel with the long axis of the constructs and in cross section, these cylindrical scaffolds exhibit dense bundles of fibers Alignment in conventional electrospinning systems can be highly dependent upon fiber diameter (14, 15)

In this Example, electrospinning solutions were charged to +22 kV and directed into the gap separating the grounded horizontal piers. Polymer solutions were metered into the air gap system using a syringe driver with rates of delivery varying from 2-20 ml/hour (see Table 1 for specific conditions). The distance between the solution reservoir and ground target array was varied from 10 cm to 30 cm. Once the charged electrospinning jet forms in this type of spinning, the polymer stream reaches the target and is laid out in a series of loops that pass back and forth between the terminal portions of the grounded piers, resulting in the formation of a bundle of parallel fiber arrays (FIG. 6A, point C). Conditions for electrospinning at each PCL concentration were optimized to maximize fiber formation and collection onto the mandrel. The electrospinning conditions disclosed in Table 2 are optimized to the specific laboratory environment (e.g., 68° F. with approximately 40% humidity) and electrospinning cabinet. Adjustments may be necessary to account for varying ambient conditions and different polymers.

TABLE 2

Summary of specific electrospinning conditions for PCL in the two pole electrospinning system. With increasing PCL concentration the target voltages, the electrospinning distance between the syringe reservoir and target as well as the distance between the poles of the air gap system must be reduced in order to induce fiber deposition across the poles.

| Starting Concentration in TFE (mg/ml) | Washer diameter (mm) | Solution Voltage (kV) | Ground voltage (kV) | Polymer rate (ml/hr) | Spinning gap (cm) | Ground target gap (cm) |
|---|---|---|---|---|---|---|
| 50  | 19 | +20 | −16    | 9  | 25 | 5 |
| 75  | 19 | +20 | −16    | 10 | 25 | 6 |
| 100 | 19 | +20 | −20    | 15 | 25 | 6 |
| 125 | 19 | +20 | −10-12 | 15 | 25 | 6 |
| 150 | 19 | +20 | −7     | 12 | 21 | 6 |
| 175 | 23 | +20 | −7     | 10 | 18 | 6 |
| 200 | 23 | +20 | −7     | 10 | 18 | 6 |
| 225 | 32 | +20 | −7     | 12 | 16 | 5 |
| 250 | 32 | +20 | −5     | 10 | 15 | 5 |
| 275 | 19 | +20 | −3     | 8  | 13 | 5 |

Routine Scanning Electron Microscopy (SEM).

A Zeiss EVO XVP scanning electron microscope equipped with digital acquisition was used for image capture. Electrospun constructs were removed from the target and cut into 3 sections of equal length. Each of the 3 segments was mounted onto a scanning electron microscope stud and sputter coated. Average fiber diameter was determined from N=3-5 SEM images captured at magnifications ranging from 450-5000× from each of the 3 sections using the NIH ImageTool software [17].

Fiber Alignment Analysis.

Using the digital SEM images captured for fiber diameter analysis, the relative degree of fiber alignment was measured in each guide segment using the NIH ImageJ 2D fast Fourier transform (2D FFT) function [14,20]. By using the 2D FFT approach an alignment plot can be generated. The height of the resulting peaks, read from the Y axis, reports the degree of orientation in the data image. The position of the peaks on the X axis reports the principal angle of fiber orientation [14,20]. The FFT alignment data was normalized to the lateral edges of the cylindrical constructs which were arbitrarily assigned a value of 900 on the unit circle. The relative degree of fiber alignment and the principal angle of fiber orientation were determined for each of the construct formulations using the 2D FFT method.

Materials Testing & Physical Properties.

Materials strength was measured by uniaxially testing the constructs to failure at an extension rate of 100 mm/min using a Bionix 200 Mechanical Testing Systems instrument (MTS Systems Corp., Eden Prairie, Minn.). Cylindrical electrospun samples were prepared from variable concentrations of PCL (100, 150, 200 and 250 mg/ml; N=4-6). Testing the material properties of an electrospun sample is typically done with a flat sheet of material, whereas our constructs are cylindrical in nature. To address this limitation, we elected to flatten the scaffolds and then cut out "dog-bone" shapes using a die punch (2.67 mm wide, gauge length of 0.295 mm). This approach, at least, allows us to use a configuration that controls for grip and geometry effects to evaluate how fiber diameter in each of our scaffolds contributes to their material properties. Specimen thickness was estimated using a Mitutoyo IP54 digital micrometer (Mitutoyo American Corp., Aurora, Ill.). In this study, stress at failure for these scaffolds is reported [15]. Data sets were screened by one-way analysis of variance (ANOVA; $p<0.01$).

The physical properties of the scaffolds were quantified in terms of their overall void space. Cylindrical electrospun samples prepared from variable concentrations of PCL (100, 150, 200 and 250 mg/ml; N=4-6) were tested using the liquid intrusion method of Pham et. al [21]. Scaffolds were electrospun, put under vacuum for 10 minutes and weighed (W1). Then, they were soaked in 90% ethanol for 10 minutes for initial hydration, and subsequently in distilled water for 30 minutes. Hydrated scaffolds were weighed (W2). The void space was calculated by dividing the volume of intruded water (as determined by the change in mass due to intrusion of water having density of 1 g/ml) by the total volume after intrusion.

$$\text{Percent Void Space} = \frac{W2 - W1}{W2} \times 100$$

Data sets were screened by Student-Newman-Keuls multiple pairwise comparison; $p<0.05$.

Cell Culture.

Dorsal root ganglion (DRG) explants were prepared from embryonic day 15 rats as described previously [22,23]. PCL scaffolds for cell culture experiments were prepared from representative starting concentrations (125, 200, and 250 mg/ml). Scaffolds were soaked in 100% ethanol overnight, then rinsed in 70% ethanol, and then rinsed 3× in sterile Phosphate buffered saline (PBS). A 25 gauge needle was used to prepare an opening into the dorsal surface of each scaffold, and a single DRG was inserted into the resulting cavity. DRG explants were maintained for 7-10 days in media supplemented with 0.1 μg/ml NGF. Media was exchanged every other day.

Immunofluorescence Microscopy: DRG Explants.

DRG explants were rinsed in PBS and fixed in 4% paraformaldehyde prepared in PBS. Samples were extracted in 0.1% triton and immunostained with the neuron specific marker TuJ1 (Tubulin J1: MMS-435P, Covance, 1:500). Antibodies were diluted in PBS supplemented with 1% BSA and incubated with all samples overnight at 40 C. Scaffolds were rinsed and counterstained with Goat anti-mouse antibodies conjugated with Texas Red (1:200). All samples were stained with DAPI to reveal nuclei. A Nikon TE300 microscope equipped with a 10× objective and a DXM 1200 digital camera was used to capture images at a pixel resolution of 3840×3072. Individual images of the DRG explants were assembled into montages using Adobe Photoshop software.

Electrospinning for In Vivo Experimentation.

For implant studies, nerve guides were electrospun from a starting concentration of 200 mg/ml PCL using optimized conditions (Table 2). To reduce inflammatory cell infiltration into the fiber arrays of the guide, an exterior coating of PGA:PLA (50:50) copolymer was electro-sprayed (100 mg/ml in TFE) onto the outside of the completed constructs. This was achieved by placing a circular, 120 mm diameter steel plate directly behind the completed nerve guide. To process the PGA/PLA copolymer an alligator clip was attached to the electrospinning source syringe (no washer was used) and charged to +22 kV, the steel plate was charged to −2 kV for collection. By placing the completed nerve guide between the electrospinning source solution and the grounded steel plate, the fibers of PGA/PLA copolymer deposit on the surface of the nerve guide construct, forming a barrier that is designed to limit the penetration of interstitial cells into the reconstructed nerve in vivo [17].

Surgery.

All surgical and postoperative care procedures were performed in accordance with the Virginia Commonwealth University Institutional Animal Care and Use Committee. Nerve guides were prepared from starting concentrations of 200 mg/ml for preliminary implant studies. Adult (70-90 day) Long Evans Hooded rats (N=3) were intubated and brought to a surgical plane with 2.5% isoflurane. Body temperature was kept normothermic using a homeothermic blanket. Hair was removed from the hindquarters, skin was swabbed with betadine. Using sterile techniques, skin and muscle overlaying the sciatic nerve were mobilized, and a 10 mm segment of the nerve was excised. This interval represents a critical threshold in short term regeneration experiments that can be used to characterize the efficacy of a candidate guide in the rodent model. Electrospun nerve guides were sutured to the distal and proximal stumps of the injured tissue using 10-0 nylon sutures (Ethicon, Inc. USA). At the conclusion of surgery, skin incisions were stapled and the animals were allowed to recover on a warming pad. After surgery all animals were given free access to food and water and housed 2 per cage. Analgesic medication (Tylenol oral suspension, 2 mg/ml) was mixed into the drinking water and administered for the first 3 days post surgery. After 7 weeks, animals were sacrificed with a lethal dose of pentobarbital (Sigma-Aldrich, St Louis, Mo.), and the nerve implants were harvested for microscopic analysis.

Immunofluorescence Microscopy Implanted Nerve Guides.

Tissue was immersed for 2 hr in 4% paraformaldehyde prepared in PBS at room temperature and then incubated overnight in 30% sucrose prepared in PBS at 4° C. The samples were frozen and cut into 30 µm thick sections for staining. Primary antibodies including, S100 (Schwann cell marker, Dako, Denmark, 1:500), MBP (Myelin basic protein, SMI-99, Covance, 1:1000), and NF-68 (Neurofilament 68, Sigma, 1:1500) were incubated on the sections overnight at 4° C. Samples were rinsed in PBS-triton and counterstained with secondary antibodies (Invitrogen or Alexis) for 60 minutes at room temperature. DAPI was used to image the nuclei.

Electron Microscopy.

Tissue was recovered and immersed in 2% glutaraldehyde plus 2% paraformaldehyde for 12 hr at 40 C and post fixed in 1.0% osmium plus 2.5% potassium ferricyanide. Samples were subjected to a graded series of dehydration and embedded in Poly/Bed (Polysciences). It is difficult to get good plastic infiltration into the dense matrix of an electrospun scaffold that has been densely populated by cells; air bubbles are often trapped and interfere with subsequent processing. To overcome this limitation, samples are placed under a vacuum during the final infiltration step. The sections were stained with toluidine blue/crystal violet and imaged on a Nikon TE300 microscope. All images were captured and stored in TIFF format.

To determine the total number of axons passing through the implants, a montage of the complete cross sectional area of the graft was prepared from images captured with 10× brightfield objective lens and a Nikon TE300 microscope. The images were imported into the NIH ImageTool to measure the area encompassed by the fibrotic capsule (induced by the PGA/PLA coating). Total axon number was determined for a series of images captured at systematic intervals throughout the nerve cross section using a 100× oil immersion lens. Each raw data image covered an area of 125 µm×125 µm and was subdivided into a series of 25 µm×25 µm grid squares. The number of myelinated axons present in each data image was determined by non-bias sampling methods. To extrapolate the total number of axons present in the cross sectional area, the density of myelinated axons in the sampled images was multiplied by the total cross sectional area of the grafts. Data images used to determine myelinated axon number were used to determine individual axonal cross sectional areas using NIH ImageTool. All measurements were calibrated with a stage micrometer.

Results

Electrospinning Characteristics and Fiber Properties:

The discussion concerning fiber properties is subdivided into three sections based on starting conditions and electrospinning characteristics. Overall, the average fiber diameter of the scaffolds produced varied as a function of the starting conditions.

Starting Solutions 50-100 mg/ml.

Figure 7A:
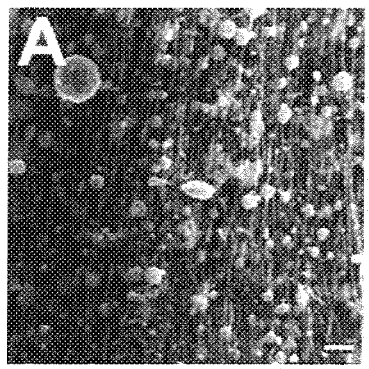
FIG. 7A-J. Representative Scanning Electron Micrographs (SEM). Panel A. SEM of scaffolds produced from 50 mg/ml starting concentrations using air gap electrospinning. Note that even heavily beaded scaffolds exhibit aligned fibers. Scaffolds produced from D=75 mg/ml, E=100 mg/ml, F=125 mg/ml, G=150 mg/ml, H=175 mg/ml, I=200 mg/ml, J=225 mg/ml, K=250 mg/ml, L=275 mg/ml. All images captured at 1000× magnification. Scale in J for A-J=20 μm.
Figure 7B:
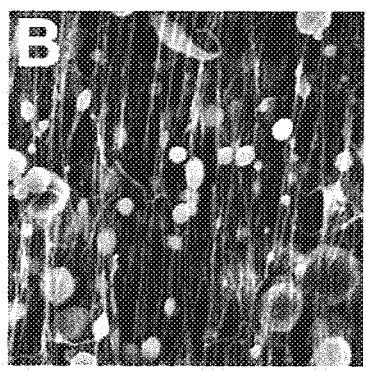
Figure 7C:
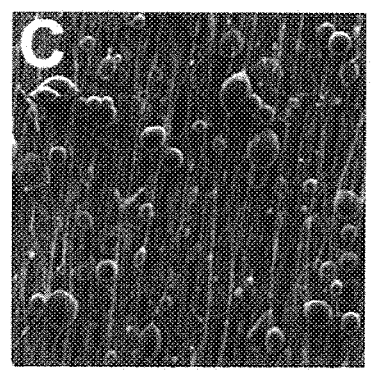
Figure 7D:
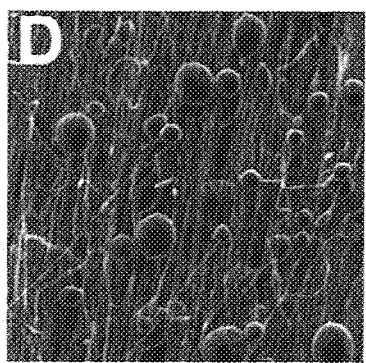
Figure 7E:
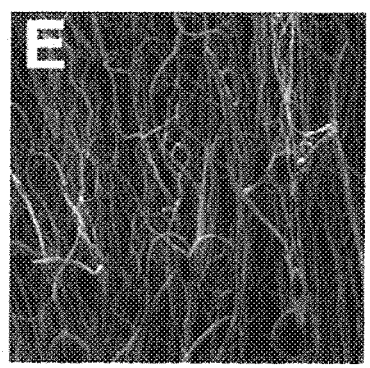
Figure 7F:
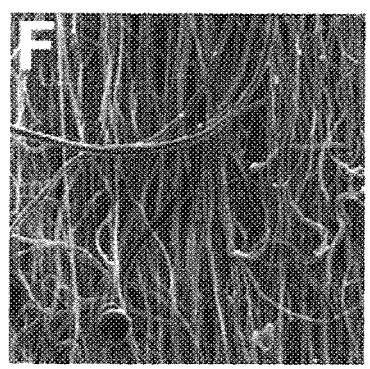
Figure 7G:
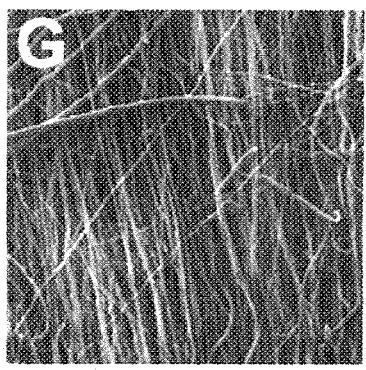
Figure 7H:
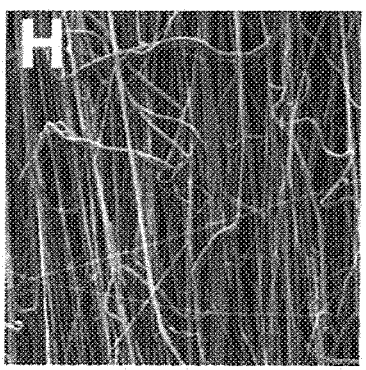
Figure 7I:
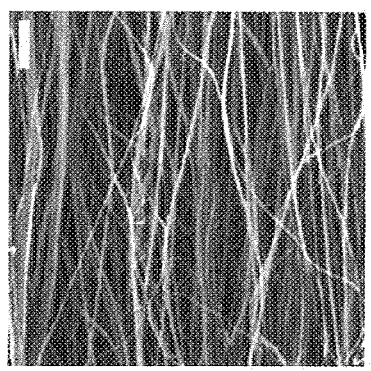
Figure 7J:
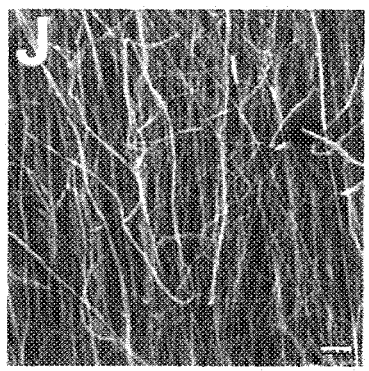

At concentrations ranging from 50 to 100 mg/ml PCL, there was nominal to poor fiber formation and fiber collection. Fibers appeared to coalesce out of an amorphous cloud of material that collected in the vicinity of the target grounds. These scaffolds exhibited extensive beading; these beads were interconnected with an array of small diameter fibers that were oriented in parallel with the long axis of the cylindrical scaffolds (FIG. 7A-C). Macroscopically, these cylindrical constructs were predominately composed of aligned elements.

Beaded structures can form in an electrospinning field as a consequence of Rayleigh instabilities that develop in the charged jet as a result of: (A) inadequate flow rates of the electrospinning solution; (B) electric field effects; (C) inadequate polymer chain entanglements in the solvated spinning solution and; (D) too low of a starting polymer concentration [24]. Increasing the flow rate of the polymer solution into the electric field did not suppress bead formation in these scaffolds. Instead, the increased flow rate resulted in the accumulation of a dense cloud of solvent in the vicinity of the target which prevented fibers from forming altogether. Nor was the formation of the beaded structures visibly altered by directly altering the potential of the electric field, manipulating the distance between the syringe reservoir and ground targets, or by changing the diameter of the washer used to direct the charged electrospinning jet at the bi-polar target (key elements of specific electrospinning conditions are summarized in Table 2). Given these results it is clear that a 50 mg/ml starting solution represents the near absolute minimal threshold concentration for fiber formation to take place in this particular air gap electrospinning system.

Starting Solutions 125-200 mg/ml.

Over this range of starting concentrations average fiber diameter increased and was more heterogeneous with respect to the fibers electrospun from the 50-275 mg/ml solutions (FIG. 8B). As the starting PCL concentration was increased beyond 125 mg/ml the beaded structures present in scaffolds produced from the lower starting concentrations became increasingly less apparent (FIG. 7E-J). Average fiber diameter in scaffolds produced from the 125 mg/ml solutions was 382 nm, these fibers ranged from 90 nm to 1.3 µm in cross sectional diameter. Scaffolds produced from the 200 mg/ml solutions had an average fiber diameter of 906 nm with a range of 60 nm to more than 5.1 µm in average cross-sectional diameter.

The visible components of the electrospinning field changed dramatically over this range of starting concentrations. At 125 mg/ml, the charged electrospinning jet was distinct and composed of a continuous jet of material that emanated from the syringe tip; this jet was several centimeters in length. As the charged jet approached the targets it became unstable and fibers appeared to form out of an amorphous cloud of material. As the starting concentration was increased to 150-200 mg/ml the charged jet appeared as a distinct series of spiraling loops that originated from a prominent Taylor cone. The appearance of this stable jet coincided with a marked reduction in bead formation, a physical property indicating that sufficient polymer chain entanglements are present in the solvated spinning solution to suppress the Rayleigh instabilities observed at lower polymer concentrations. The spiraling jet of material was directed towards the gap between the two poles of the air gap system. Fibers formed in the immediate vicinity of the grounded piers and were visibly collected across the gap separating the two grounded targets. As additional fibers collected across the targets, the pre-existing fibers collapsed into a much more compact cylindrical structure. With the formation of the spiraling jet of charged material it was necessary to reduce the distance between the electrospinning source reservoir (syringe) and the grounded targets (Table 2). Fiber deposition was optimized when the apparent diameter of the spiraling jet coincided with the distance between the piers of the bi-polar ground. Under these conditions fibers were observed to rapidly accrue on the ground targets.

Starting Solutions 225-275 mg/ml.

The relationships between the starting solution properties and final fiber properties was less well defined in scaffolds produced from starting concentrations greater than 200 mg/ml (FIG. 8B). Scaffolds spun from the 225, 250, and 275 mg/ml solutions exhibited marked heterogeneity in fiber size (FIGS. 7H-J and FIG. 6). For example, scaffolds produced from the 225 mg/ml solutions had an average fiber diameter of approximately 816 nm with a range from 120 nm to approximately 3.5 µm. At 250 mg/ml average fiber diameter increased to 1.7 µm and the scaffolds exhibited fibers ranging from 240 nm to 6.2 µm. Average diameter in scaffolds prepared from the 275 mg/ml solutions decreased to 750 nm, substantially less than the average fiber diameter observed in scaffolds prepared from starting solutions ranging from 125-250 mg/ml (FIG. 6).

In order to fabricate scaffolds from the 225 and 250 mg/ml solutions it was necessary to increase the diameter of the washer used to direct the electrospinning jet towards the grounded target. We suspect that the mass and momentum of the electrospinning jet at these higher starting concentrations restricts its lateral deviations as the jet passes from the syringe to the air gap targets. As we increased the diameter of the washer placed over the syringe, the lateral deviations in the spiral jet increased and fibers collected across the grounded piers forming a cylindrical construct. In parallel with this change, it was also necessary to (A) move the grounded targets closer to the electrospinning reservoir, and (B) reduce the distance between the piers of the bi-polar ground (Table 2). These modifications appear to bring the targets within a domain of the electrospinning field that corresponded to the diameter of the spiraling jet of charged polymer.

Fiber Alignment.

Figure 9A:
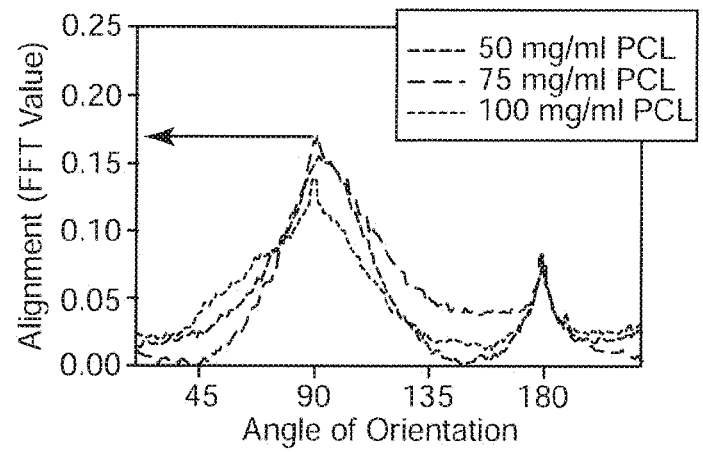
FIG. 9A-E Analysis of fiber alignment by 2D FFT. A, average fiber alignment over the entire length of constructs produced from 50-125 mg/ml solutions. B, 150-200 mg/ml solutions and C, 225-275 mg/ml solutions. Average fiber alignment is similar in each construct, although there is a trend towards an increase in the peak FFT value as a function of increasing average fiber diameter. Scaffolds produced from the 50 and 75 mg/ml starting concentrations exhibit a broader distribution of alignment values and shoulders on the FFT plots (illustrated at 180° on the alignment plot) typical of structures that degrade alignment values (beads and fibers off axis). D, Fiber alignment as a function of initial starting PCL concentration and E, Fiber alignment as a function of average fiber diameter. These data indicate that increasing fiber diameter has a relatively nominal effect on increasing alignment in the electrospun constructs.
Figure 9B:
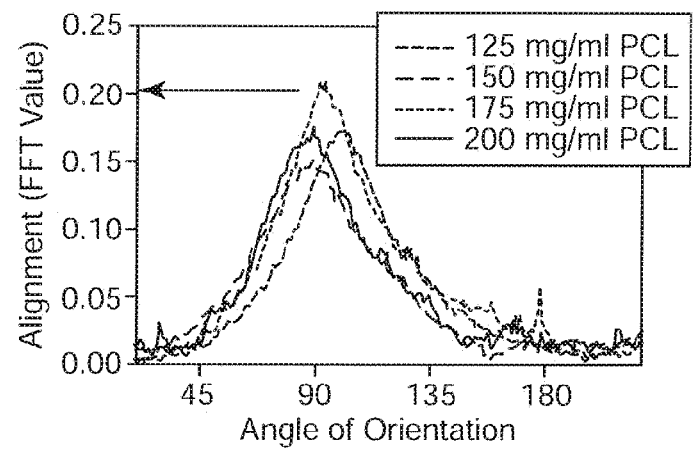
Figure 9C:
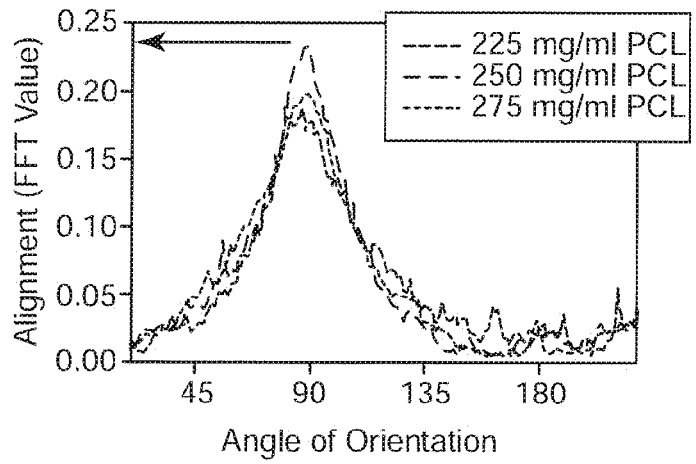
Figure 9D:
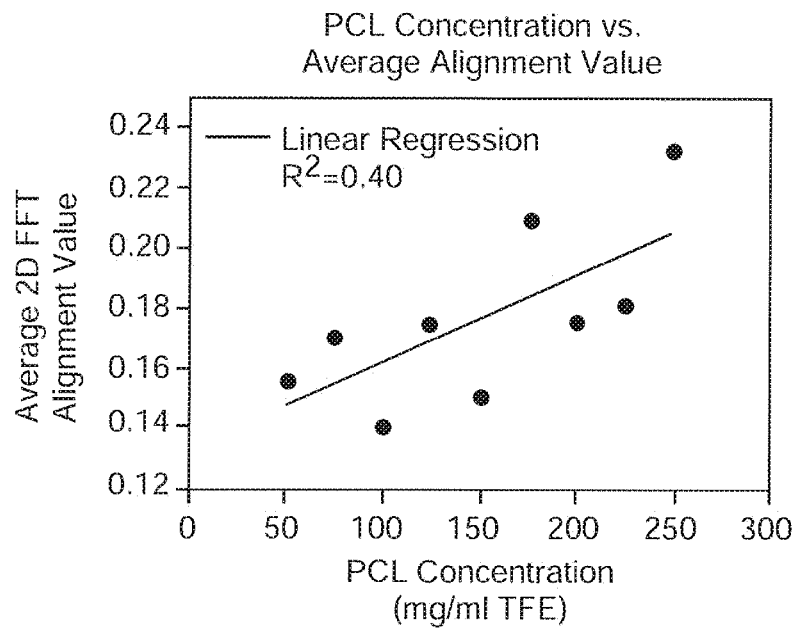
Figure 9E:
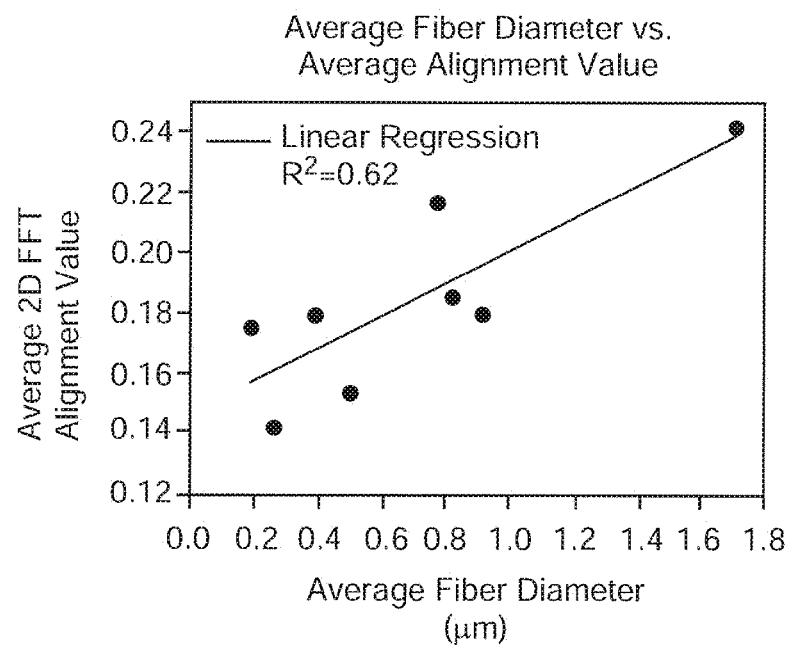

2D FFT analysis of the different scaffolds produced in this study demonstrates that fiber alignment is similar, regardless of fiber diameter, when scaffolds are produced using a bi-polar grounded target (in contrast to scaffolds produced in a conventional electrospinning systems where fiber diameter and rates of mandrel rotation interact to determine the extent of alignment). In contrast to conventional systems, varying the PCL concentration and/or increasing the average fiber diameter had little effect on fiber alignment in scaffolds produced by the air gap system (FIG. 9D-E). Not surprisingly, the principal angle of fiber alignment in all of these scaffolds was in parallel with the long axis of the cylindrical constructs (FIG. 9). However, there were some subtle differences across the samples that we examined. Scaffolds produced from the 50-100 mg/ml solutions contained structural elements that partially degraded alignment values. These scaffolds each exhibited a characteristic shoulder in the 2D FFT alignment plot (occurring at about 1800). The beaded structures and the off axis fiber that are present in this family of scaffolds undoubtedly contribute to these results (FIG. 7). Even so, these scaffolds still exhibit considerable fiber alignment, and for this family of constructs the 2D FFT analysis generated alignment values ranging from 0.14 to approximately 0.16 units (FIG. 9A). The 2D FFT analysis reported that constructs produced from starting concentrations of 125-200 mg/ml lacked the distinct shoulder detected in scaffolds produced from lower starting concentrations of PCL. Overall, these scaffolds were incrementally more aligned than scaffolds produced from the 50-100 mg/ml solutions (FIG. 9B). A similar trend was observed in scaffolds prepared from the starting solutions of 225-275 mg/ml and these samples displayed the highest degree of fiber alignment (FIG. 9C).

Materials Testing and Physical Properties.

Figure 10A:
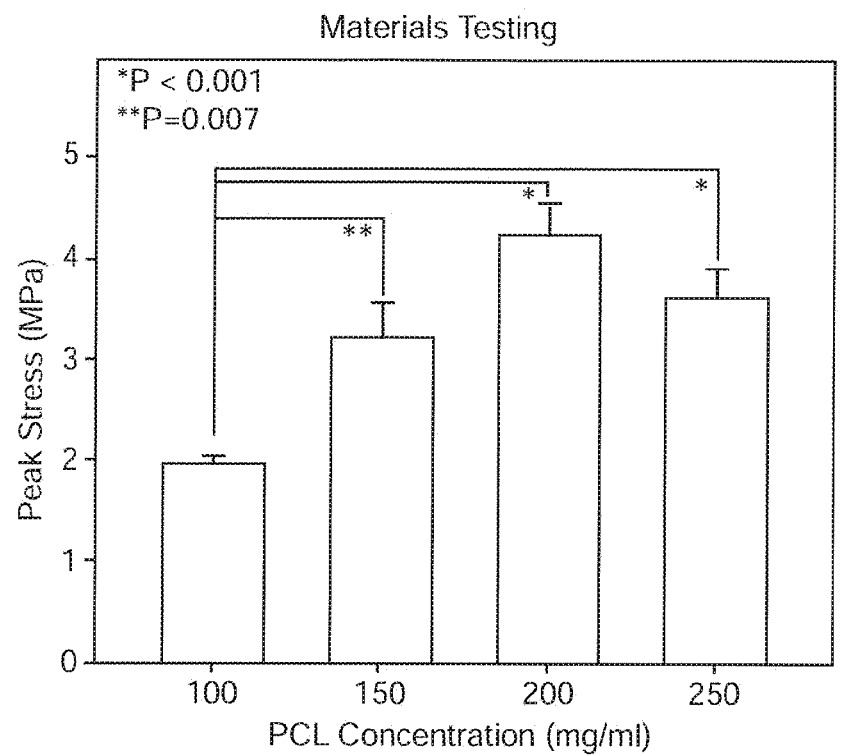
FIG. 10A-B. Materials Testing. A, Peak stress of electrospun constructs produced from varying concentration of PCL (100, 150, 200, and 250 mg/ml). The peak stress of the scaffolds increases with the increasing concentration of PCL from 100 mg/ml to 200 mg/ml. at 250 mg/ml, the strength of the construct is not significantly deteriorated, but is a little less than that of the scaffold electrospun from PCL at a concentration of 200 mg/ml. B, Void space in electrospun constructs produced from varying PCL concentrations (100, 150, 200, and 250 mg/ml) measured using the liquid intrusion method. The percentage of void space increased with increasing concentration of PCL ($P<0.05$).

To verify the structural properties of scaffolds produced in the air gap process we conducted materials testing experiments (stress at failure increases as a function of fiber alignment in electrospun materials). 2D FFT analysis indicates that fiber alignment incrementally increased as a function of starting PCL concentration (and increasing fiber diameter). A similar trend was noted in the bulk material properties of the scaffolds (FIG. 10). For example, peak stress in scaffolds produced from the 100 mg/ml solutions was ~2.00 Mpa (FIG. 10A). This value increased to 3.25

MPa in scaffolds produced from the 150 mg/ml solutions, and to 4.25 MPa in scaffolds produced from 200 mg/ml solutions. Peak stress was 3.5 MPa in scaffolds produced from the 250 mg/ml solutions. Statistical analysis of these data indicates that scaffolds produced from 150, 200 and 250 mg/ml PCL exhibited similar material properties at failure. Peak stress in each of these constructs was greater than what was observed in scaffolds produced from 100 mg/ml PCL ($P<0.007$). These values, with the exception of scaffolds produced from the 100 mg/ml solutions, compare favorably to the material properties of native rodent sciatic nerve [25].

Figure 10B:
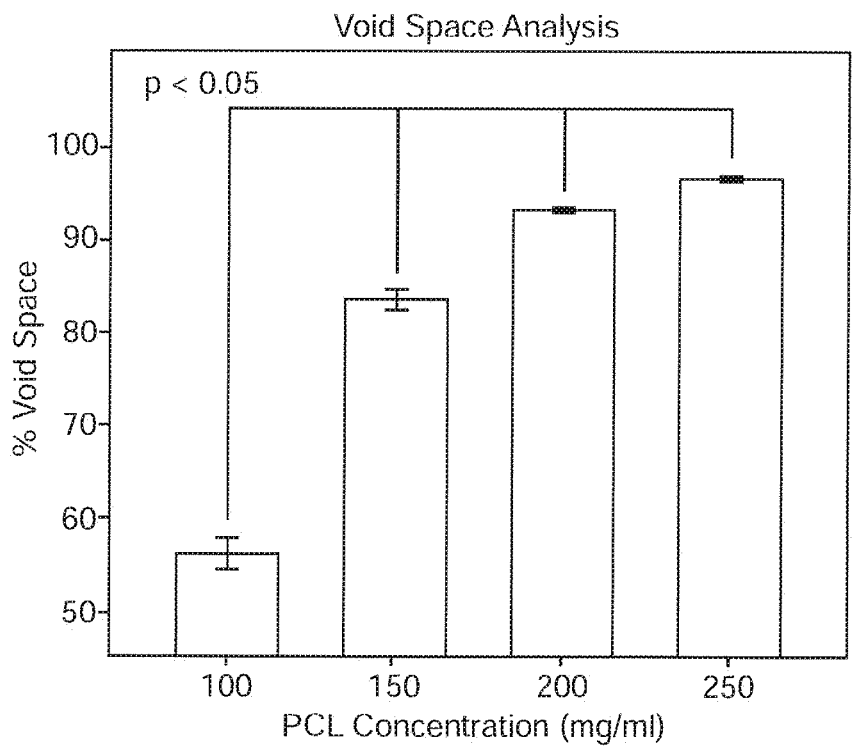

While each scaffold is composed of highly aligned fibers, considering the variable fiber diameters, the spaces between each of the individual fibers can be expected to be very different which would influence the penetration of regenerating axons. Our analysis, as determined by liquid intrusion measurements, revealed significant differences in scaffold void space ("porosity") develop as a function of starting conditions ($P<0.05$; FIG. 10B). Average void space for scaffolds produced from 100 mg/ml solutions was approximately 58% and ranged to greater than 95% for scaffolds produced from the 250 mg/ml starting solutions.

Cell Culture Experiments.

While each of the scaffolds produced in this study did exhibit similar degrees of fiber alignment, there are additional considerations that must be accounted for in the selection of a candidate construct that is to be used in nerve reconstruction. For example, scaffolds produced from 50-100 mg/ml PCL exhibit extensive beading and tensile properties that are below that of the rat sciatic nerve [25]. The beaded structures could represent obstacles to regenerating axons and or disrupt guidance cues present in the aligned fibers. At the other extreme, scaffolds produced from the 275 mg/ml solutions have highly aligned arrays of fibers and material bulk material properties that exceed the sciatic nerve of the rodent. However, the electrospinning configuration that is necessary to process these solutions into a scaffold results in very short constructs, limiting their utility in a clinical applications.

Figure 11A:
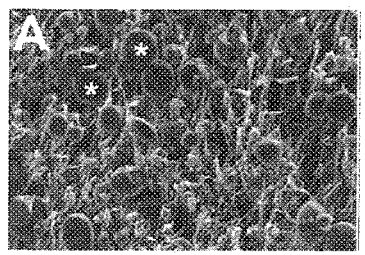
FIG. 11A-G. Cell Culture Experimentation. A, SEM tangential sections of poly caprolactone based (PCL: MW of 65 Kda; it was found other PCL molecular weights do not work as well in this 2 pole electrospinning system) scaffolds produced from 125 mg/ml, B, 200 mg/ml and C, 250 mg/ml. While there is evidence of fiber damage and some compression in the cut zones (to some extent this effect can be mitigated by infusing the grafts with agar or other materials that fills the voids prior to cutting, the minor damage induced does not represent a serious limitation, in part because the cutting plane is not very long in guide use and it is usually desirable to avoid infusing materials into the grafts that may leave a residue after trimming), note the high porosity of the constructs and the channels that are formed and present between each individual fiber, these elongated pore spaces are arrayed in parallel with the axis of fiber alignment. Scaffolds produced from the 125 mg/ml solutions have the beaded structures typical of these constructs (Panel A, asterisks, See also FIG. 10). Scale bar in C=10 μm for A-C. D, Fluorescence images of dorsal root ganglia (DRG) in scaffold produced from the 125 mg/ml solution that has been cultured for 7 days in the presence of nerve growth factor. E, DRG cultured under similar conditions in scaffold produced from 200 mg/ml solution and F, DRG cultured under similar conditions in scaffold produced from 250 mg/ml solutions. Note the increasing trend towards fasciculation with increasing PCL fiber diameter. This effect is particularly evident in the samples cultured in the scaffolds produced from the 250 mg/ml solutions. The axons that are projecting perpendicular to the primary axis of the construct are within the channel used to implant the DRGs into the scaffold (arrows in F and G). G, Corresponds to F but stained to reveal nuclei. Note the extensive overall cellularity of the cultures and the association of nuclei with the axons bundles. The asterisks in F and G represent the initial implant site for the DRG. Inset in G represents an illustration regarding the method and site of DRG injection into the scaffolds. Bar in G represents 100 μm in D-G. These data suggest that a critical pore size associated with scaffolds produced from the 250 mg/ml solutions that axons will grow along fewer tracks, the guide under these circumstances has begun to function more like a hollow cylinder and is allowing axon aggregation or bundling to occur (again a process that is associated with reduced axon targeting, an undesirable result).
Figure 11B:
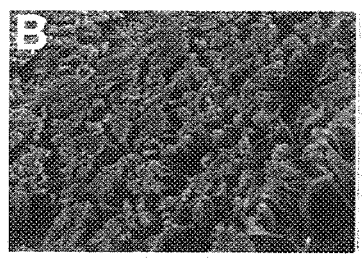
Figure 11C:

An additional consideration regarding the physical properties of the constructs concerns how the functional porosity of the scaffolds affects the axonal regeneration. In these assays we tested how effective different scaffold configurations were at supporting the penetration of axons into the fiber arrays using explanted dorsal root ganglia (DRG) as a model system. Scaffolds produced from the 125 (average fiber diameter=383 nm+/−228 nm S.D.), 200 (906 nm+/−923 nm) and 250 (1,667 nm+/−1,165 nm) mg/ml PCL starting concentrations were tested in these assays (FIG. 11A).

Figure 11D:
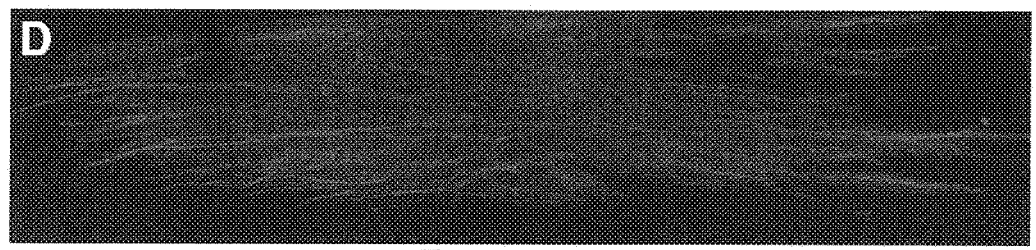
Figure 11E:
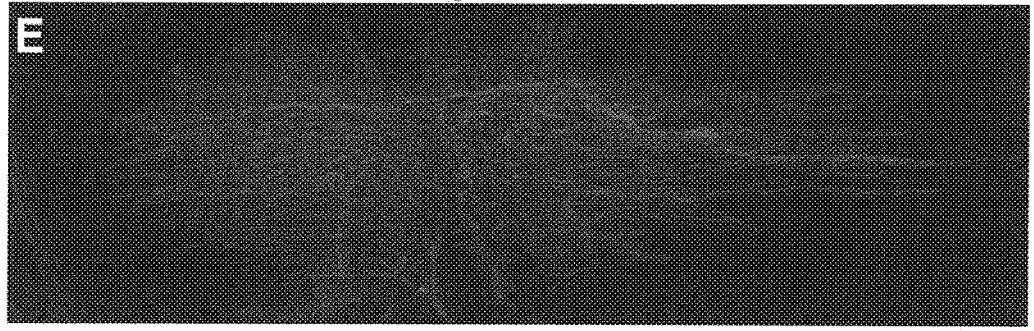
Figure 11F:
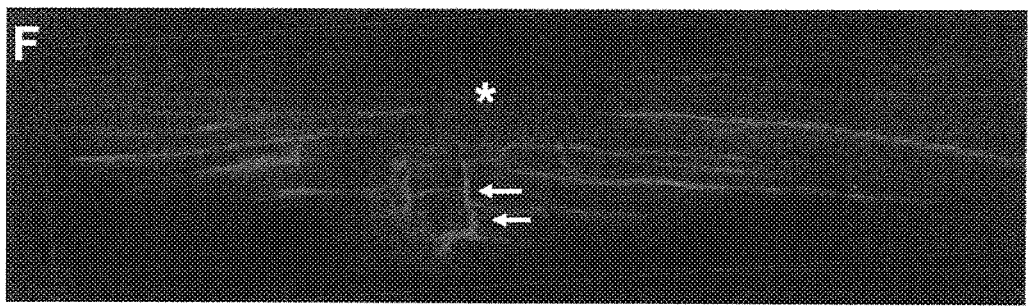
Figure 11G:
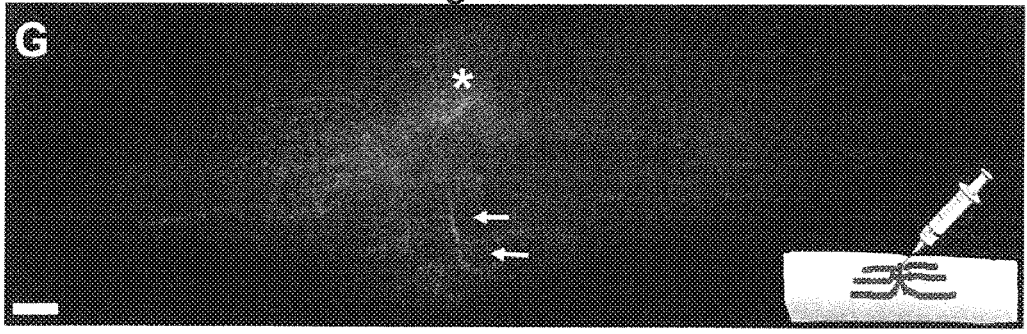

DRGs were implanted directly into the cylindrical scaffolds (scaffolds were prepared with a length of 10-15 mm and 5-7 mm in diameter) and cultured for 7 days in the presence of NGF. At the conclusion of this experimental interval all the scaffolds exhibited axons that projected into and parallel with the surrounding fiber arrays (FIG. 11D-F). These experiments suggest that constructs composed of smaller diameter fibers foster the penetration of numerous individual axons along individual PCL fiber tracks (or perhaps more accurately within the pore spaces). This pattern was particularly evident in samples cultured in the scaffolds prepared from the 125 mg/ml starting solutions. At the other extreme, DRGs plated into scaffolds prepared from the 250 mg/ml solutions exhibited pronounced fasciculation (FIG. 11F). In these cultures the axons appeared to interact with one another, form bundles and then pass along far fewer fiber tracks. A nuclear stain of the explanted cultures revealed that cells associated (Schwann cells and interstitial fibroblasts) with the DRGs heavily infiltrated the scaffolds and tracked in association with the DRG neurons (FIG. 11G).

Preliminary peripheral nerve reconstruction experiments. For in vivo testing, we prepared nerve guides from the 200 mg/ml starting concentrations of PCL. This construct formulation exhibited highly aligned fibers, excellent material properties and, extensive void spaces to support the penetration of axons along individual tracks (which in cell culture experiments suppressed axon fasciculation). In these experiments, a 10 mm section of the right sciatic nerve was removed and replaced with an electrospun nerve guide of the invention.

During the 1-2 weeks after surgery, the lesioned animals walked on 3 limbs and carried the injured limb. Motion at the knee and distal joints was substantially absent. After 3-4 weeks the animals carried weight on the injured leg, but gait in this limb was characterized by a pronounced abduction at the hip. By 6 weeks, gait improved and the exaggerated abduction at the hip was replaced with motion in more normal planes as mobility increased at the knee and ankle joints. At this time point, the animals also responded to a sensory stimulation in the guise of a withdrawal reflex in response to a foot pinch. Given these results, implants were recovered 7 weeks after the initial surgical reconstruction.

Figure 12A:
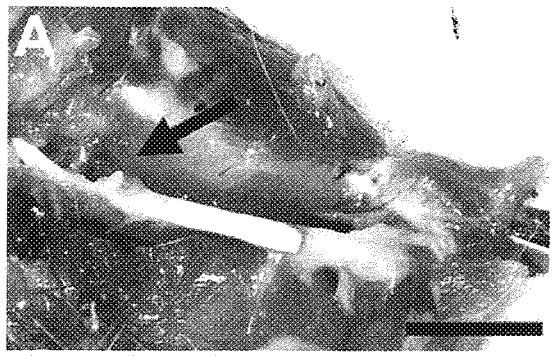
FIG. 12A-F. Nerve Reconstruction: Frozen Sections. A, representative implant recovered after 7 weeks in vivo. Arrow indicates the proximal attachment site of the implant. The guides were well integrated into the tissue of the damaged nerve. Bar in A=10 mm; B, Nomarski image of frozen sections taken mid-point in guide. Note the anisotropic nature of the tissue. C, DAPI staining; D, Neural filament 68 (NF-68); E, Myelin basic protein (MBP); and F, S100 Schwann cell marker. B-F captured with 40× objective. Bar in F=100 μm for B-F.
Figure 12B:
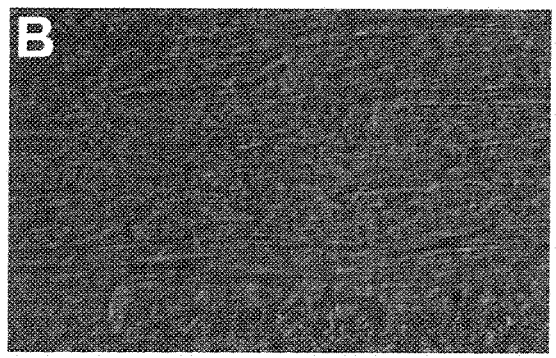
Figure 12C:
Figure 12D:
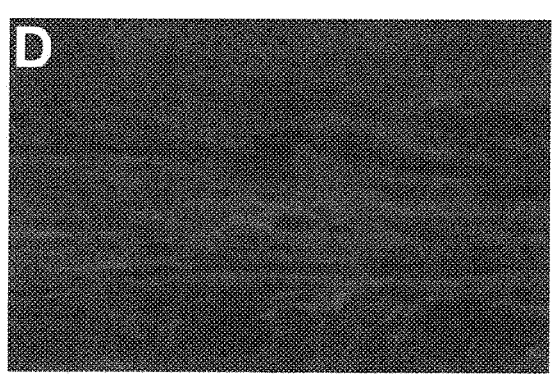
Figure 12E:
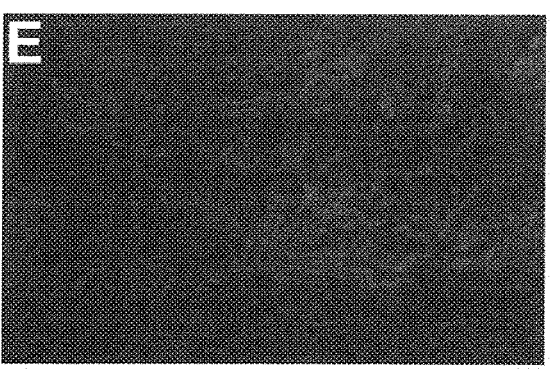
Figure 12F:
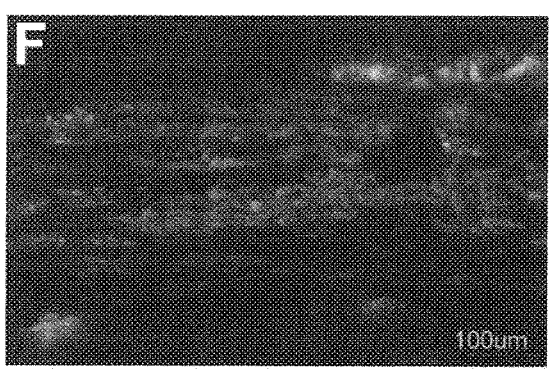

At recovery the implanted nerve guides were visibly well integrated with the stumps of the transected nerves (See FIG. 12A). The guides lifted easily out of the surrounding tissue, and there was very little evidence of fibrosis on, or in the vicinity of the implant sites. Frozen sections taken from the mid-point of the regenerating tissue had a pronounced anisotropic structure and were densely populated with cells (FIG. 12B-C). Staining for NF-68 revealed a dense population of axons in the regenerating tissue. These axons were aligned in parallel with the long axis of the cylindrical nerve guides (FIG. 12D). Myelin basic protein was present in a dense fibrillar pattern (FIG. 12E). Staining for S100 revealed elongated Schwann cells that were aligned in parallel with the long axis of the regenerating tissue (FIG. 12F). Together, the staining patterns for S100 and MBP suggest that a subset of the axons present in these central domains (of the implants) is actively undergoing myelination.

Figure 13C:
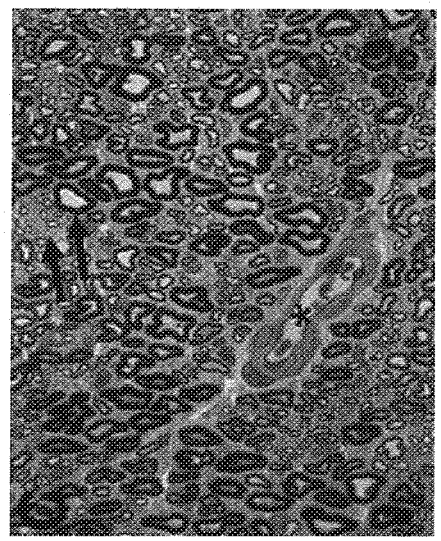
FIG. 13A-G. Nerve Reconstruction: Thick Sections. A-B: control sciatic nerve samples. Sections are densely populated by myelinated nerves. Scattered blood vessels are present (A, arrow). The epineurium is well defined (B, arrow); C-D: samples taken within 1 mm of the proximal nerve stump. Myelinated and non-myelinated axons of varying caliber are present (C, arrows). (*) in C denotes a blood vessel, arrow in D denotes external capsule of implant. E, sample taken within 5 mm of the proximal nerve stump. This domain was characterized by bundles of axons surrounded by a delimiting band of tissue that resembles the perineurium of native nerve (E, arrow). F, samples taken 8-10 mm distal to the proximal nerve stump. Axon caliber and density is reduced with respect to the proximal domains depicted in C-E. Arrowhead denotes the perineurial-like structure (precursor to the structure present in E). Note the nearly uniform alignment of the axons in all of the cross sections. All images captured with a 100× oil immersion lens. Bar in F for A-F=10 μm. G, Frequency of the regenerating axon 2D cross-sectional area at proximal and distal sites of the implanted scaffold. The frequency at which the smaller caliber axons are encountered in the distal domains is greater than the proximal aspects of the tissue, typical of the early- to mid-stages of nerve regeneration.
Figure 13F:
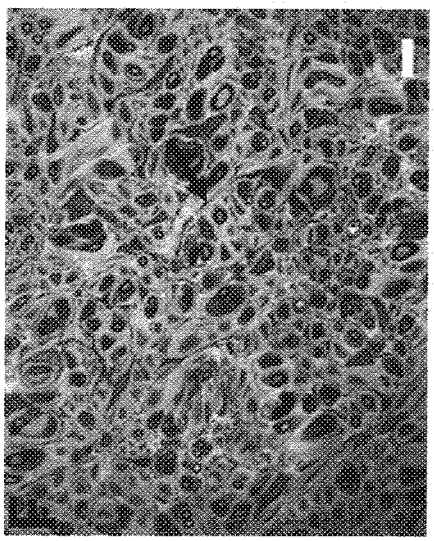
Figure 13B:
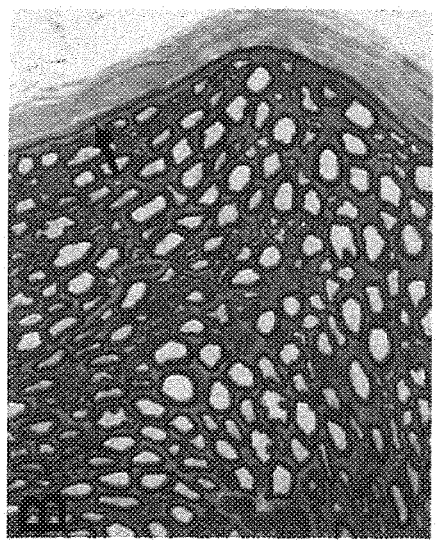
Figure 13E:
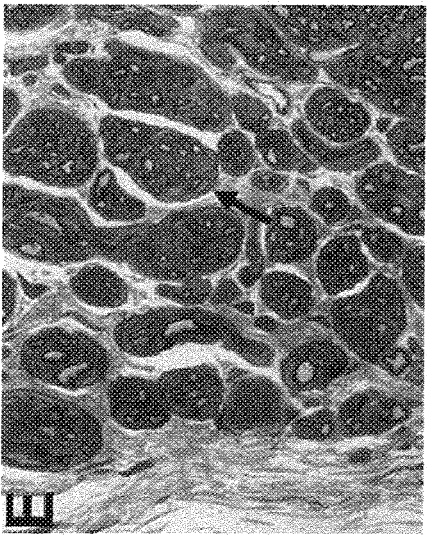
Figure 13A:
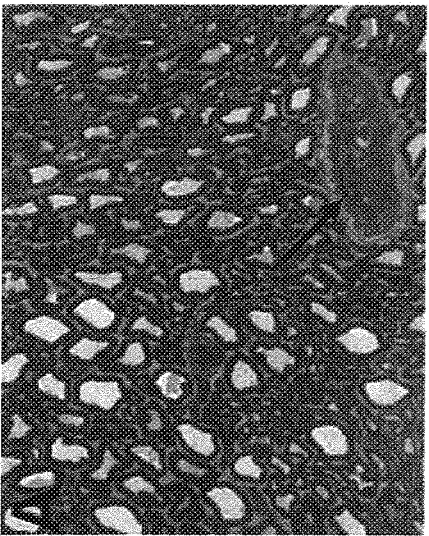
Figure 13D:
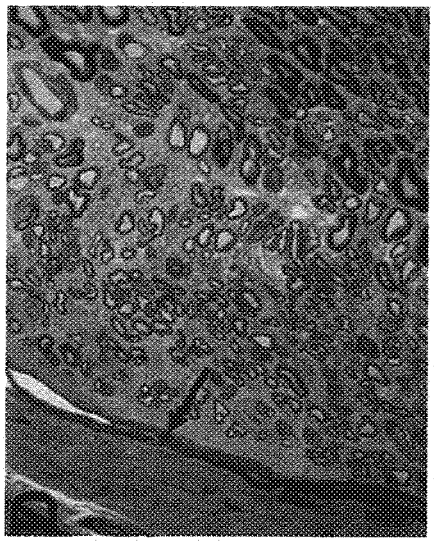
Figure 13G:
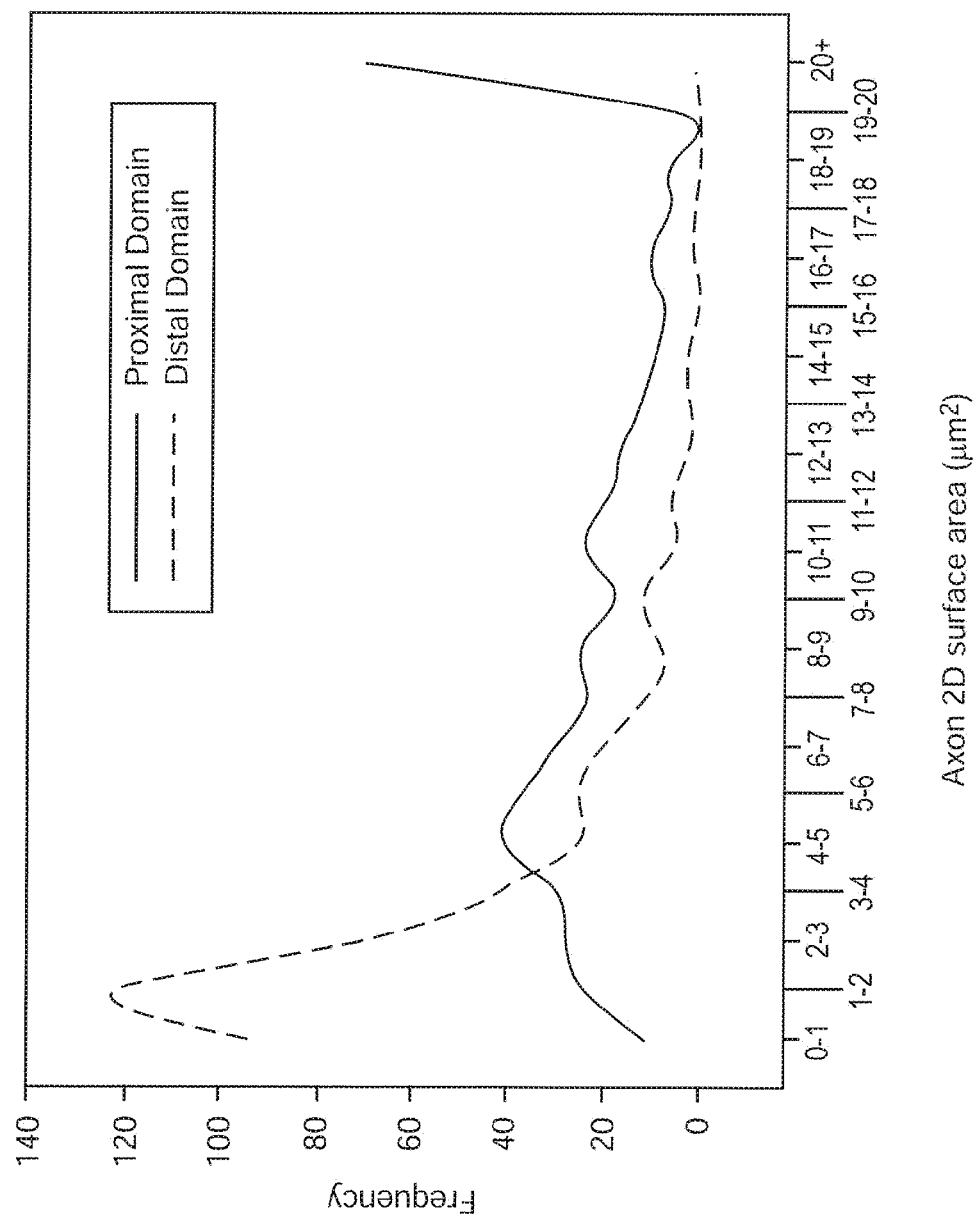
Figure 14A:
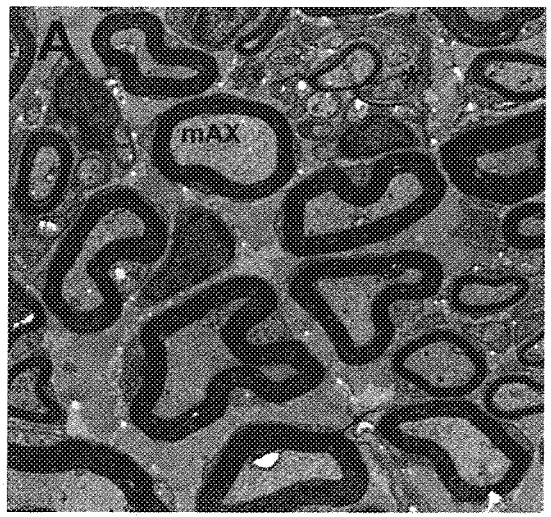
FIG. 14A-D. Transmission Electron Microscopy. A and B, Proximal domains, C and D distal domains of regenerating tissue. In these cross sections, the proximal and distal domains exhibit well differentiated myelinated axons (mAX) interspersed with unmyelinated axons (*). Functional blood vessels in the regenerating tissue range from capillaries to small arterioles (B, BV) with smooth muscle cells (B, Sm). Distal domains (C and D) contain the profiles of numerous Schwann cells (Sc) in association with small caliber axons. The box in C denotes one of these profiles, in D a high magnification detail of a Schwann cell surrounding a small caliber axon and adjacent to a fibroblast (F) is illustrated. Note the relatively high degree of maturation in the myelin sheaths. Cytoskeletal elements are clearly evident in the axons. Interstitial spaces are filled with parallel arrays of collagen fibrils (B, inset shows a tangential section of collagen fibers, also see Col in B and D). Inset D illustrates a PCL fiber, note the lack of myelination on these structures.
Figure 14B:
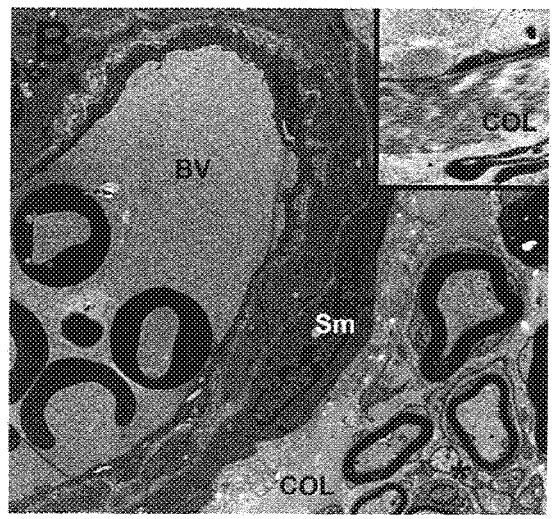
Figure 14C:
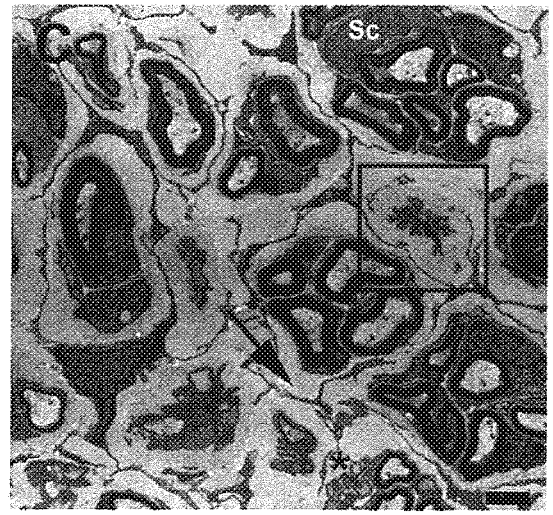
Figure 14D:
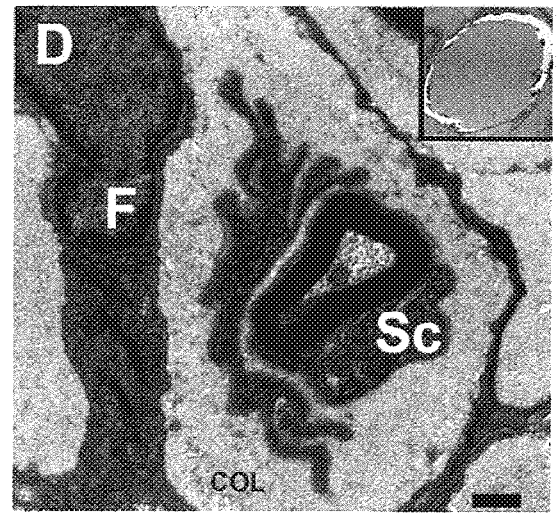

To verify the architectural organization of the reconstructed nerves, we embedded representative samples for light and transmission electron microscopy, and cut them in cross section. Thick sections imaged by light microscopy revealed that the proximal segments of the nerve guides that were densely packed with myelinated axons. These axons were more variable in size than axons present in a normal sciatic nerve (see FIG. 13 A-B). Non-myelinated axons were interspersed with the myelinated axons (FIG. 13C, arrows and FIG. 14A). The PGA/PLA coating that we used on the implants induced the formation of an epineurium-like capsule (FIG. 13D). Samples taken from the mid-point of the grafts exhibited numerous bundles of axons that were surrounded by a delimiting band of tissue that was reminiscent of the perineurium (FIG. 13E). Cells with an elongated, spindle-like morphology were present in association with the periphery of these fascicule-like structures (FIG. 14C, arrow). Functional blood vessels, as indicated by the presence of red blood cells (FIGS. 13C, asterisk and 14B), were observed at scattered intervals within the reconstructed tissue.

Overall, the extent of myelination present on individual axons is surprisingly mature within the regenerating tissue. The myelin sheath surrounding the axons was considerably thicker than anticipated given the relatively short period of time allowed for regeneration (FIG. 14). Also surprisingly, the regenerating tissue was packed with highly aligned fibrils of collagen that were predominately oriented in parallel with the long axis of the developing tissue (FIG. 14B, inset). At this time the role of these fibers in directing axon growth remains an open question. Conversely, these fibers do not appear to have adversely affected the regeneration process; guides composed of collagen have exhibited efficacy in nerve reconstruction [26].

Using quantitative morphometrics we estimated that the proximal section of the grafts contained approximately 8,400 myelinated axons, a figure that is comparable to the estimates given in the intact sciatic nerve [27]. At the distal end, and again based on our light microscopy survey, we estimated that there were about 1,900 myelinated axons present in the regenerating tissue. Consistent with the early stages of regeneration that we have examined in this study, we observed that the average 2D myelinated axon cross-sectional area decreases as a function of increasing distance from the proximal nerve stump, and that majority of axons present in the distal domains were, on average, smaller in caliber and more uniform in size distribution as compared to the proximal domain (FIG. 13G).

Discussion

In this study, two pole electrospinning was used to fabricate "semi-solid", 3D-cylindrical constructs composed of fibers that have been deposited into highly aligned arrays that are oriented parallel to the long axis of constructs. In contrast to conventional electrospinning systems, the extent of fiber alignment in air gap spinning is clearly much less dependent upon the size of the fibers. Using the present air gap system, it is possible to electrospin scaffolds composed of aligned PCL fibers ranging from less than 200 nm to approximately 1.5-1.8 µm in average cross-sectional diameter. The uncoupling of fiber alignment from its normal dependence on fiber diameter has allowed us to develop and test a family of scaffolds with distinct material properties and intrafiber spacing (void volume) to select the best configuration for a nerve conduit.

Several studies already have demonstrated that 2D sheets composed of anisotropic electrospun fibers can effectively induce the alignment of neuronal cells [10-12] as well as the directed, and accelerated migration of a variety of cell types [13,28,29]. This type of 2D surface is particularly well suited for in vitro applications; cells plated onto a flat sheet are readily accessible for analysis by a variety of microscopy techniques [30]. These 2D constructs are less well suited for use in the actual reconstruction of a damaged nerve. Sheets of electrospun materials have been described as "3D" in the literature; however, the 3D aspect of such materials may be overstated and is largely confined to a description of the surface topography of the scaffold. Air gap electrospinning makes it possible to produce a truly 3D cylindrical construct composed of linear arrays of fibers oriented along a common axis. Cylindrical scaffolds which are 15-20 mm in cross-sectional diameter have been produced using this system and virtually no degradation in fiber alignment has been observed in the large scale constructs.

As noted, the fabrication of nerve guides using conventional electrospinning processes has been explored to some degree. Electrospun PCL-based devices have been fabricated as hollow, cylindrical tubes that are designed to confine regenerating nerves to the lumen of the device while restricting the penetration of inflammatory cells into the injury site [18]. These hollow devices appeared to initiate only a nominal inflammatory response when used in sciatic nerve reconstruction. Additionally, PCL breaks down slowly, and as a result, has displayed good biocompatibility in a variety of bioengineering applications. Our experiments yielded similar results and we did not observe evidence of inflammatory cells or scarring within our guides. Morphometric analysis would suggest that hollow nerve guides produced by conventional electrospinning processes using PCL can direct perhaps 25% of the axons (based on volume of tissue, not the actual number of axons) present in the proximal stump to regenerate down the length of 10 mm tube over a 14 week interval [18]. While the metrics between this study and our study vary to some degree, our estimates suggest that we achieved a similar degree of axon regeneration (25% of the axons present in the proximal section reached the distal end of the guides as determined by morphometric analysis) in our 3D guides over a 7 week interval (we believe the regeneration process has not reached its penultimate extent by any means in our experiments-given the very brief time interval of these preliminary experiments.

The extent of functional recovery that can be achieved after nerve injury is limited by the nature of the precipitating injury and by processes that exist downstream to the actual wound bed. For example, in peripheral nerve injuries, functional recovery may essentially be complete if the continuity of the endoneurium is spared during precipitating event (neuropraxia). In this type of injury the myelin sheath that is distal to the wound bed represents a "full-length" guidance conduit. The regenerating axons are confined to returning to the end organs associated with the surviving endoneurium. These observations suggest that guidance cues incorporated into a synthetic nerve guide can play a critical role in directing the regeneration process [9]. The extent, and fidelity, of nerve regeneration and subsequent functional recovery is greatly reduced once the endoneurium has been compromised (axonotmesis and neurotmesis).

While hollow electrospun devices afford a measure of improvement over earlier nerve guide designs fabricated by more conventional processes, they represent a relatively early evolutionary stage in nerve guide design. The autologous nerve guide remains the gold standard treatment for nerve injuries that require reconstruction, and the unique 3D design of the present nerve guides is modeled on the architecture of these "natural guides". The use of autologous implants is not without its limitations. For example, the action of harvesting the autologous tissue obviously results in morbidity at the donor site. The axonal debris that is present within the harvested tissue also must largely degrade before regenerating axons can penetrate the tissue, a time delay that can exacerbate the onset of degenerative changes in the distal tissues (e.g. loss of motor end plates in muscle, muscle disuse atrophy). While regenerative processes in the peripheral nervous system can restore a considerable degree of function to end organ tissues, the recovery of fine motor skills, unfortunately, is limited. It is likely that functional recovery can be improved by (A) accelerating axon growth across the injury bed and simultaneously (B) confining these regenerating axons to a spatial domain (tissue plane) that mimics their original position within the nerve. The present synthetic guides are designed to provide the guidance cues that are inherently present in autologous grafts without the time delay needed to degrade the axonal fragments present in the harvested tissues. In addition, it is likely that the present 3D guides can be used to confine regenerating axons to the tissue plane where they existed prior to the precipitating event that damaged the nerve. This can be expected to increase the probability that the axons passing down the guide structure will emerge closer to their original position, a circumstance that should improve targeting and thereby increase functional recovery.

In summary, air gap electrospinning makes it possible to directly incorporate guidance cues into the structure of a truly 3D construct. The pore spaces present between the aligned fibers in these nerve guides readily supported axonal growth. Somewhat surprisingly, even scaffolds composed of the smallest diameter fibers supported the penetration of axons and Schwann cells in in vitro studies. Physical and biochemical cues that accelerate axonal regeneration can be expected to further improve functional recovery in distal tissues by limiting end-organ complications associated with de-innervation (i.e. atrophy). [29,31].

Conclusion

In peripheral nerve injuries, the extent of recovery depends upon the appropriate targeting and the time taken by the regenerating axons to reach and re-innervate the target tissues. In contrast to conventional hollow nerve conduits, the present novel 3D nerve guides with dense arrays of anisotropic fibers are very effective at directing axon elongation along a defined axis, thereby providing the spatial cues for proper targeting. These guides provide a straight path for the regenerating axons which is the shortest distance to reach their targets. Also, in contrast to the autologous grafts, the use of air gap electrospun nerve guide in addition to avoiding the donor site morbidity, eliminates the time lag that occurs due to the requirement for degradation of pre-existing axons from the autologous graft before the regenerating axons can penetrate the graft. These factors can be expected to accelerate regeneration across the injury site, and thereby reduce associated complications, and improve functional recovery.

Example 2

Gradients of Therapeutic Substance

In human nerve injuries, where a segment of tissue has been injured to the point where a nerve guide must be used to re-establish continuity of the injured tissue (or otherwise direct the regeneration process) the actual physical dimensions of the nerve segment that has to be reconstructed may be relatively nominal in length. However, even the loss of a relatively short segment of tissue can represent a nearly insurmountable barrier to regeneration. There is considerable evidence that growth factor gradients established by various cells that migrate into the injury site play a critical role in directing the nerve regeneration process. Clearly, in circumstances where a nerve guide is used to reconstruct damaged tissue the regeneration process could be enhanced, and accelerated, if a specific growth factor gradient could be directly incorporated into a nerve guide prior to reconstructive surgery. However, recapitulating a growth factor gradient over the relatively short distances typically observed in nerve injuries is a daunting problem.

Figure 15A:
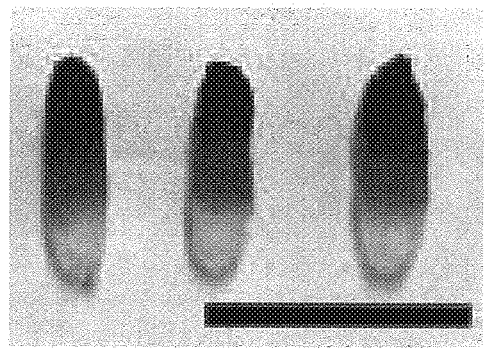
FIG. 15A-B. Alginate fibers extruded from a tuberculin syringe: A, wet state, B, after drying. Bar in A=15 mm. Blue dye selective added alginate stocks prior to freezing to illustrate the stability of the gradients during processing.
Figure 15B:
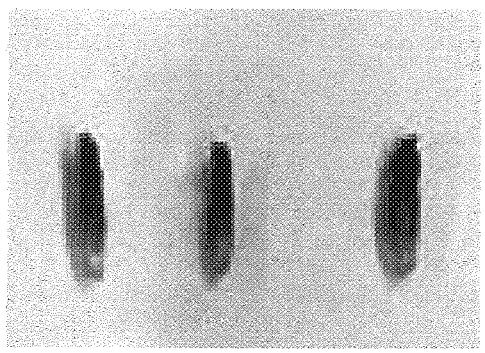

This can, however, be accomplished using the methods of the invention. FIGS. 15 A and B show CDG alginate fibers made as described above but with different concentrations of dye rather than a therapeutic agent. As can be seen, the procedure of adding aliquots and freezing between each addition, then polymerizing the thread that is formed, results in discrete bands of differing concentrations of dye molecules along the length of the thread.

Figure 16:
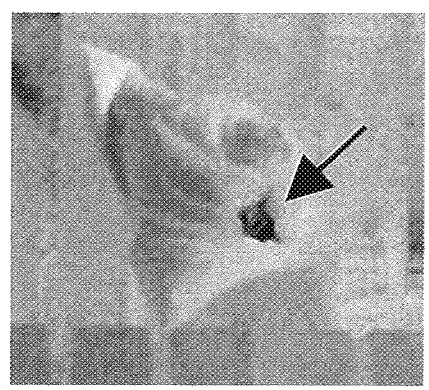
FIG. 16. Cross section of an electrospun nerve guide scaffolding. The blue dyed alginate carrier thread is present in the middle of the cylindrical construct and throughout the liner length of the construct. The depicted fiber is for illustration and does not necessarily represent the size of the fiber with respect to an actual nerve guide, which, if drawn to actual scale, would likely not be visible in this type of depiction).

In one example, a highly aligned scaffold of PCL fibers was produced by electrospinning a small volume of PCL into an air gap electrospinning system to produce a thin, tubular shaped scaffold. A thread of alginate supplemented with a dye gradient was then added to this scaffold, and the electrospinning process was then re-started and the alginate fiber was trapped in the middle of the construct. FIG. 16 shows a cross section of the electrospun nerve guide with the dyed carrier thread disposed therein (indicated by the arrow).

Example 3

Dissolution Dependent Gradients

As described above, the second type of gradient, the, Dissolution Dependent Gradient (DDG) is fabricated by varying the concentration of carrier (e.g. alginate) along the length of the thread like construct. This type of gradient can be fabricated using a constant concentration of therapeutic reagent or a variable concentration of therapeutic reagent. The basis for this type of gradient lies in the observation that alginate threads composed of low concentrations of this carbohydrate dissolve faster than alginate threads composed of higher concentrations of this carbohydrate. Thus, the rate of release of an active agent incorporated into the thread can be controlled by placing the agent within a segment of the gradient thread that will dissolve at or within a desired time frame, e.g. a first segment of the thread may dissolve over a period of days (e.g. 1-7 days), a second segment may dissolve over a period of e.g. 1-2 weeks, a third segment may dissolve over a period of e.g. 2-4 weeks, and so on for additional fourth, fifth, sixth, seventh, eighth, ninth, and tenth, etc. segments, with segments containing higher concentration of alginate (or other suitable carrier) dissolving more slowly. As described for the CDC gradient, aliquots of alginate of varying concentrations are sequentially added to the mold, which is frozen after each addition. The frozen (but not yet polymerized) thread is then extruded into a calcium bath to polymerize and the construct, which is then solid at room or body temperature. The subsequent steps in processing the thread are identical. Representative alginate concentrations that might be used in the fabrication of an exemplary DDG construct containing 7 different segments (i.e. segments 1-7) each with a different alginate concentration are presented in Table 3.

TABLE 3

Exemplary Concentrations of alginate (mg/ml) in different segments of a fiber

| | Segment number | | | | | | |
|---|---|---|---|---|---|---|---|
| | 1 | 2 | 3 | 4 | 5 | 6 | 7 |
| Concentration | 0.015 | 0.0175 | 0.0200 | 0.0225 | 0.0250 | 0.0275 | 0.030 |
| | 0.010 | 0.0125 | 0.0150 | 0.0175 | 0.0200 | 0.0225 | 0.025 |
| | 0.005 | 0.0075 | 0.0100 | 0.0125 | 0.0150 | 0.0175 | 0.020 |
| | 0.0025 | 0.0050 | 0.0075 | 0.0100 | 0.0125 | 0.0150 | 0.175 |

Example 4

Incorporation of the Growth Factor Glial Cell Line Derived Neurotrophic Factor (GDNF) into a Carrier Thread A growth factor gradient composed of GDNF that is targeted to promote, and accelerate, peripheral nerve generation is fabricated and used in a nerve gude fo the invention. GDNF is used since this peptide growth factor accelerates axon elongation in the peripheral nervous system. Two methods are used to build precision gradients; both are based on trapping bioactive agents in alginate "threads". In the first method, GDNF is directly mixed ("direct capture") into a graded series of alginate solutions (0.0025, 0.005, 0.0100, 0.0150, 0.0200, 0.0250, and 0.050 mg/ml alginate) and individual aliquots are fabricated into a continuous "thread" as described herein. The carrier thread is incorporated into a nerve guide. Release of the GDNF from the carrier thread is regulated by the differential dissolution of the alginate (which occurs as a function of alginate concentration). In the second method, the concentration of alginate is held constant and the concentration of GDMF is varied. Table 4 illustrates representative concentrations of GDNF that can be used to prepare an exemplary 15 mm long gradient thread. This exemplary gradient is designed to contain 7 different segments in the fiber. The number of segments can be varied as necessary, as can the fractional volume of each specific component or region of the gradient.

TABLE 4

Exemplary Concentrations of GDNF (ng) in different segments of an alginate fiber

| | Segment number | | | | | | |
|---|---|---|---|---|---|---|---|
| | 1 | 2 | 3 | 4 | 5 | 6 | 7 |
| Concentration | 0.0625 | 0.156 | 0.3125 | 0.625 | 1.25 | 2.5 | 5.0 |
| | 0.125 | 0.3125 | 0.625 | 1.25 | 2.5 | 5.0 | 10.0 |
| | 0.25 | 0.625 | 1.25 | 2.5 | 5.0 | 10.0 | 20.0 |
| | 0.5 | 1.25 | 2.5 | 5.0 | 10 | 20.0 | 40.0 |

Example 5

Microbeads in Threads

In yet another embodiment, a bioactive reagents such as GDNF is mixed with a solution of alginate (alginate @ 0.05 mgs/ml) and the solution is electro-aerosoled (electrosprayed) into a 2% calcium bath. The electro-aerosol process produces a very fine mist (analogous, to the mist produced by a humidifier) of alginate droplets that are associated with the bio-reactive reagent. On contact with the calcium bath the alginate polymerizes and forms a bead that captures the associated bioactive reagent. The beads are recovered, rinsed in hexafluorisopropanol (HFIP) and, lyophilized. Dry micro-carrier beads are mixed with various concentrations of alginate and a thread is produced as described herein. The final construct contains alginate micro-carrier beads supplemented with GDNF that is trapped within microbeads in segments of alginate thread. Release is dependent upon the breakdown of the alginate thread and the exposure of the micro-carrier beads to the surrounding environment.

Figure 17:
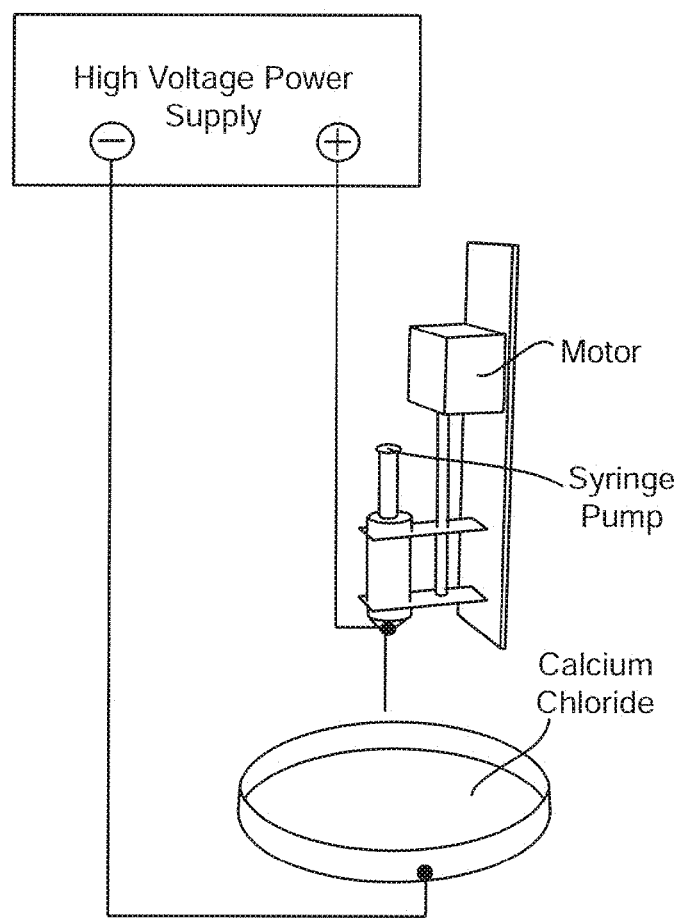
FIG. 17. Schematic depiction of device for fabricating micro-carrier beads. Alginate is placed in the syringe, the syringe is charged and directed at the calcium bath. At charging, the alginate forms fine droplets containing reagents of interest. Upon contact with the bath, the alginate polymerizes and traps the therapeutic agents in a small (micro) bead.
Figure 18A:
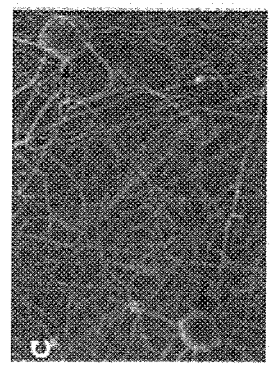
FIG. 18 A-E. A, Microscopic image of electroprocessed alginate beads, which are used to deliver bioactive materials to scaffolds, showing their uniform diameter. B, Image of beads in panel a showing the incorporation of NGF; note the nearly uniform diameter of the beads. Arrows point to same bead for reference. Bar=10 μm·C, Scanning EM of matrix with NGF/alginate beads (black arrow) incorporated within an electrospun scaffold. D, Assay assessing the bioactivity of NGF-trapped in alginate beads on DRG (dorsal root ganglion) outgrowth. Beads were prepared, incubated in trifluoroethanol or hexafluoisopropanol (electrospinning solvents) for 10 minutes (to simulate the effects of the electrospinning process), air dried and then placed in a transwell insert within a well overlying an E15 rat DRG. In the absence of NGF little outgrowth is evident, however, in the presence of NGF in the media neuritic outgrowth occurs. This effect is dramatically enhanced with NGF-delivered via electrospun alginate beads. Event incubating DRGs with higher concentration of NGF failed to produce the robust growth effects produced when NGF was delivered via the alginate beads E, Schematic of strip assay. The strips represent aggrecan painted onto a culture dish. This carbohydrate mimics the effects of the glial scarring that inhibits axon growth in spinal cord injury. DRGs are placed between the strips and exposed to NGF to induce axon growth. Electrospun matrix with/without Chondroitinase is then placed into each culture plate for 7 days. In the absence of chondroitinase, DRG neurites were inhibited from growing on aggrecan lanes (lane boundaries marked by arrows). However, in the presence of chondroitinase the growth inhibitory properties of aggrecan were neutralized. Controlled release studies with materials like NGF trapped in the beads have shown that the beads provide continuous release (as determined by ELISA) for at least 15-21 days, far longer than expected. More prolonged release can be expected if the beads are processed into a scaffold where they become trapped between and within the fibers, or incorporated into a carrier thread. Beads within the fibers or carrier threads are only available to release substances they contain once the fibers or threads begin to degrade.
Figure 18B:
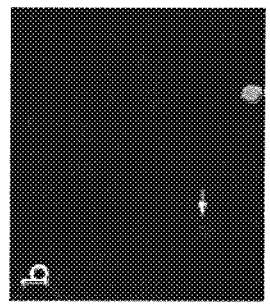
Figure 18C:
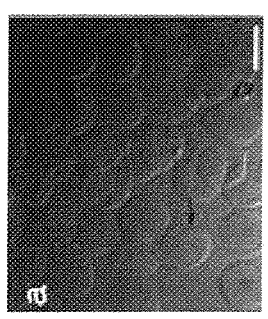
Figure 18E:
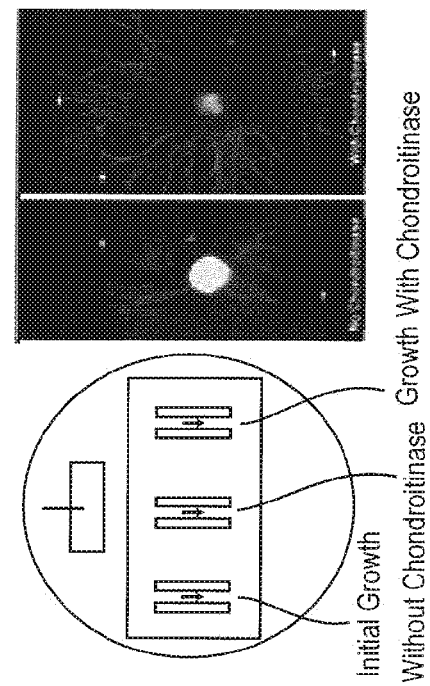
Figure 18D:
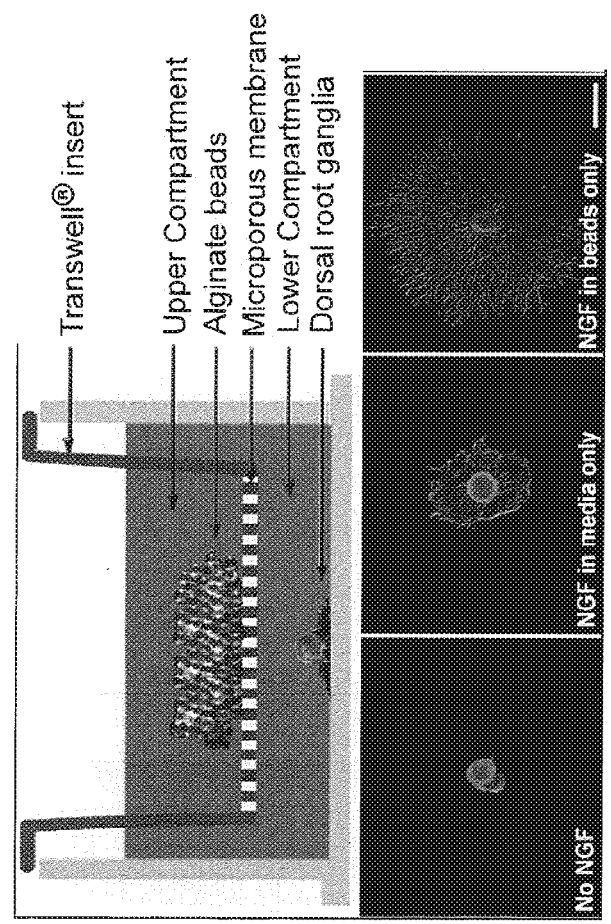

In an exemplary preparation, 10.0 mg dry GDNF was suspended in 200 microliters of sodium alginate (0.025 mg/ml) and protease free BSA (0.025 mg/ml) in DI water. FIG. 17 shows an exemplary setup of an apparatus for use in producing micro-carrier beads. The solution is loaded into a 1 ml syringe and placed in a vertical position 25 cm away from a metal plate and charged to +20 kV, the metal plate is charged to −20 kV. A glass culture dish with a 2.0% calcium chloride solution was placed on the grounded metal plate. With charging, a fine aerosol was produced, and, on contact with the calcium bath, alginate beads formed, trapping the growth factor in the alginate. Beads were collected, washed in HFIP and lyophilized. Beads can be stored at −70° C. and/or added directly to electrospinning solutions with PCL and processed into 3D nerve guides or into alignate threads to produce unique gradient compositions of therapeutic substances. It is also possible to trap cells into these mirocarrier beads by carrying out the processing in solutions that are physiologically relevant.

To manufacture threads which contain the beads, aliquots containing different concentrations of alginate are mixed with micro-carrier beads containing an agent of interest, usually a therapeutic or pharmaceutical agent, e.g. a growth factor. The solutions of alginate are then added in a sequential manner to a cylindrical "casting" vessel as described above; for small diameter threads (approximately 100 μm in diameter) small bore sections of Teflon tubing may be used, and for larger sizes a tuberculin syringe is used. The initial volume of alginate is frozen. After freezing, the next aliquot in the gradient series (higher concentration of alginate also containing microbeads) is added to the vessel and frozen; these sequential cycles are continued until the final gradient is achieved. A continuous thread is produced by extruding the frozen alginate column into a 2% calcium bath. The resulting thread is dried and "cured" in a rinse of HFIP to form a filament of alginate with very precisely defined spatial domains of microbeads. As is the case with other embodiments of the carrier thread described herein, the domains may be varied by alginate concentration, by the number of beads added to a domain, and/or by the concentration of active agent present in the microbeads that are added to a domain (which may be different for each domain), or by using combinations of these techniques.

This process and the resulting beads, as well as experimental results obtained using the beads alone, is presented in FIG. 18A-E. The results demonstrate that alginate encapsulated proteins are protected from damage induced by organic electrospinning solvents (and potentially other protein damaging solvents) and that the encapsulated material is released into the surrounding environment in a bioactive form.

Example 6

Treatment of Spinal Cord Injuries

Treatment of spinal cord injuries using the nerve guides of the invention was carried out using a rat mammalian model. The spinal cord was exposed after laminectomy, a 3 mm section was removed by complete spinal cord transaction (FIG. 19A), leaving a 3 mm gap in the tissue (FIG. 19B). The gap was then filled with a segment of the electrospun PDS scaffold either with or without various growth factors and or enzymes designed to promote regeneration (FIG. 19C). The growth factors are designed to support axon growth and survival, the chroidinase ABC enzyme is present to degrade the scar tissue that inhibits regeneration. FIG. 19D shows a 10 mm section of spinal cord that was repaired with an electrospun matrix after about 3 weeks. The tissue was fixed and cut by frozen section. The reconstructed spinal cord is shown at the top of the panel, the arrows denote the portion of the cord that was sectioned in longitudinal section and then stained with DAPI (labels all cell nuclei). DAPI label revealed a massive infiltration of cells into the implant, the border of which is marked by arrows. At later time points the implants are completely infiltrated by cells and axons. The cell population revealed by DAPI in this sample consisted mainly of oligodendrocytes and glial cells.

Treated and control rats were tested for hindlimb mobility and a graph depicting the improvement in hindlimb mobility is shown in FIG. 19E. A BBB Score of 21 represents complete mobility; a score of 0 represents complete paralysis. At early time points animals subjected to spinal cord transection move by dragging their paralyzed hind limbs. With time animals treated with the nerve guide begin to develop movements in the lower extremities, beginning at the proximal joints (hip) and then moving more distally to the feet with time. We also observe that animals early in the recovery process have a very flaccid midsection, presumably due to the spinal cord lesions impact on muscles in the abdominal area. Again, animal treated with the guides begin to recover (control untreated animals do not) and tone begins to return to these muscles. The animals look less "flattened" and more cylindrical shaped as these muscles gain tone. As can be seen, animals treated with enhanced matrices exhibit significant improvement in functional recovery as compared to untreated control rats and rats treated with control scaffolds that contain no supplementation with growth factors or enzymes designed to degrade scar tissue. After as little as 30 days animals treated with the enhanced (supplemented with growth factors and scar degrading enzymes) exhibited BBB scores approaching 8, a value that reflects motion in more than one distal joint. The extent and rate of recovery seen in this trial is unprecedented. In addition to the functional recovery observed in the lower extremities, all animals treated with implants recovered bladder function-a further indication of functional regeneration.

Electron micrographic surveys revealed dense accumulations of axons within the implants (FIG. 20A-C and FIG. 21A-E. These figures document the axonal organization that occurs after regeneration (see figure legends). The data demonstrates that in spinal cord injuries, a 3D nerve guide, and/or one or more fibers thereof, supports (facilitates, promotes, induces, etc.) the formation and penetration of functional blood vessels and regenerating axons.

REFERENCES

[1] Chen Z L, Yu W M, Strickland S. Peripheral regeneration. Annu. Rev. Neurosci. 2007; 30:209-233.
[2] Dubovy P. Schwann cells and endoneurial extracellular matrix molecules as potential cues for sorting of regenerated axons: a review. Anat. Sci. Int. 2004 December; 79(4):198-208.
[3] Lykissas M G, Batistatou A K, Charalabopoulos K A, Beris A E. The role of neurotrophins in axonal growth, guidance, and regeneration. Curr. Neurovasc Res. 2007 May; 4(2):143-151.
[4] Ichihara S, Inada Y, Nakamura T. Artificial nerve tubes and their application for repair of peripheral nerve injury: an update of current concepts. Injury 2008 10; 39(Supplement 4):29-39.
[5] Johnson E O, Soucacos P N. Nerve repair: Experimental and clinical evaluation of biodegradable artificial nerve guides. Injury 2008 9; 39(3, Supplement 1):30-36.
[6] Battiston B, Geuna S, Ferrero M, Tos P. Nerve repair by means of tubulization: literature review and personal clinical experience comparing biological and synthetic conduits for sensory nerve repair. Microsurgery 2005; 25(4):258-267.
[7] Lundborg G, Dahlin L B, Danielsen N, Gelberman R H, Longo F M, Powell H C, et al. Nerve regeneration in silicone chambers: Influence of gap length and of distal stump components. Exp. Neurol. 1982 5; 76(2):361-375.
[8] Utley D S, Lewin S L, Cheng E T, Verity A N, Sierra D, Terris D J. Brain-Derived Neurotrophic Factor and Collagen Tubulization Enhance Functional Recovery After Peripheral Nerve Transection and Repair. Arch Otolaryngol Head Neck Surg 1996 Apr. 1; 122(4):407-413.
[9] Bellamkonda R V. Peripheral nerve regeneration: An opinion on channels, scaffolds and anisotropy. Biomaterials 2006 7; 27(19):3515-3518.
[10] Chow W N, Simpson D G, Bigbee J W, Colello R J. Evaluating neuronal and glial growth on electrospun polarized matrices: bridging the gap in percussive spinal cord injuries. Neuron. Glia Biol. 2007 May; 3(2):119-126.
[11] Corey J M, Lin D Y, Mycek K B, Chen Q, Samuel S, Feldman E L, et al. Aligned electrospun nanofibers specify the direction of dorsal root ganglia neurite growth. J. Biomed. Mater. Res. A. 2007 Dec. 1; 83(3):636-645.
[12] Wang H B, Mullins M E, Cregg J M, Hurtado A, Oudega M, Trombley M T, et al. Creation of highly aligned electrospun poly-L-lactic acid fibers for nerve regeneration applications. J. Neural Eng. 2009 February; 6(1):016001.
[13] Schnell E, Klinkhammer K, Balzer S, Brook G, Klee D, Dalton P, et al. Guidance of glial cell migration and axonal growth on electrospun nanofibers of poly-e-caprolactone and a collagen/poly-e-caprolactone blend. Biomaterials 2007 7; 28(19):3012-3025.
[14] Ayres C, Bowlin G L, Henderson S C, Taylor L, Shultz J, Alexander J, et al. Modulation of anisotropy in electrospun tissue-engineering scaffolds: Analysis of fiber alignment by the fast Fourier transform. Biomaterials 2006 11; 27(32):5524-5534.
[15] Ayres C E, Bowlin G L, Pizinger R, Taylor L T, Keen C A, Simpson D G. Incremental changes in anisotropy induce incremental changes in the material properties of electrospun scaffolds. Acta Biomaterialia 2007 9; 3(5): 651-661.
[16] Newton D, Mahajan R, Ayres C, Bowman J R, Bowlin G L, Simpson D G. Regulation of material properties in electrospun scaffolds: Role of cross-linking and fiber tertiary structure. Acta Biomaterialia 2009 1; 5(1):518-529.
[17] Telemeco T A, Ayres C, Bowlin G L, Wnek G E, Boland E D, Cohen N, et al. Regulation of cellular infiltration into tissue engineering scaffolds composed of submicron diameter fibrils produced by electrospinning. Acta Biomaterialia 2005 7; 1(4):377-385.
[18] Panseri S, Cunha C, Lowery J, Del Carro U, Taraballi F, Amadio S, et al. Electrospun micro- and nanofiber tubes for functional nervous regeneration in sciatic nerve transections. BMC Biotechnology 2008; 8(1):39.
[19] Sun H, Mei L, Song C, Cui X, Wang P. The in vivo degradation, absorption and excretion of PCL-based implant. J. Biomaterials. 2006: 27(9):1735-1740
[20] Ayres C E, Jha B S, Meredith H, Bowman J R, Bowlin G L, Henderson S C, et al. Measuring fiber alignment in electrospun scaffolds: a user's guide to the 2D fast Fourier transform approach. J. Biomater. Sci. Polym. Ed. 2008; 19(5):603-621.
[21] Pham Q P, Sharma U, Mikos A G. Electrospun Poly (E-caprolactone) microfiber and multilayer nanofiber/microfiber scaffolds: Characterization of scaffolds and measurement of cellular infiltration. Biomacromolecules 2006:7:2796-2805.
[22] Dupree J L, Bigbee J W. Retardation of neuritic outgrowth and cytoskeletal changes accompany acetylcholinesterase inhibitor treatment in cultured rat dorsal root ganglion neurons. J. Neurosci. Res. 1994 Dec. 1; 39(5):567-575.
[23] Sharma K V, Bigbee J W. Acetylcholinesterase antibody treatment results in neurite detachment and reduced outgrowth from cultured neurons: further evidence for a cell adhesive role for neuronal acetylcholinesterase. J. Neurosci. Res. 1998 Aug. 15; 53(4):454-464.
[24] Shenoy S L, Bates W D, Frisch H L, Wnek G E. Role of chain entanglements on fiber formation during electrospinning of polymer solutions: good solvent, non-specific polymer-polymer interaction limit. Polymer 2005 Apr. 25:46(10):3372-3384.
[25] Abrams R A, Butler J M, Fowler S B, Botte M J. Tensile properties of the neurorrhaphy site in the rat sciatic nerve. Hand Surg 1998:23A:465-470.
[26] Stang F, Fansa H, Wolf G, Reppin M, Keilhoff G. Structural parameters of collagen nerve grafts influence peripheral nerve regeneration. Biomaterials 2005 6; 26(16):3083-3091.
[27] Schmalbruch H. Fiber composition of the rat sciatic nerve. Anat. Rec. 1986 May:215(1):71-81.
[28] Johnson J, Nowicki M O, Lee C H, Chiocca E A, Viapiano M S, Lawler S E, et al. Quantitative Analysis of Complex Glioma Cell Migration on Electrospun Polycaprolactone Using Time-Lapse Microscopy. Tissue Engineering Part C: Methods 0; 0(0).
[29] Bunge M B. Novel combination strategies to repair the injured mammalian spinal cord. J. Spinal Cord Med. 2008; 31(3):262-269.
[30] Ayres C A, Jha S B, Sell S A, Bowlin G L, Simpson D G. Nanotechnology in the design of soft tissue scaffolds: innovations in structure and function. Nanomedicine and Nanobiotechnology 2009.
[31] Bunge M B. Book Review: Bridging Areas of Injury in the Spinal Cord. Neuroscientist 2001 Aug. 1; 7(4):325-339.
(32) Li J, and Shi R. Fabrication of patterned multi-walled poly-L-lactic acid conduits for nerve regeneration J of Neuroscience Methods 165:2257-264 (2007).
(33) Yucel D, Kose G T and Hasirci V. Polyester based nerve guidance conduit design. Biomaterials 31:1596-1603 (2010).
(34). Jha B S, Colello R J, Bowman J R, Sell S A, Lee K D, Bigbee J W, Bowlin G L, Chow W N, Mathern B E, and D G Simpson. Two pole air gap electrospinning: Fabrication of highly aligned, 3D scaffolds for nerve reconstruction. Acta biomaterials (In press) 2010.
(35) Curtis R, Green D, Lindsay R M, Wilkin G P. Up-regulation of GAP-43 and growth of axons in rat spinal cord after compression injury. J of Neurocytology 22:51-64. (1993)
(36) Guth L, Barrett C P, Donati E J, Smith M V, Litson M, and Roberts E. Enhancement of axonal growth into a spinal lesion by topical application of triethanolamine and cytosine arabinoside. Exp. Neuro 88(1):44-55 (1985)

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A nerve guide, comprising a plurality of electrospun fibers which are seamlessly aligned parallel to a long axis of said nerve guide;
   at least one carrier thread comprising one or more therapeutic substances in a step gradient; and
   a plurality of open channels aligned parallel to said long axis of said nerve guide, wherein said at least one carrier thread is different from said plurality of electrospun fibers;
   wherein said at least one carrier thread comprises a plurality of segments, wherein each segment comprises the one or more therapeutic substances with a concentration that differs from the concentrations of said one or more therapeutic substances in adjacent segments such that a step gradient of concentration is formed.

2. The nerve guide of claim 1, wherein said one or more therapeutic substances includes at least one growth factor.

3. The nerve guide of claim 1, further comprising an outer sheath.

4. The nerve guide of claim 1, wherein the total length of said at least one carrier thread is from 5 mm to 125 mm.

5. The nerve guide of claim 4, wherein a length of any one of said plurality of segments is from 1 to 10 mm.

6. The nerve guide of claim 1, wherein said at least one carrier thread further comprises microbeads present in at least one of the plurality of segments, said microbeads containing an agent of interest.

7. The nerve guide of claim 1, wherein the step gradient is oriented at a non-zero angle to said long axis.

8. The nerve guide of claim 1, wherein the step gradient is oriented at right angles to said long axis.

9. The nerve guide of claim 1, wherein said gradient has a higher concentration in a middle segment of the at least one carrier thread as compared to other segments of said at least one carrier thread.

10. The nerve guide of claim 1, wherein said at least one carrier thread comprises a plasticizing agent.

11. The nerve guide of claim 1, wherein said at least one carrier thread comprises alginate.

* * * * *